US012600716B2

(12) United States Patent
Yang et al.

(10) Patent No.: US 12,600,716 B2
(45) Date of Patent: *Apr. 14, 2026

(54) COMPOUNDS FOR MODULATING ACTIVITY OF FXR AND USES THEREOF

(71) Applicant: Gannex Pharma Co., Ltd., Shanghai (CN)

(72) Inventors: Bailing Yang, Shanghai (CN); Gudmundsson Kristjan, Shanghai (CN); Liuyu Dong, Shanghai (CN); James Chen, Shanghai (CN)

(73) Assignee: Gannex Pharma Co. Ltd., Shanghai (CN)

( * ) Notice: Subject to any disclaimer, the term of this patent is extended or adjusted under 35 U.S.C. 154(b) by 923 days.

This patent is subject to a terminal disclaimer.

(21) Appl. No.: 17/756,789

(22) PCT Filed: Oct. 12, 2020

(86) PCT No.: PCT/CN2020/120369

§ 371 (c)(1),
(2) Date: Jun. 2, 2022

(87) PCT Pub. No.: WO2021/109712

PCT Pub. Date: Jun. 10, 2021

(65) Prior Publication Data

US 2022/0388997 A1 Dec. 8, 2022

(51) Int. Cl.

| | |
|---|---|
| ***C07D 413/12*** | (2006.01) |
| ***A61K 31/42*** | (2006.01) |
| ***A61K 31/427*** | (2006.01) |
| ***A61K 31/4439*** | (2006.01) |
| ***A61K 31/496*** | (2006.01) |
| ***A61K 31/501*** | (2006.01) |
| ***A61K 45/06*** | (2006.01) |
| ***A61P 1/16*** | (2006.01) |
| ***A61P 31/20*** | (2006.01) |
| ***C07D 261/08*** | (2006.01) |
| ***C07D 417/12*** | (2006.01) |

(52) U.S. Cl.

CPC ............ *C07D 413/12* (2013.01); *A61K 31/42* (2013.01); *A61K 31/427* (2013.01); *A61K 31/4439* (2013.01); *A61K 31/496* (2013.01); *A61K 31/501* (2013.01); *A61K 45/06* (2013.01); *A61P 1/16* (2018.01); *A61P 31/20* (2018.01); *C07D 261/08* (2013.01); *C07D 417/12* (2013.01)

(58) Field of Classification Search

CPC .. C07D 413/12; C07D 261/08; C07D 417/12; A61K 31/42; A61K 31/427; A61K 31/4439; A61K 31/496; A61K 31/501; A61K 45/06; A61K 31/497; A61P 1/16; A61P 31/20; A61P 3/00; A61P 3/04; A61P 3/10; A61P 9/00; A61P 9/10; A61P 9/12; A61P 13/02; A61P 13/08; A61P 3/06

See application file for complete search history.

(56) References Cited

U.S. PATENT DOCUMENTS

2017/0304270 A1* 10/2017 Or .......................... A61K 31/42

FOREIGN PATENT DOCUMENTS

| | | |
|---|---|---|
| WO | WO 2000/037077 | 6/2000 |
| WO | WO 2003/015771 | 2/2003 |
| WO | WO 2004/048349 | 6/2004 |
| WO | WO 2007/076260 | 7/2007 |
| WO | WO 2007/092751 | 8/2007 |
| WO | WO 2007/140174 | 12/2007 |
| WO | WO 2007/140183 | 12/2007 |
| WO | WO 2008/025539 | 3/2008 |
| WO | WO 2008/025540 | 3/2008 |
| WO | WO 2008/051942 | 5/2008 |
| WO | WO 2008/157270 | 12/2008 |
| WO | WO 2009/005998 | 1/2009 |
| WO | WO 2009/012125 | 1/2009 |
| WO | WO 2009/149795 | 12/2009 |
| WO | WO 2012/087519 | 6/2012 |
| WO | WO 2012/087520 | 6/2012 |
| WO | WO 2012/087521 | 6/2012 |
| WO | WO 2015/036442 | 3/2015 |
| WO | WO 2016/024010 | 2/2016 |

(Continued)

OTHER PUBLICATIONS

Han et al., "FXR Inhibits Endoplasmic Reticulum Stress-Induced NLRP3 Inflammasome in Hepatocytes and Ameliorates Liver Injury," Cell Reports., Sep. 11, 2018, 24:2985-2999.

(Continued)

*Primary Examiner* — Kamal A Saeed

*Assistant Examiner* — Meghan C Heasley

(74) *Attorney, Agent, or Firm* — Fish & Richardson P.C.

(57) ABSTRACT

Provided are a compound for modulating the activity of FXR having a structure of formula (I), a pharmaceutically acceptable salt, an ester or a stereoisomer thereof.

(I)

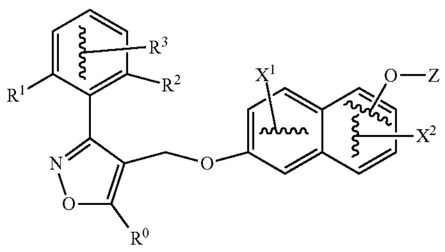

19 Claims, 2 Drawing Sheets

(56) References Cited

FOREIGN PATENT DOCUMENTS

| | | |
|---|---|---|
| WO | WO 2017/189652 | 11/2017 |
| WO | WO 2017/189663 | 11/2017 |
| WO | WO 2018/190643 | 10/2018 |
| WO | WO 2021/108974 | 6/2021 |
| WO | WO 2021/109713 | 6/2021 |

OTHER PUBLICATIONS

Akwabi-Ameyaw et al., "FXR agonist activity of conformationally constrained analogs of GW 4064," Bioorg Med Chem Lett., Aug. 15, 2009, 19(16):4733-4739.

Crawley, "Farnesoid X receptor modulators: a patent review," Expert Opinion Ther Patents., Jun. 23, 2010, 20(8):1047-1057.

International Preliminary Report on Patentability in International Appln. No. PCT/CN2020/120369, mailed on Jun. 16, 2022, 8 pages.

International Search Report and Written Opinion in International Appln. No. PCT/CN2020/120369, mailed on Dec. 24, 2020, 11 pages.

Niu et al., "Farnesoid X Receptor Ablation Sensitizes Mice to Hepatitis B Virus X Protein-Induced Hepatocarcinogenesis," *Hepatology* 65(3):893-906 (Mar. 2017).

* cited by examiner

COMPOUNDS FOR MODULATING ACTIVITY OF FXR AND USES THEREOF

TECHNICAL FIELD

The present invention relates to the pharmaceutical field associated with FXR-mediated diseases. Specifically, the present invention relates to the compounds for modulating the activity of FXR, the preparation method and pharmaceutical uses thereof.

BACKGROUND ART

The farnesoid X receptor (FXR) is a member of the nuclear hormone receptor superfamily, which is primarily expressed in liver, kidney and intestine. It functions as a heterodimer with the retinoid X receptor (RXR) to bind to the response elements in the promoters of target genes to regulate gene transcription. The FXR-RXR heterodimer binds with highest affinity to an inverted repeat-1 (IR-1) response element, in which consensus receptor-binding hexamers are separated by one nucleotide. FXR is a part of the interrelated process, in which FXR is activated by bile acid (the end product of cholesterol metabolism), which serves to inhibit cholesterol catabolism.

FXR is a key regulator of cholesterol homeostasis, triglyceride synthesis and lipogenesis (Crawley, Expert Opinion Ther. Patents (2010), 20(8): 1047-1057). In addition to dyslipidemia, obesity, vitamin D-related diseases, intestinal diseases, drug-induced side effects and hepatitis, FXR-related indications include hepatobiliary diseases, chronic hepatitis, nonalcoholic fatty liver disease (NAFLD), nonalcoholic steatohepatitis (NASH), cholestasis, liver fibrosis, cirrhosis, hepatitis B, metabolic diseases, lipid metabolism diseases, carbohydrate metabolic diseases, cardiovascular metabolic diseases, atherosclerosis, type II diabetes and diabetes complication.

A variety of compounds capable of acting as FXR modulators (or FXR-agonists) have been developed, for example, small molecule FXR modulators disclosed in WO200037077, WO2003/015771, WO2004/048349, WO2007/076260, WO2007/092751, WO2007/140174, WO2007/140183, as well as those disclosed in WO2008/051942, WO2008/157270, WO2009/005998, WO2009/012125, WO2009/149795, WO2008/025539, WO2008/025540, WO2012/087520, WO2012/087521, WO2012/087519 and WO2015/036442.

While some advances have been made in the development of novel FXR agonists, there remains a significant space for improvement of FXR agonists.

DISCLOSURE OF THE INVENTION

It is the objective of the present invention to provide novel compounds for use as FXR agonists with excellent physicochemical, in vitro and/or in vivo ADME (adsorption, distribution, metabolism and excretion) properties and excellent pharmacokinetics, and reduced side effects, the preparation method and pharmaceutical uses thereof.

Definitions

For purposes of interpreting this specification, the following definitions will apply and whenever appropriate, terms used in the singular will also include the plural, and vice versa.

As used herein, the term "$C_{1-6}$ alkyl" denotes an alkyl radical having from 1 up to 6, particularly up to 4 carbon atoms, the radicals being either linear or branched with single or multiple branching, for example, butyl, such as n-butyl, sec-butyl, isobutyl, tert-butyl; propyl, such as n-propyl or isopropyl; ethyl or methyl; more particularly, methyl, iso-propyl or tert-butyl.

As used herein, "$C_{1-6}$ alkoxy" refers to "$C_{1-6}$ alkyl-O—", and is particularly methoxy, ethoxy, isopropyloxy or tert-butoxy.

As used herein, the term "$C_{3-6}$ cycloalkyl" refers to a cyclic alkyl radical having 3 to 6 carbon atoms, for example cyclopropyl, cyclobutyl, cyclopentyl or cyclohexyl. The $C_{3-6}$ cycloalkyl can be optionally substituted by $C_{1-6}$ alkyl and/or halogen.

As used herein, the term "$C_{4-7}$ alkylcycloalkyl" refers to a combination of alkyl and a cycloalkyl group such that the total number of carbon atoms is 4 to 7. For example, $C_4$ alkylcycloalkyl includes methylenecyclopropyl.

As used herein, the term "5-10 membered aryl" refers to a 5-10 membered monocyclic- or bicyclic- or tricyclic-aromatic ring system. Typically, the aryl is a 5 or 6 membered ring system.

As used herein, the term "5-10 membered heteroaryl" refers to a 5-10 membered monocyclic- or bicyclic- or tricyclic-aromatic ring system having 1 to 4 heteroatoms. Typically, the heteroaryl is a 5 or 6 membered ring system. Furthermore, the term "heteroaryl" as used herein may encompass monovalent or divalent heteroaryls.

As used herein, the term "halogen" or "halo" refers to one or more of fluoro, chloro, bromo and iodo, and more particularly, fluoro or chloro.

As used herein, the term "$C_{1-6}$ haloalkyl" refers to an alkyl radical that is substituted by one or more halo radicals, and is particularly $C_{1-6}$ fluoroalkyl or $C_{1-6}$ chloroalkyl, such as trifluoromethyl and 2,2,2-trifluoroethyl.

As used herein, the term "pharmaceutically acceptable auxiliary materials" may include any or all solvents, dispersion media, coatings, surfactants, antioxidants, preservatives (e.g., antibacterial agents and antifungal agents), isotonic agents, absorption delaying agents, salts, drug stabilizers, binders, excipients, disintegration agents, lubricants, sweetening agents, flavoring agents, dyes, and the like and combinations thereof, as would be known to those skilled in the art. Except insofar as any conventional carrier is incompatible with the active ingredient, its use in the therapeutic or pharmaceutical compositions is contemplated.

As used herein, the term "therapeutically effective amount" refers to an amount of the compound of the formula (I) which is sufficient to achieve the stated therapeutic effects. Accordingly, a therapeutical effective amount of a compound of the formula (I) used for the treatment of a condition mediated by FXR will be in an amount sufficient for the treatment of the condition mediated by FXR.

In one aspect, the present invention provides a compound for modulating the activity of FXR having a structure of formula (I), a pharmaceutically acceptable salt, an ester or a stereoisomer thereof:

(I)

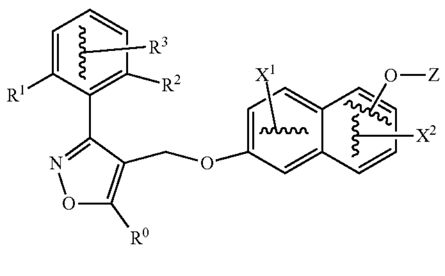

wherein:

$R^1$, $R^2$ and $R^3$ are independently selected from H, halogen, and unsubstituted or halogen substituted $C_{1-6}$ alkyl and unsubstituted or halogen substituted $C_{1-6}$ alkoxy, provided that at least one of $R^1$, $R^2$ and $R^3$ is not hydrogen, $R^0$ is selected from unsubstituted or halogen substituted $C_{1-6}$ alkyl, $C_{3-6}$ cycloalkyl, $C_{4-7}$ alkylcycloalkyl;

$X^1$ and $X^2$ are independently selected from H and halogen;

moiety —O—Z (residue Z linked to the naphthalene ring via an oxygen atom) attaches to the naphthalene ring, wherein Z is a residue selected from 5-10 membered aryl or 5-10 membered heteroaryl optionally having one or more hetero atoms selected from N, O and S, wherein the 5-10 membered aryl or 5-10 membered heteroaryl is substituted by $R^4$ and is optionally further substituted by $R^5$;

wherein $R^4$ is selected from —COOH, —$CH_2$COOH, —$NHSO_2CF_3$, —$SO_2$NH—$C_{1-6}$ alkyl, —$SO_3$H, —$CONHSO_2$—$C_{1-6}$alkyl, —$CONHSO_2$—$C_{3-6}$cycloalkyl, —$CONHSO_2$-5-10 membered aryl and —$CONHSO_2$-5-10 membered aryl substituted by $C_{1-6}$ alkyl at the aryl, and $R^5$ is selected from H, $C_{1-6}$ alkyl, halogen, $C_{1-6}$ haloalkyl, —O—($C_{1-6}$ alkyl) and —NH—($C_{1-6}$ alkyl).

In preferred embodiments of the present invention, $R^1$, $R^2$ and $R^3$ are inpendently selected from H, halogen and $C_{1-3}$ perfluoroalkoxy, such as H, Cl, F and —O—$CF_3$. In one embodiment of the invention, both of $R^1$ and $R^2$ are Cl, and $R^3$ is H. In another embodiment of the invention, both of $R_1$ and $R^2$ are Cl, and $R^3$ is F. In still another embodiment of the invention, both of $R_1$ and $R^2$ are Cl, and $R^3$ is —O—$CH_3$. In yet another embodiment of the invention, $R^0$ is —O—$CF_3$, and both of $R^2$ and $R^3$ are H. In yet another embodiment of the invention, $R^0$ is isopropyl or cyclopropyl.

In one embodiment of the present invention, Z is a phenyl, which is optionally substituted by 1-5 halogen atoms. In another embodiment of the present invention, Z is a 5-10 membered heteroaryl having one or more hetero atoms selected from N, O and S. In a preferred embodiment of the present invention, Z is a 5-6 membered heteroaryl having one or more hetero atoms selected from N, O and S. In yet another embodiment of the present invention, Z is a $R^4$ and optionally $R^5$ substituted pyridyl.

In preferred embodiments of the present invention, $R^4$ is selected from —COOH, —$CH_2$COOH, —$CONHSO_2$—$C_{1-6}$ alkyl and —$CONHSO_2$—$C_{3-6}$ cycloalkyl. In more preferred embodiment of the present invention, $R^4$ is —COOH or —$CH_2$COOH. In a most preferred embodiment of the present invention, $R^4$ is —COOH.

Preferably, $R^5$ is one selected from H, $C_{1-3}$ alkyl and halogen.

In a preferred embodiment of the present invention, Z is pyridyl; $R^4$ is —COOH; and $R^5$ is H or halogen.

Preferably, the halogen in the aforesaid substituents is fluoro or chloro.

Specifically, in preferred embodiments of the present invention, the compound having the formula (I) is of one of the following structures:

1

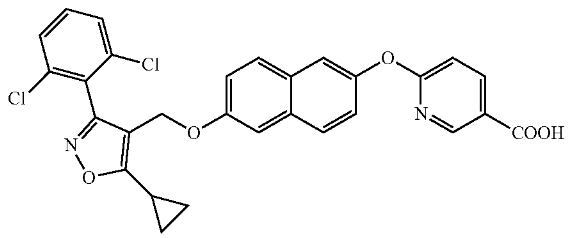

2

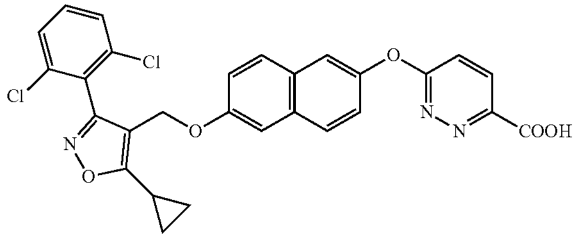

3

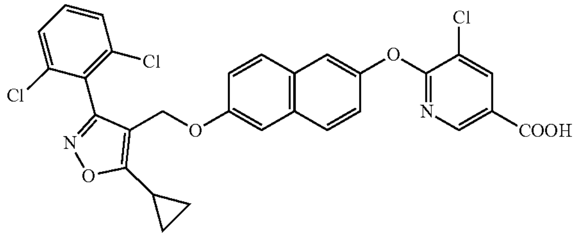

4

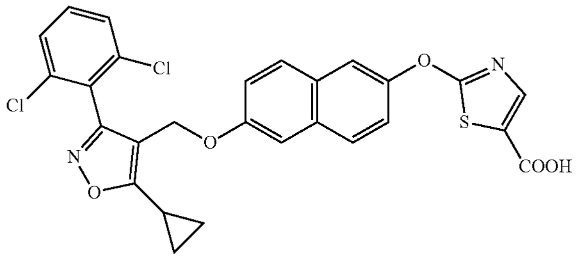

5

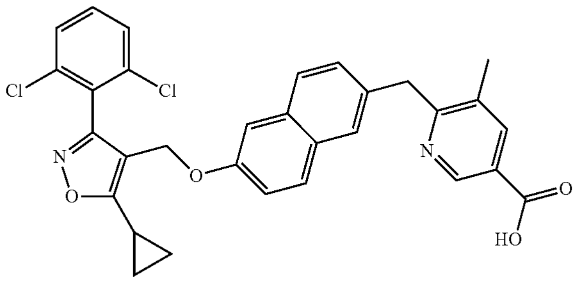

6

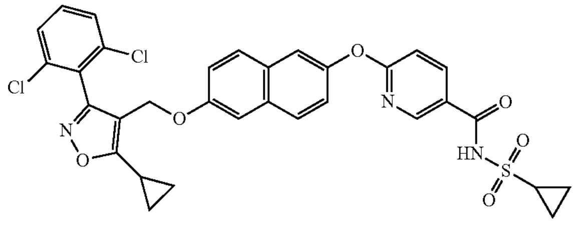

-continued
7
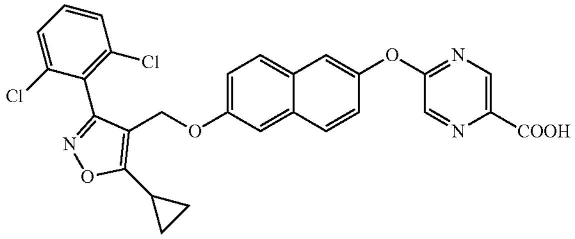
8
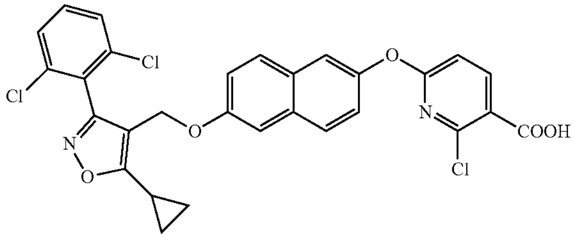
9
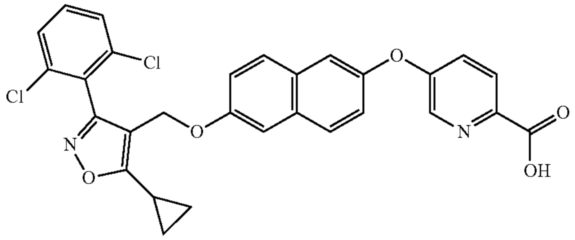
10
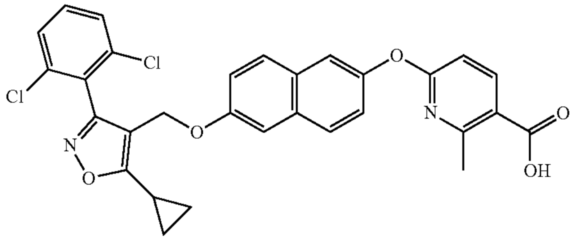
11
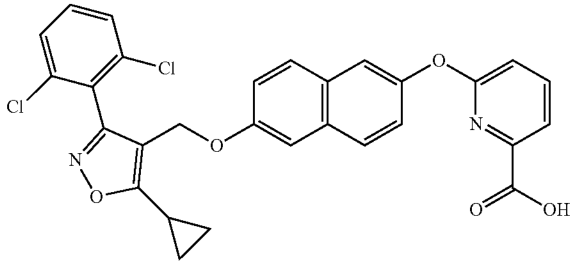
12
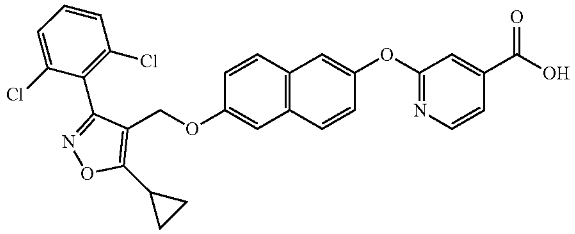
-continued
13
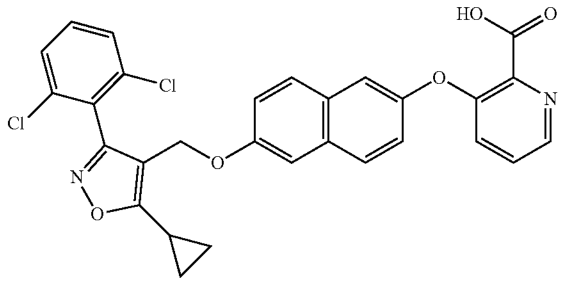
14
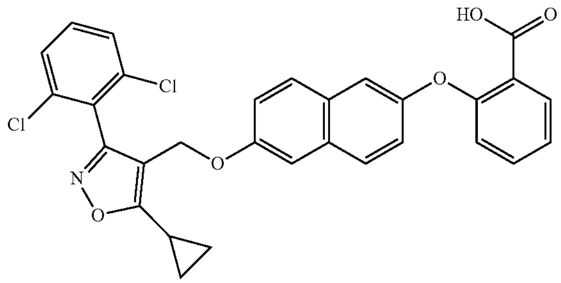
15
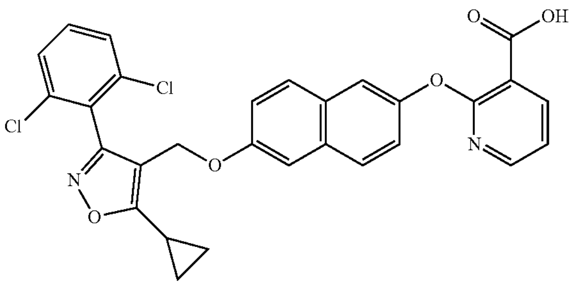
16
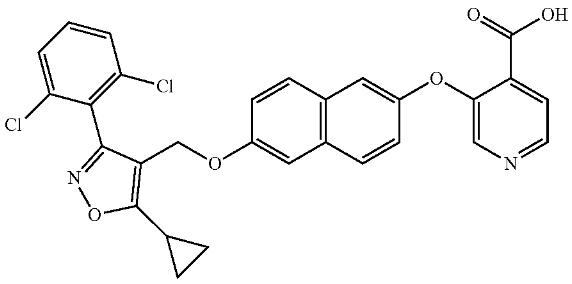
17
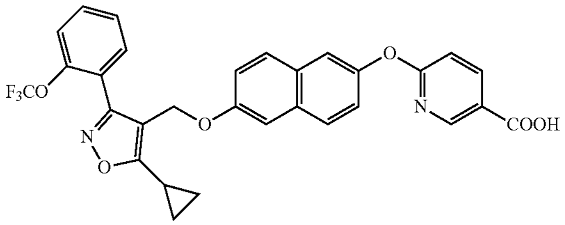

-continued
18
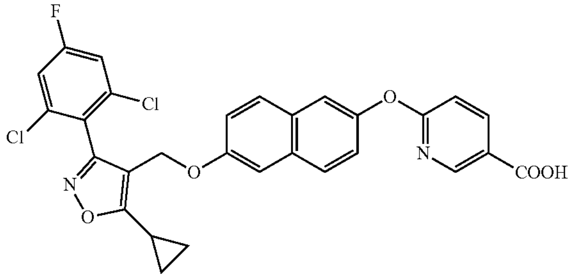
19
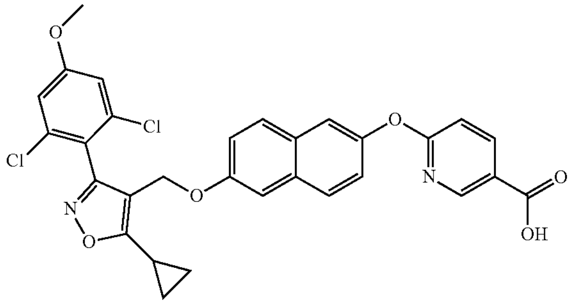
20
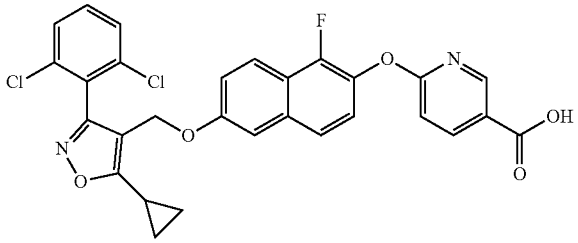
21
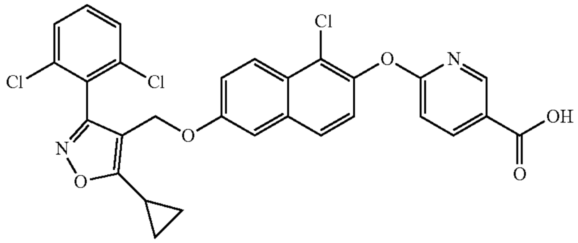
22
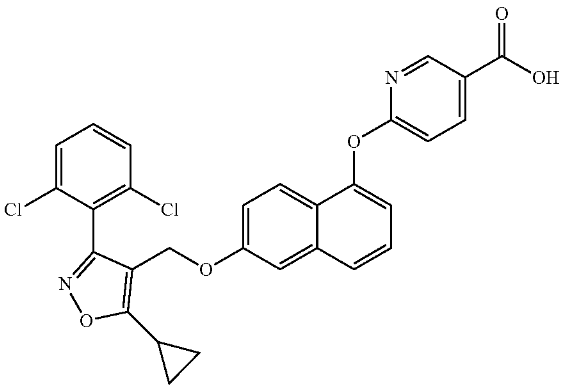
-continued
23
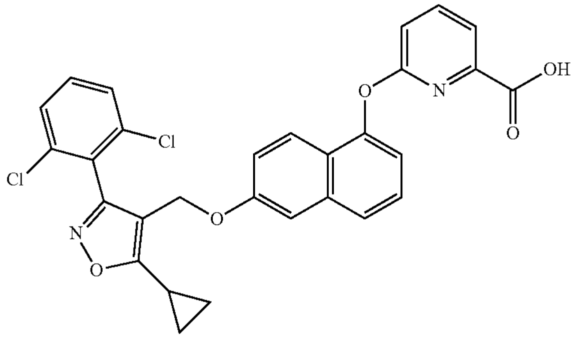
24
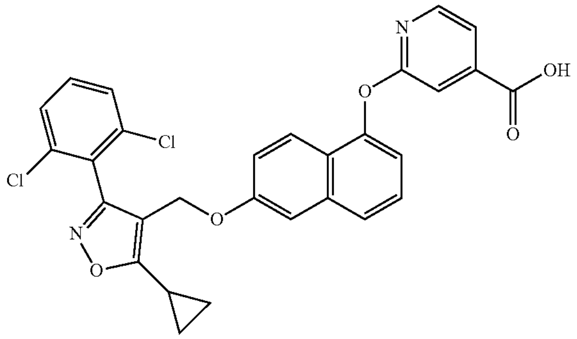
25
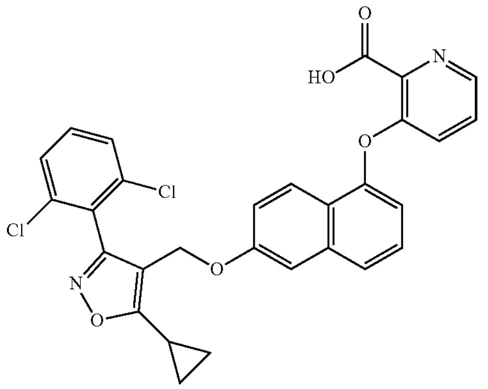
26
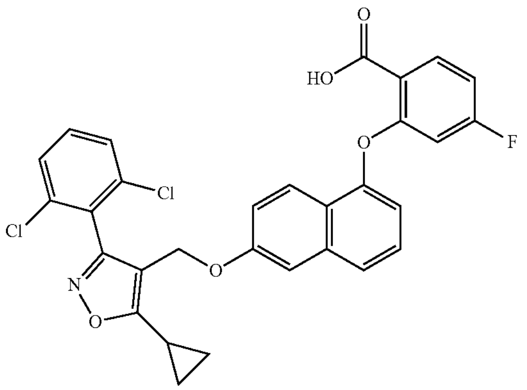

-continued
27
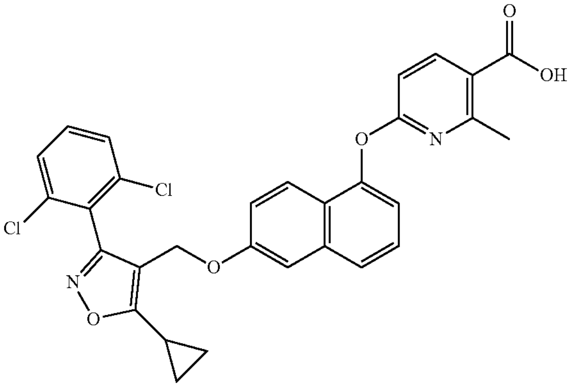
28
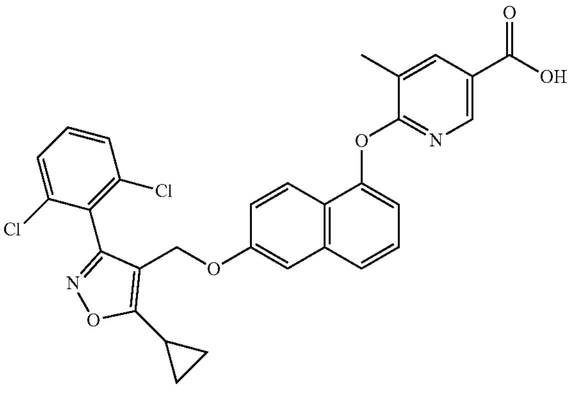
29
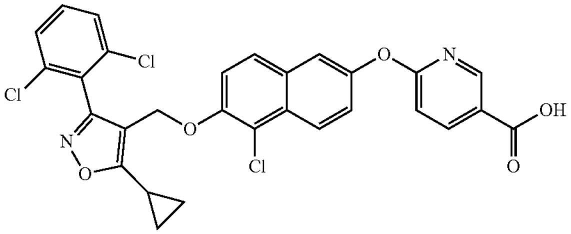
30
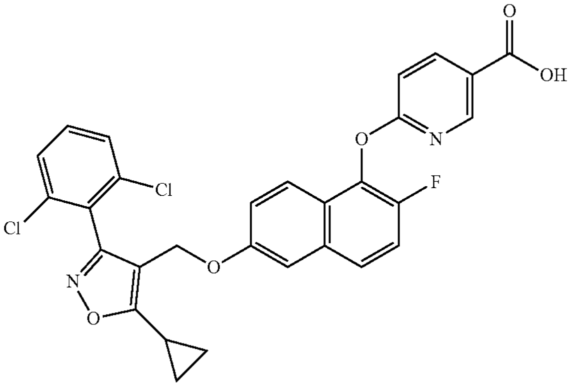
-continued
31
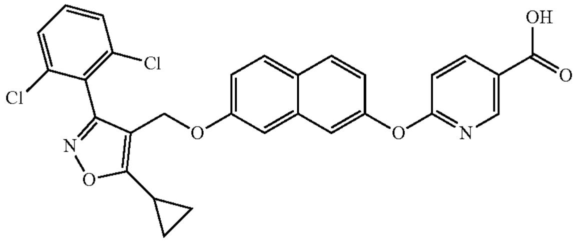
32
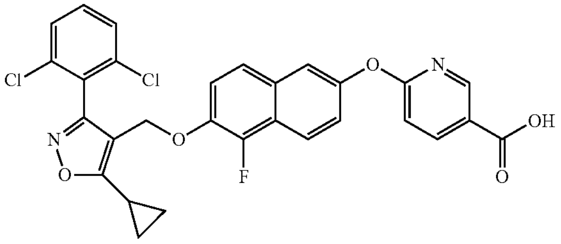
33
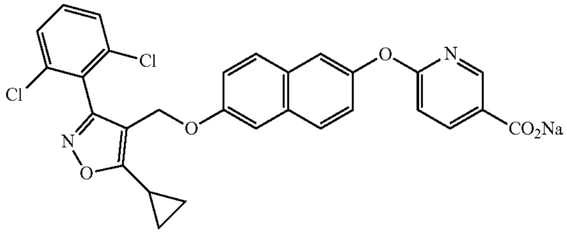
34
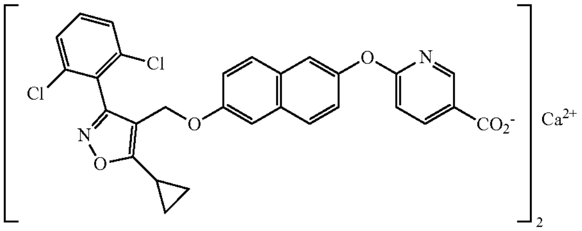
35
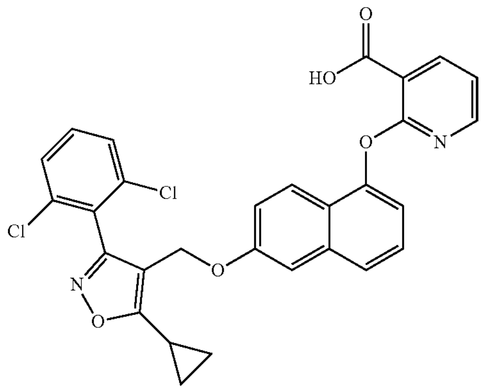

36
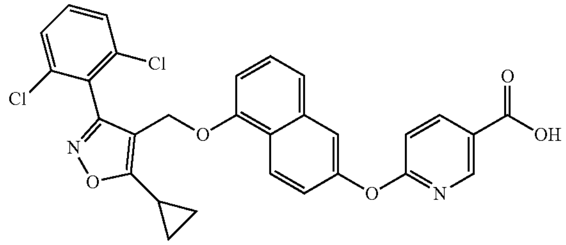
37
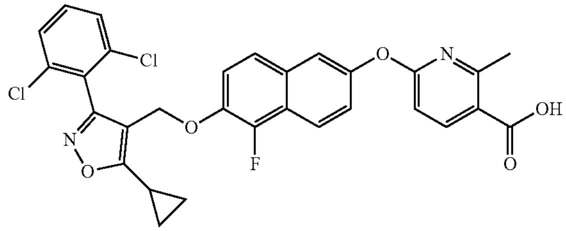
38
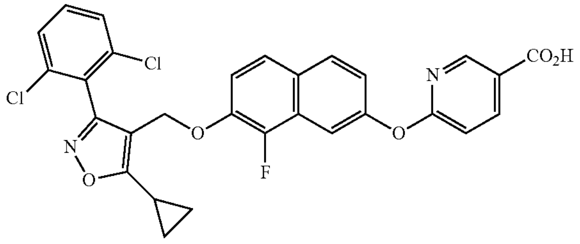
39
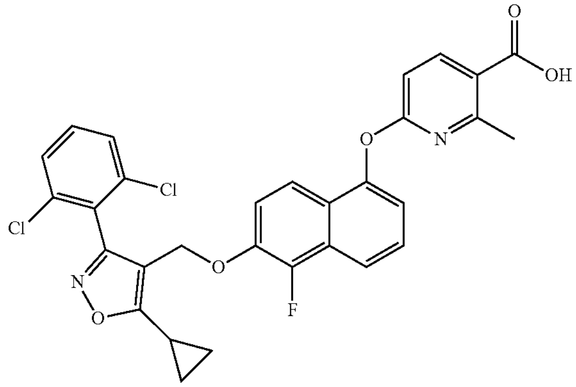
40
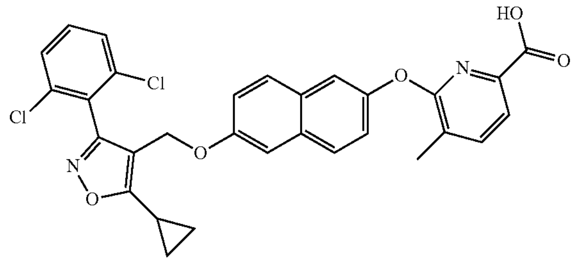
41
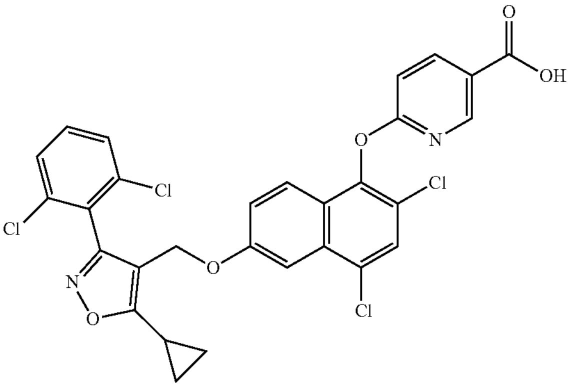
42
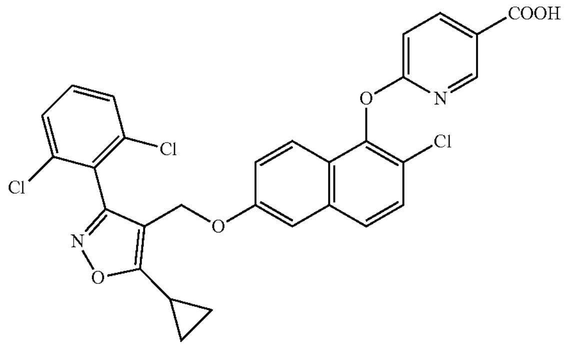
43
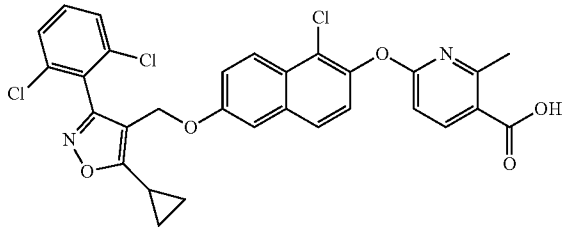
44
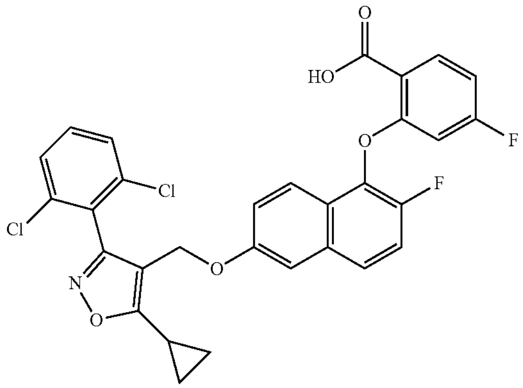

45
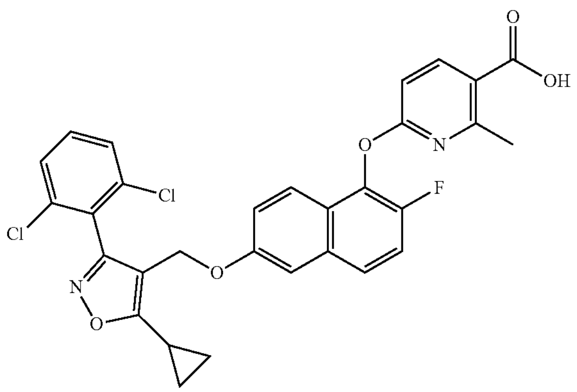
46
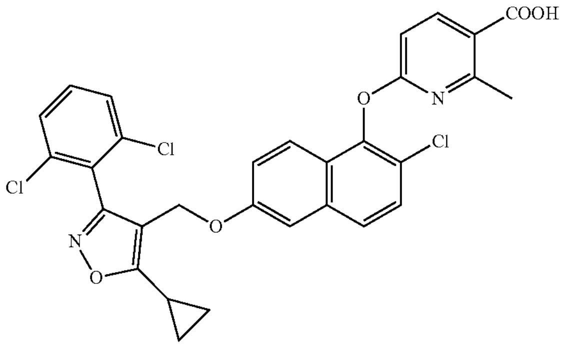
47
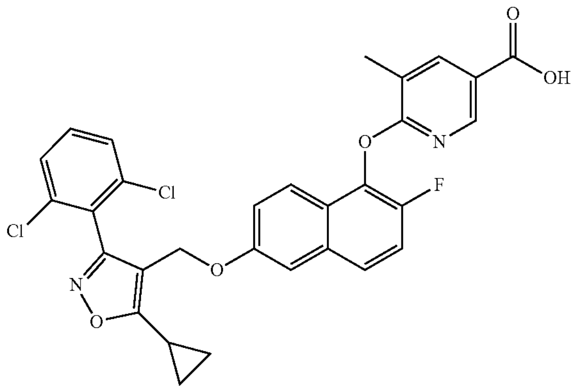
48
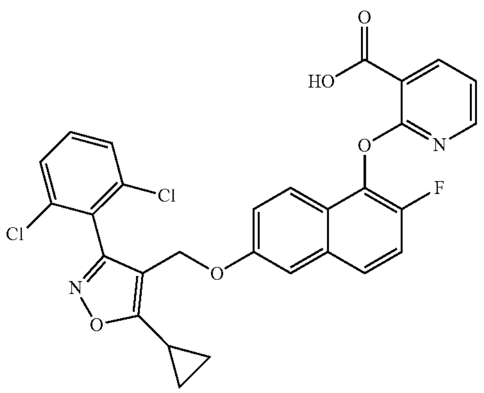
49
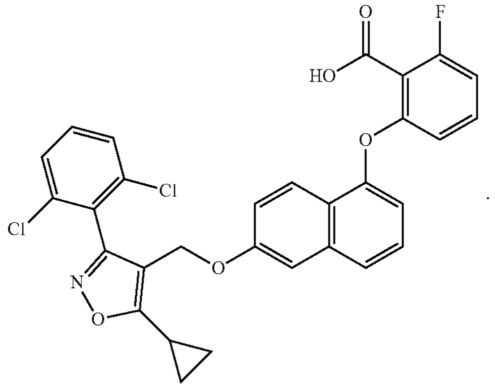
In another aspect, the present invention provides a method for preparing a compound of the formula (I), a pharmaceutically acceptable salt, an ester or a stereoisomer thereof, the method comprising four general routes (Route A, Route B, Route C, and Route D):
Route A
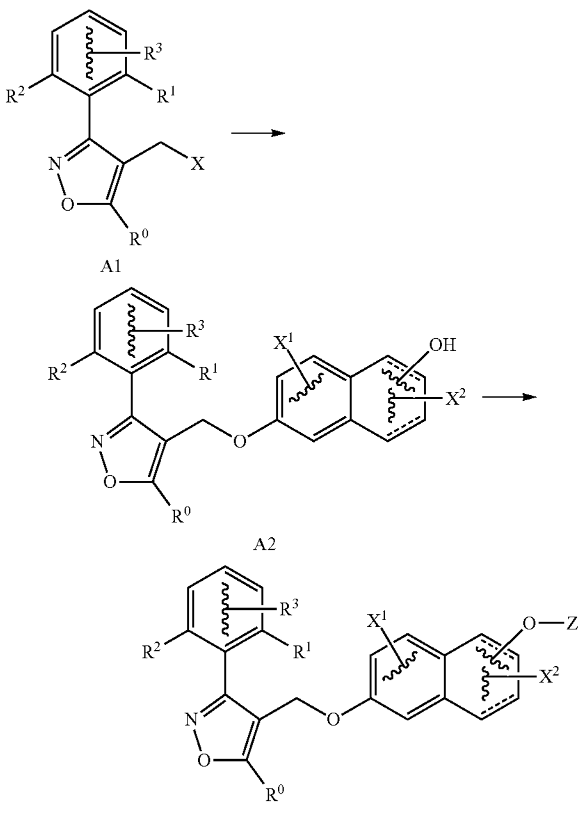
A1
A2
I Scheme B

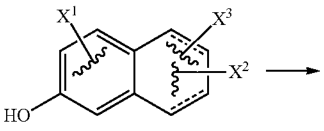

B1

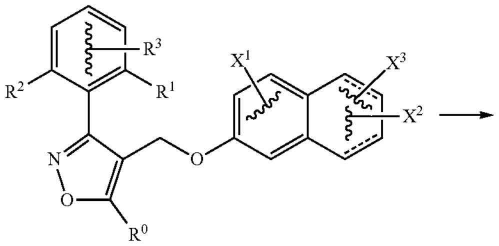

B2

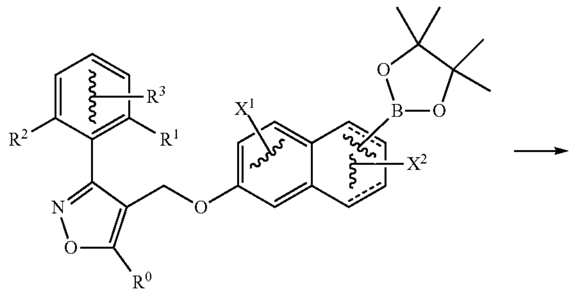

B3

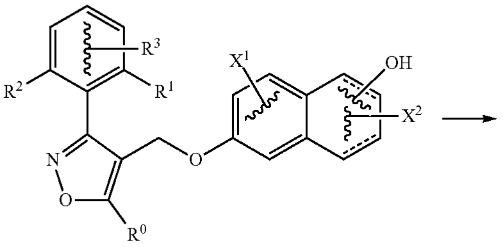

A2

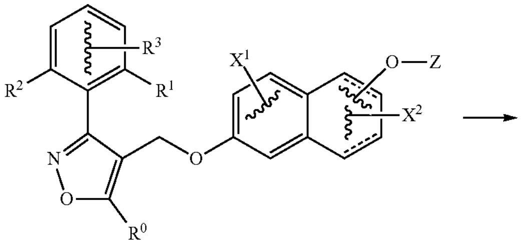

I

Scheme C

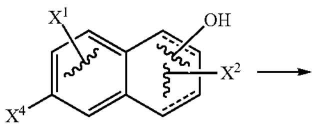

C1

-continued

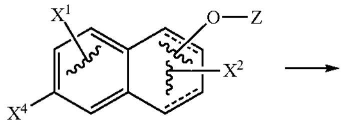

C2

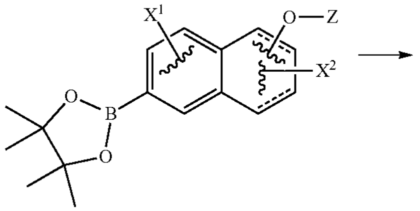

C3

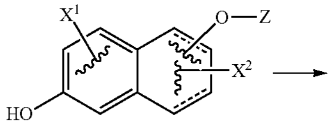

C4

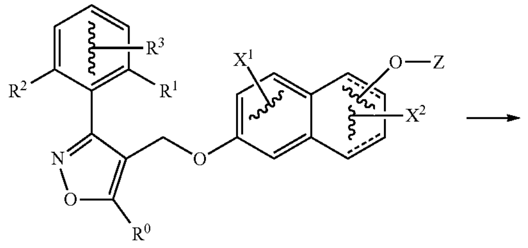

I

Route D

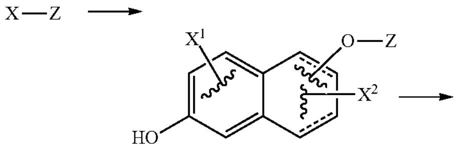

C4

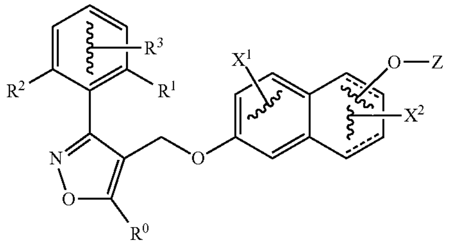

I

Hereinafter, the above-mentioned four general routes will be explained in detail.

Route A:

(a) reacting a halogenated compound of the formula (A1) with a dinaphthol to give an ether of the formula (A2). The reaction is carried out in a polar solvent with a base, preferably, in DMF or acetonitrile or the like with cesium carbonate or potassium carbonate or similar bases.

wherein:

X is a halogen;

$R^1$, $R^2$ and $R^3$ are independently selected from H, halogen, and unsubstituted or halogen substituted $C_{1-6}$ alkyl and unsubstituted or halogen substituted $C_{1-6}$ alkoxy, provided that at least one of $R^1$, $R^2$ and $R^3$ is not hydrogen, $R^0$ is selected from unsubstituted or halogen substituted $C_{1-6}$ alkyl, $C_{3-6}$ cycloalkyl, $C_{4-7}$ alkylcycloalkyl;

(b) reacting the resulting ether of the formula (A2) with a halogenated compound X—Z to give a compound of formula (I), wherein X is halogen, Z is a residue selected from 5-10 membered heteroaryl having one or more hetero atoms selected from N, O and S, wherein residue Z is substituted by $R^4$ and optionally further substituted by $R^5$;

wherein $R^4$ is selected from —COOH, —$CH_2COOH$, —$NHSO_2CF_3$, —$SO_2NH$—$C_{1-6}$ alkyl, —$SO_3H$, —$CONHSO_2$—$C_{1-6}$ alkyl, —$CONHSO_2$—$C_{3-6}$ cycloalkyl, —$CONHSO_2^{-}{}_{5-10}$ membered aryl and —$CONHSO_2$-5-10 membered aryl substituted by $C_{1-6}$ alkyl at the aryl, and $R^5$ is selected from H, $C_{1-6}$ alkyl, halogen and $C_{1-6}$ haloalkyl; optionally (c) reacting a compound of the formula (I) containing a —COOH substituent with an amide compound to give an amide compound of the formula (I) compound; and optionally (d) when Z is substituted with $R^4$ selected from —COOH and —$CH_2COOH$, ester precursors can be converted to free acids by hydrolysis using conditions well known to those skilled in the art, wherein the compound of the formula (I) is as hereinabove defined.

According to the preparation method as provided by the present invention, X is preferably bromine or iodine, and more preferably bromine.

Route B:

(a) reacting a halogenated compound of the formula (A1) with a substituted naphthol (B1) to give an ether of the formula (B2). The reaction is carried out in a polar solvent with a base, preferably, in DMF or acetonitrile or the like, with cesium carbonate or potassium carbonate or similar bases;

(b) Compound (B2) is converted to boronic ester of the formula (B3), preferably, under Pd-catalyzed conditions;

(c) Compound (B3) is converted to naphthol (A2) by oxidation, with oxidants such as $NaClO_2$ or $H_2O_2$;

(d) Compound (A2) is converted to Compound (I) using condition outlined in Route A, wherein $X^3$ is a halogen, preferably bromine or iodine, and more preferably bromine.

Route C:

(a) reacting a substituted naphthol (C1) with halogenated compound X—Z to give an ether of the formula (C2), wherein the reaction is carried out in a polar solvent with a base, preferably, in DMF or acetonitrile or the like, with cesium carbonate or potassium carbonate or similar bases;

(b) Compound (C2) is converted to boronic ester (C3), preferably, under Pd-catalyzed conditions;

(c) Compound (C3) is converted to naphthol (C4) by oxidation, with oxidants such as $NaClO_2$ or $H_2O_2$;

(d) Compound (C4) is converted to Compound (I) using similar condition outlined in Route A;

wherein $X^4$ is a halogen, preferably bromine or iodine, and more preferably bromine.

Route D:

(a) reacting a dinaphthol with halogenated compound X—Z to give an ether of the formula (C4) using similar condition outlined in Route C;

(b) Compound (C4) is converted to Compound (I) using similar condition outlined in Route C.

In still another aspect, the present invention provides a pharmaceutical composition comprising at least one compound of the formula (I), or a prodrug compound thereof, or a pharmaceutically acceptable salt, an ester or a stereoisomer thereof, and a pharmaceutically acceptable auxiliary material.

The pharmaceutical composition of the present invention may additionally comprise one or more other active compounds with an additional therapeutic benefit.

The pharmaceutical compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. The pharmaceutical compositions may be conveniently presented in unit dosage form and prepared by any of the methods well-known to those skilled in the art of pharmacy.

The compounds of the formula (I) and their pharmaceutically acceptable salts exhibit valuable pharmacological properties when tested in vitro binding assays and in cellular assays, and are therefore useful as pharmaceuticals. In particular, the compounds of the invention are agonists of FXR, and useful as pharmaceuticals to treat FXR-mediated conditions such as nonalcoholic fatty liver disease (NAFLD), nonalcoholic steatohepatitis (NASH), primary biliary cirrhosis (PBC), cholestasis liver disease, chronic liver disease, hepatitis C infection, alcoholic liver disease, hepatic fibrosis, primary sclerosing cholangitis (PSC), gallstones, bile duct atresia, lower urinary tract symptoms and benign prostatic hyperplasia (BPH), ureteral calculi, obesity, type 2 diabetes, atherosclerosis, liver damage caused by hypercholesterolemia and hyperlipidemia. The compounds of the invention are also useful for lowering total cholesterol, lowering LDL cholesterol, lowering VLDL cholesterol, raising HDL levels, and/or lowering triglyceride levels.

In yet another aspect, the invention provides a method to treat, ameliorate or prevent a FXR-mediated disorder in a subject suffering therefrom, comprising administering to the subject a therapeutically effective amount of a compound of the formula (I) a pharmaceutically acceptable salt, an analog of stable isotope, an ester or a stereoisomer thereof, or a pharmaceutical composition thereof, and optionally in combination with a second therapeutic agent. The present invention also provides for use of a compound of the formula (I) a pharmaceutically acceptable salt, an ester or a stereoisomer thereof and optionally in combination with a second therapeutic agent, in the manufacture of a medicament for treating a FXR-mediated disorder such as nonalcoholic fatty liver disease (NAFLD), nonalcoholic steatohepatitis (NASH), primary biliary cirrhosis (PBC), cholestasis liver tree, chronic liver disease, hepatitis C infection, alcoholic liver disease, hepatic fibrosis, primary sclerosing cholangitis (PSC), gallstones, bile duct atresia, lower urinary tract symptoms and benign prostatic hyperplasia (BPH), ureteral calculi, obesity, type 2 diabetes, atherosclerosis, atherosclerosis, liver damage caused by hypercholesterolemia or hyperlipidemia.

Unless specified otherwise, the term "compounds of the present invention" refers to the compounds of the formula (I), prodrugs thereof, salts of the compound and/or prodrugs, hydrates or solvates of the compounds, as well as all stereoisomers (including diastereoisomers and enantiomers), tautomers isotopically labeled compounds (including deuterium substitutions) and polymorphs of the compound.

Salts of the compounds of the present invention may be made by methods known to a person skilled in the art. For example, treatment of a compound of the present invention with an appropriate base or acid in an appropriate solvent will yield the corresponding salt.

Salts encompassed within the term "pharmaceutically acceptable salts" refer to non-toxic salts of the compounds of this invention. Preferred are alkaline salts of the carboxylic acid, such as sodium, potassium, lithium, calcium, magnesium, aluminium, zinc, N,N'-dibenzylethylenediamine, chloroprocaine, choline, diethanolamine, ethylenediamine, N-methylglucamine and procaine salts. Other salts, which are not pharmaceutically acceptable, may be useful in the preparation of compounds of this invention and these should be considered to form a further aspect of the invention.

All starting materials, reagents, acids, bases, solvents and catalysts utilized to synthesize the compounds of the present invention are either commercially available or can be produced by organic synthesis methods known to one of ordinary skill in the art. All methods described herein can be performed in any suitable order unless otherwise indicated herein or otherwise clearly contradicted by context. The use of any and all examples, or exemplary language (e.g. such as) provided herein is intended merely to better illuminate the invention and does not pose a limitation on the scope of the invention otherwise claimed.

BRIEF DESCRIPTION OF THE DRAWINGS

In order to explain the embodiments of the present invention or the technical solutions in the prior art more clearly, drawings required for the description of the embodiments of the present invention will be briefly described below. Obviously, the drawings in the following description are only some embodiments of the present invention.

BEST MODE FOR CARRYING OUT THE INVENTION

Figure 1:
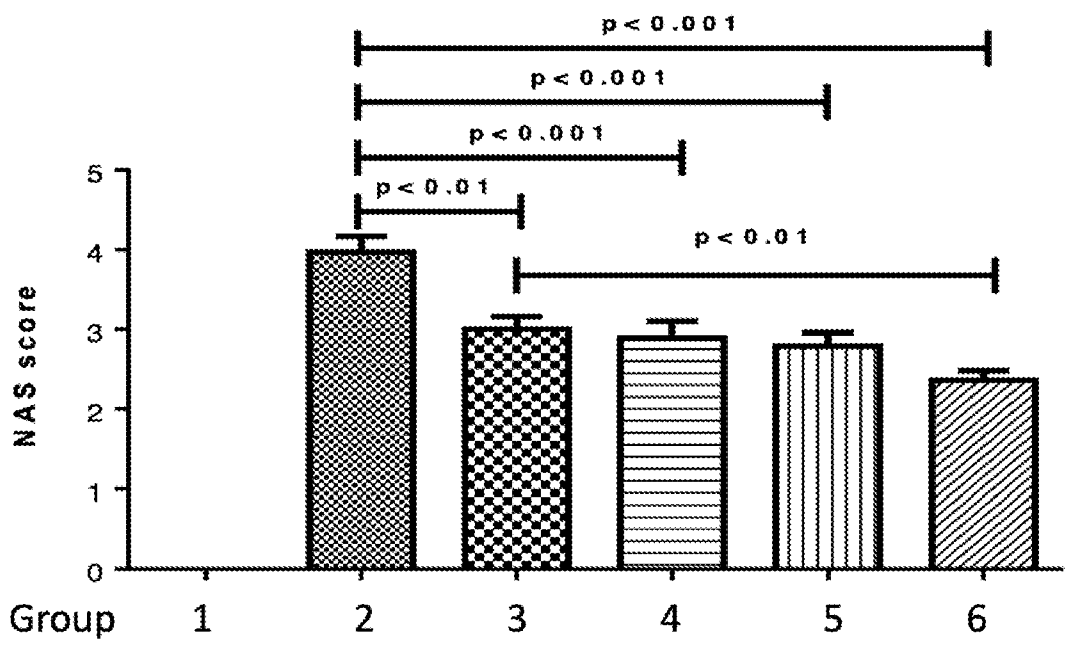
FIG. 1 shows reduction of NAS score after Compound 1 treatment in streptozocin (STZ)+diethylnitrosamine (DEN)+high fat diet (HFD) mice disease model.

The present invention will be further illustrated with reference to the examples below. It is necessary to state that, the examples below are only for illustration, but not for limitation of the present invention. Various alterations that are made by a person skilled in the art in accordance with teaching from the present invention should be within the scope claimed by the claims of the present invention.

Example 1

Preparation of 6-((6-((5-cyclopropyl-3-(2,6-dichlorophenyl)isoxazol-4-yl) methoxy)naphthalen-2-yl) oxy)nicotinic acid (Compound 1)

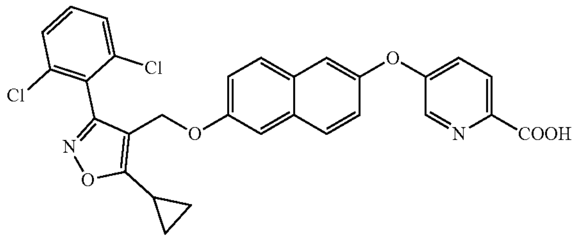 [SMILES: O=C(O)c1ccc(Oc2ccc3cc(OCc4c(-c5c(Cl)cccc5Cl)noc4C4CC4)ccc3c2)cn1]

(a) Referring to the following reaction equation (Route A), Compound 1A-1 (1.0 g, 2.88 mmol, 1 eq.), Compound 1A-2 (0.46 g, 2.88 mmol, 1 eq.) and cesium carbonate (1.88 g, 5.76 mmol, 2 eq.) were dissolved in DMF (10 ml). The reaction was carried out at 65° C. for 2 h. After cooling, 10 ml water and 10 ml EA (ethyl acetate) were added for extraction, and the organic phase was washed with water and concentrated to dryness to give Compound 1A, 6-((5-cyclopropyl-3-(2,6-dichlorophenyl)isoxazol-4-yl)methoxy)naphthalen-2-ol, 0.8 g, yield: 65.0%. LCMS (ESI): calculated for $C_{23}H_{17}C_{12}NO_3$; $[M+H]^+$: 426.1, found: 426.1.

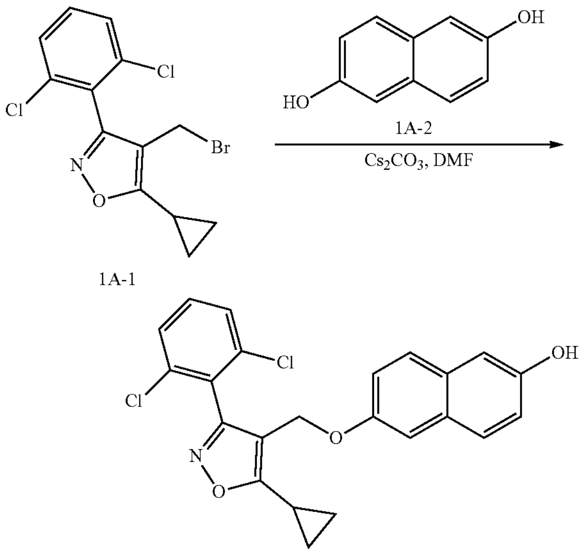

1A-1

1A (b) Referring to the following reaction equation, Compound 1A (0.2 g, 0.47 mmol, 1 eq.), 6-bromonicotinic acid methyl ester (0.1 g, 0.47 mmol, 1 eq.) and cesium carbonate (0.306 g, 0.94 mmol, 2 eq.) were dissolved in DMF (10 ml). The reaction was carried out at 65° C. for 2 h. After cooling, 10 ml water and 10 ml EA were added for extraction, and the organic phase was washed with water and concentrated to dryness to give Compound 1B, methyl 6((6((5-cyclopropyl-3-(2,6-dichlorophenyl)isoxazol-4-yl)methoxy)naphthalene-2-yl)oxy)nicotinate, 0.21 g, yield: 80.0%. LCMS (ESI): calculated for $C_{30}H_{22}C_{12}N_2O_5$; $[M+H]^+$: 561.1, found: 561.1.

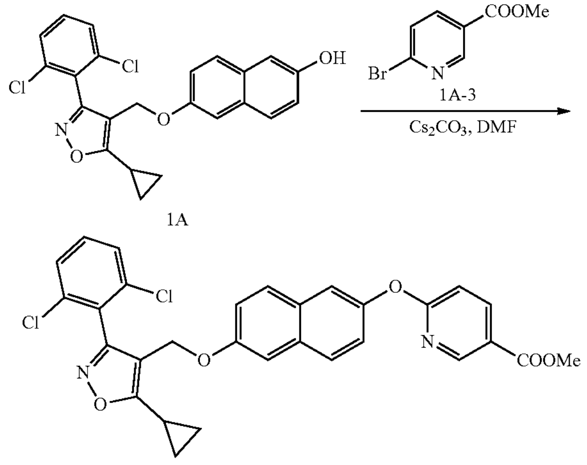

1A

1B (c) Referring to the following reaction equation, compound 1B (100 mg) was dissolved in methanol (2 ml), then 10% NaOH aqueous solution (1 ml) was added, the temperature was raised to 60° C., and the reaction was carried out for 1 h. The pH of the reaction solution was adjusted to 2 to 4 by adding 1N HCl solution, and 10 ml EA (ethyl acetate) was added for extraction. The organic phase was concentrated and purified on a column (PE/EA/AcOH=1/1/01 elution, wherein PE is petroleum ether) to give the title compound 1 (36 mg, yield: 37.0%).

$^1$H NMR (400 MHz, DMSO-$d_6$) δ 8.57 (s, 1H), 8.23 (d, J=7.2 Hz, 1H), 7.74 (dd, J=2.0, 8.8 Hz, 2H), 7.60 (d, J=7.6 Hz, 2H), 7.56 (s, 1H), 7.51 (dd, J=8.8, 7.2 Hz, 1H), 7.33 (s, 1H), 7.26 (d, J=8.8 Hz, 1H), 7.02 (d, J=8.0 Hz, 1H), 6.93 (d, J=6.4 Hz, 1H), 4.98 (s, 2H), 2.57-2.50 (m, 1H), 1.19-1.11 (m, 4H). LCMS (ESI): calculated for $C_{29}H_{20}Cl_2N_2O_5$; $[M+H]^+$: 547.1, found: 547.1. $^{13}$C NMR (400 MHz, DMSO-$d_6$) δ7.79, 8.87, 8.87, 59.31, 107.74, 110.05, 110.97, 117.64, 119.43, 122.52, 127.55, 128.64, 128.89, 128.89, 129.18, 129.67, 131.73, 131.79, 132.94, 135.10, 135.10, 141.20, 149.11, 150.73, 155.79, 159.68, 163.82, 167.81, 172.61. IR ($cm^{-1}$): major stretches at 1591.94 (C═O stretch), 1412.27, 1556.70 (C—C stretch), 1364.37, 1389.89 (C—H deformation), 1218.41, 1250.94 (C═N stretch), 791.88 (C—Cl stretch).

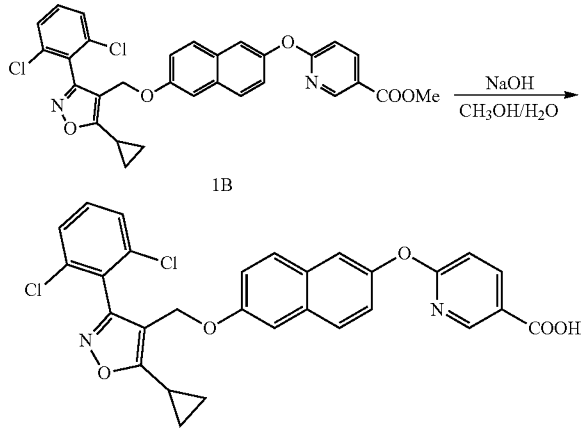

1B

1

Example 2

Preparation of 6-((6-((5-cyclopropyl-3-(2,6-dichlorophenyl)isoxazol-4-yl) methoxy)naphthalen-2-yl) oxy)pyridazine-3-carboxylic acid (Compound 2)

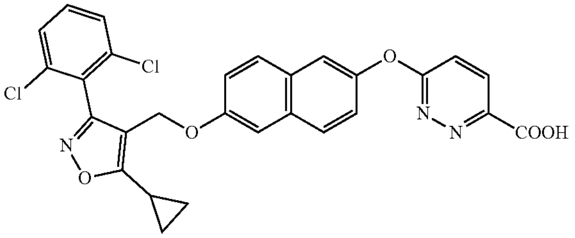 [SMILES: O=C(O)c1ccc(Oc2ccc3cc(OCc4c(-c5c(Cl)cccc5Cl)noc4C4CC4)ccc3c2)nn1]

Following the procedure of Example 1, the title Compound 2 was obtained by substituting methyl 6-bromopyridazine-3-carboxylate for 6-bromonicotinic acid methyl ester.

$^1$H NMR (400 MHz, DMSO-$d_6$) δ 8.52 (s, 1H), 8.25 (d, J=7.2 Hz, 1H), 7.74 (dd, J=2.0, 8.8 Hz, 2H), 7.61 (d, J=7.6 Hz, 2H), 7.52 (dd, J=8.8, 7.2 Hz, 1H), 7.34 (s, 1H), 7.26 (d, J=8.8 Hz, 1H), 7.00 (d, J=8.0 Hz, 1H), 6.95 (d, J=6.4 Hz, 1H), 4.98 (s, 2H), 2.59-2.50 (m, 1H), 1.21-1.11 (m, 4H). LCMS (ESI): calculated for $C_{28}H_{19}Cl_2N_3O_5$; $[M+H]^+$: 548.1, found: 548.1.

Example 3

Preparation of 5-chloro-6-((6-((5-cyclopropyl-3-(2,6-dichlorophenyl) isoxazol-4-yl)methoxy)naphthalen-2-yl)oxy)nicotinic acid (Compound 3)

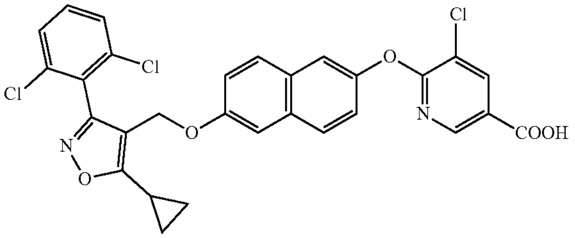 [SMILES: O=C(O)c1cnc(Oc2ccc3cc(OCc4c(-c5c(Cl)cccc5Cl)noc4C4CC4)ccc3c2)c(Cl)c1]

Following the procedure of Example 1, the title Compound 3 was obtained by substituting methyl 5,6-dichloronicotinate for 6-bromonicotinic acid methyl ester.

$^1$H NMR (400 MHz, DMSO-$d_6$) δ 8.60 (s, 1H), 7.73 (dd, J=2.0, 8.8 Hz, 2H), 7.59 (d, J=7.6 Hz, 2H), 7.51 (dd, J=8.8, 7.2 Hz, 1H), 7.33 (s, 1H), 7.26 (d, J=8.8 Hz, 1H), 7.01 (d, J=8.0 Hz, 1H), 6.95 (d, J=6.4 Hz, 1H), 5.00 (s, 2H), 1.26-1.12 (m, 5H). LCMS (ESI): calculated for $C_{29}H_{19}Cl_3N_2O_5$; $[M+H]^+$: 581.0, found: 581.0.

Example 4

Preparation of 2-((6-((5-cyclopropyl-3-(2,6-dichlorophenyl)isoxazol-4-yl) methoxy)naphthalen-2-yl) oxy)thiazole-5-carboxylic acid (Compound 4)

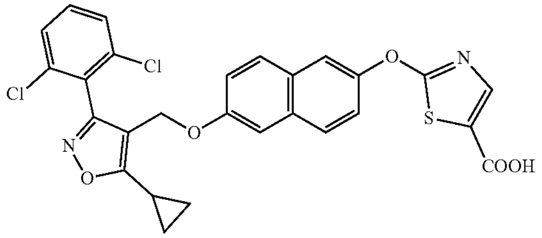 [SMILES: O=C(O)c1cnc(Oc2ccc3cc(OCc4c(-c5c(Cl)cccc5Cl)noc4C4CC4)ccc3c2)s1]

Following the procedure of Example 1, the title Compound 4 was obtained by substituting methyl 2-bromothiazole-5-carboxylate for 6-bromonicotinic acid methyl ester.

$^1$H NMR (400 MHz, DMSO-$d_6$) δ 8.80 (s, 1H), 7.69 (dd, J=2.0, 8.8 Hz, 2H), 7.59 (d, J=7.6 Hz, 2H), 7.53 (dd, J=8.8, 7.2 Hz, 1H), 7.32 (s, 1H), 7.26 (d, J=8.8 Hz, 1H), 7.01 (d, J=8.0 Hz, 1H), 6.99 (d, J=6.4 Hz, 1H), 5.00 (s, 2H), 1.25-1.12 (m, 5H). LCMS (ESI): calculated for $C_{27}H_{18}Cl_2N_2O_5S$; $[M+H]^+$: 553.0, found: 553.0.

Example 5

Preparation of 6-((6-((5-cyclopropyl-3-(2,6-dichlorophenyl)isoxazol-4-yl) methoxy)naphthalen-2-yl) oxy)-5-methylnicotinic acid (Compound 5)

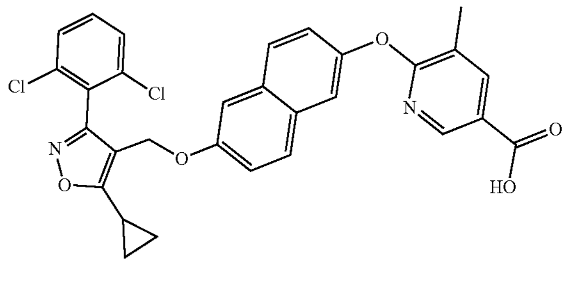 [SMILES: Cc1cc(C(=O)O)cnc1Oc1ccc2cc(OCc3c(-c4c(Cl)cccc4Cl)noc3C3CC3)ccc2c1]

Following the procedure of Example 1, the title Compound 5 was obtained by substituting methyl 6-bromo-5-methylnicotinate for 6-bromonicotinic acid methyl ester.

$^1$H NMR (400 MHz, DMSO-$d_6$) δ 12.78 (s, 1H), 8.35 (d, J=1.5 Hz, 1H), 8.12-7.90 (m, 1H), 7.72-7.61 (m, 2H), 7.54 (s, 3H), 7.28 (m, 2H), 7.15-7.10 (m, 1H), 7.07 (dd, J=7.5, 1.5 Hz, 1H), 6.95 (dd, J=7.6, 1.6 Hz, 1H), 5.41 (s, 2H), 2.99-2.70 (m, 1H), 2.28 (s, 3H), 2.12-1.56 (m, 4H). LCMS (ESI): calculated for $C_{30}H_{22}Cl_2N_2O_5$; $[M+H]^+$: 561.1, found: 561.1.

Example 6

Preparation of 6((6((5-cyclopropyl-3-(2,6-dichlorophenyl)isoxazol-4-yl) methoxy)naphthalen-2-yl) oxy)-N-(cyclopropylsulfonyl)nicotinamide (Compound 6)

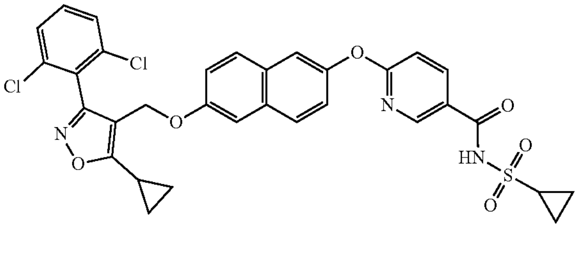 [SMILES: O=C(NS(=O)(=O)C1CC1)c1ccc(Oc2ccc3cc(OCc4c(-c5c(Cl)cccc5Cl)noc4C4CC4)ccc3c2)nc1]

Compound 1 (70 mg) as prepared in Example 1 and cyclopropylsulfonamide (23 mg) were dissolved in 2 ml DCM (dichloromethane), then 40 mg EDCI (1-(3-dimethylaminopropyl)-3-ethylcarbodiimide hydrochloride) and 26 mg DMAP (dimethylaminopyridine) were added. After completion of the reaction, 10 ml DCM and 10 ml water was added for extraction. The organic phase was washed with water and concentrated to dryness. The crude product is purified by column (PE/EA/AcOH=2/1/0.01) to give the title Compound 6 (8 mg, yield: 9.6%).

$^1$H NMR (400 MHz, DMSO-$d_6$) δ 8.63 (d, J=1.5 Hz, 1H), 8.30 (dd, J=7.5, 1.5 Hz, 1H), 7.79 (d, J=8.0 Hz, 1H), 7.73 (d, J=8.0 Hz, 1H), 7.59-7.62 (m, 3H), 7.49-7.53 (m, 1H), 7.35 (s, 1H), 7.26-7.29 (m, 1H), 7.10 (d, J=8.0 Hz, 1H), 6.93-6.96 (m, 1H), 4.98 (s, 2H), 1.02-1.20 (m, 10H). LCMS (ESI): calculated for $C_{32}H_{25}Cl_2N_3O_6S$; $[M+H]^+$: 650.1, found: 650.1.

Example 7

Preparation of 5-((6-((5-cyclopropyl-3-(2,6-dichlorophenyl)isoxazol-4-yl) methoxy)naphthalen-2-yl) oxy)pyrazine-2-carboxylic acid (Compound 7)

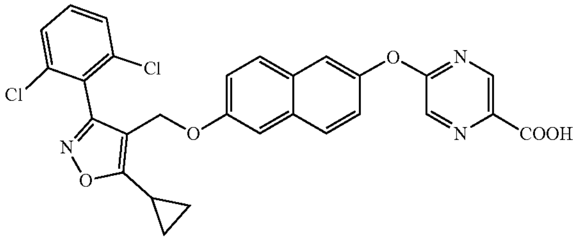 [SMILES: O=C(O)c1cnc(Oc2ccc3cc(OCc4c(-c5c(Cl)cccc5Cl)noc4C4CC4)ccc3c2)cn1]

Following the procedure of Example 1, the title Compound 7 was obtained by substituting methyl 5-chloropyridine-2-carboxylate for 6-bromonicotinic acid methyl ester.

$^1$H NMR (400 MHz, DMSO-$d_6$) δ 8.63 (s, 1H), 8.30 (s, 1H), 7.79 (d, J=8.8 Hz, 1H), 7.72 (d, J=9.2 Hz, 1H), 7.58-7.63 (m, 4H), 7.49-7.53 (m, 1H), 7.34 (d, J=2.0 Hz, 1H), 6.94 (d, J=9.2 Hz, 1H), 4.98 (s, 2H), 1.11-1.22 (m, 5H). LCMS (ESI): calculated for $C_{28}H_{19}Cl_2N_3O_5$; $[M+H]^+$: 548.1, found: 548.1.

Example 8

Preparation of 2-chloro-6-((6-((5-cyclopropyl-3-(2,6-dichlorophenyl) isoxazol-4-yl)methoxy)naphthalen-2-yl)oxy)nicotinic acid (Compound 8)

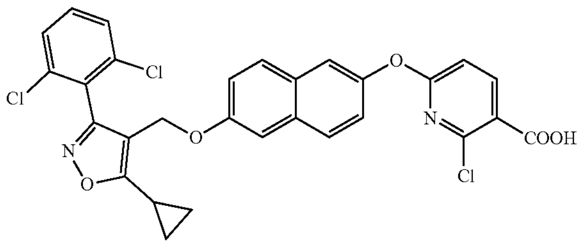 [SMILES: O=C(O)c1ccc(Oc2ccc3cc(OCc4c(-c5c(Cl)cccc5Cl)noc4C4CC4)ccc3c2)nc1Cl]

Following the procedure of Example 1, the title Compound 8 was obtained by substituting methyl 2,6-dichloronicotinate for 6-bromonicotinic acid methyl ester.

$^1$H NMR (400 MHz, DMSO-$d_6$) δ 7.98 (br s, 1H), 7.70-7.79 (m, 2H), 7.60 (d, J=8.0 Hz, 2H), 7.47-7.55 (m, 2H), 7.18-7.33 (m, 2H), 6.90-6.95 (m, 2H), 4.98 (s, 2H), 1.11-1.22 (m, 5H). LCMS (ESI): calculated for $C_{29}H_{19}Cl_3N_2O_5$; $[M+H]^+$: 581.0, found: 581.0.

Example 9

Preparation of 5-((6-((5-cyclopropyl-3-(2,6-dichlorophenyl)isoxazol-4-yl)methoxy)naphthalen-2-yl) oxy)picolinic acid (Compound 9)

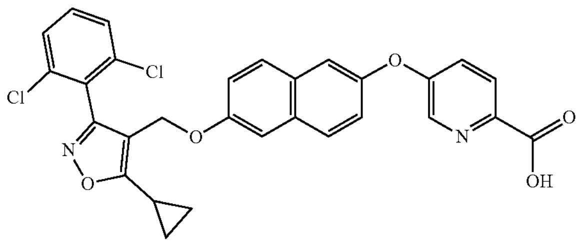 [SMILES: O=C(O)c1ccc(Oc2ccc3cc(OCc4c(-c5c(Cl)cccc5Cl)noc4C4CC4)ccc3c2)cn1]

Following the procedure of Example 1, the title Compound 9 was obtained by substituting methyl 5-bromopicolinate for 6-bromonicotinic acid methyl ester.

$^1$H NMR (400 MHz, DMSO-$d_6$) δ 8.46 (d, J=3.1 Hz, 1H), 8.03 (d, J=8.7 Hz, 1H), 7.83 (d, J=8.9 Hz, 1H), 7.72 (d, J=9.1 Hz, 1H), 7.55 (dt, J=28.7, 8.3 Hz, 4H), 7.43 (d, J=8.6 Hz, 1H), 7.39-7.24 (m, 2H), 6.95 (d, J=8.9 Hz, 1H), 4.98 (s, 2H), 1.23-1.02 (m, 5H). LCMS (ESI): calculated for $C_{29}H_{20}Cl_2N_2O_5$; $[M+H]^+$: 547.1, found: 547.1.

Example 10

Preparation of 6-((6-((5-cyclopropyl-3-(2,6-dichlorophenyl)isoxazol-4-yl)methoxy)naphthalen-2-yl) oxy)-2-methylnicotinic acid (Compound 10)

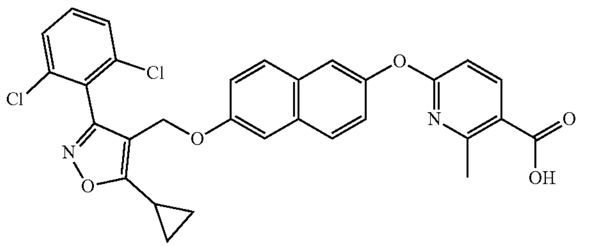 [SMILES: Cc1nc(Oc2ccc3cc(OCc4c(-c5c(Cl)cccc5Cl)noc4C4CC4)ccc3c2)ccc1C(=O)O]

Following the procedure of Example 1, the title Compound 10 was obtained by substituting methyl 6-chloro-2-methylnicotinate for 6-bromonicotinic acid methyl ester.

$^1$H NMR (400 MHz, DMSO-$d_6$) δ 8.21 (d, J=8.6 Hz, 1H), 7.78 (d, J=8.9 Hz, 1H), 7.72 (d, J=9.0 Hz, 1H), 7.62-7.55 (m, 3H), 7.51 (dd, J=9.0, 7.1 Hz, 1H), 7.34 (d, J=2.5 Hz, 1H), 7.27 (dd, J=8.8, 2.4 Hz, 1H), 6.94 (dd, J=8.9, 2.5 Hz, 1H), 6.85 (d, J=8.6 Hz, 1H), 4.98 (s, 2H), 2.52 (s, 3H), 1.24-1.07 (m, 5H). LCMS (ESI): calculated for $C_{30}H_{22}Cl_2N_2O_5$; $[M+H]^+$: 561.1, found: 561.1.

Example 11

Preparation of 6-((6-((5-cyclopropyl-3-(2,6-dichlorophenyl)isoxazol-4-yl)methoxy)naphthalen-2-yl) oxy)picolinic acid (Compound 11)

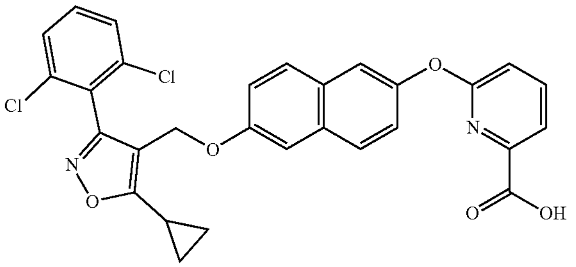 [SMILES: O=C(O)c1cccc(Oc2ccc3cc(OCc4c(-c5c(Cl)cccc5Cl)noc4C4CC4)ccc3c2)n1]

Following the procedure of Example 1, the title Compound 11 was obtained by substituting methyl 2,6-dichloronicotinate for 6-bromonicotinic acid methyl ester.

$^1$H NMR (400 MHz, DMSO-$d_6$) δ 7.99 (t, J=7.9 Hz, 1H), 7.77 (d, J=8.1 Hz, 2H), 7.71 (d, J=8.9 Hz, 1H), 7.63-7.45 (m, 4H), 7.33 (s, 1H), 7.29 (d, J=9.0 Hz, 1H), 7.22 (d, J=8.2 Hz, 1H), 6.94 (d, J=9.0 Hz, 1H), 4.98 (s, 2H), 1.26-1.01 (m, 5H). LCMS (ESI): calculated for $C_{29}H_{20}Cl_2N_2O_5$; $[M+H]^+$: 547.1, found: 547.1.

Example 12

Preparation of 2-((6-((5-cyclopropyl-3-(2,6-dichlorophenyl)isoxazol-4-yl)methoxy)naphthalen-2-yl)oxy)isonicotinic acid (Compound 12)

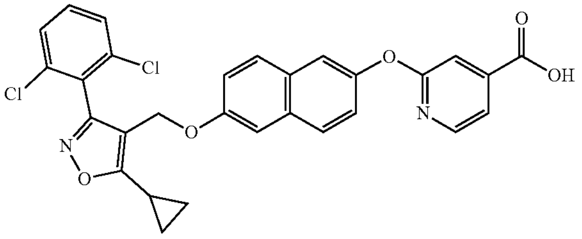 [SMILES: O=C(O)c1ccnc(Oc2ccc3cc(OCc4c(-c5c(Cl)cccc5Cl)noc4C4CC4)ccc3c2)c1]

Following the procedure of Example 1, the title Compound 12 was obtained by substituting methyl 2-fluoroisonicotinate for 6-bromonicotinic acid methyl ester.

$^1$H NMR (400 MHz, DMSO-$d_6$) δ 8.29 (d, J=5.1 Hz, 1H), 7.78 (d, J=8.8 Hz, 1H), 7.59 (t, J=7.7 Hz, 3H), 7.52 (m, 2H), 7.34 (s, 2H), 7.29 (s, 1H), 4.98 (s, 2H), 1.31-1.06 (m, 5H). LCMS (ESI): calculated for $C_{29}H_{20}Cl_2N_2O_5$; $[M+H]^+$: 547.1, found: 547.1.

Example 13

Preparation of 3-((6-((5-cyclopropyl-3-(2,6-dichlorophenyl)isoxazol-4-yl)methoxy)naphthalen-2-yl)oxy)picolinic acid (Compound 13)

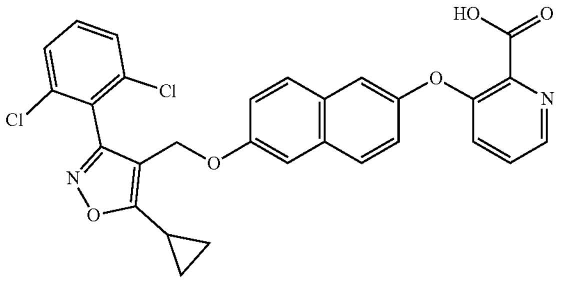 [SMILES: O=C(O)c1ncccc1Oc1ccc2cc(OCc3c(-c4c(Cl)cccc4Cl)noc3C3CC3)ccc2c1]

Following the procedure of Example 1, the title Compound 13 was obtained by substituting methyl 3-fluoropicolinate for 6-bromonicotinic acid methyl ester.

$^1$H NMR (400 MHz, DMSO-$d_6$) δ 8.39 (d, J=4.4 Hz, 1H), 7.77 (d, J=9.0 Hz, 1H), 7.66 (d, J=9.2 Hz, 1H), 7.59 (d, J=8.1 Hz, 2H), 7.54-7.43 (m, 3H), 7.30 (d, J=2.8 Hz, 2H), 7.26-7.16 (m, 1H), 6.95-6.85 (m, 1H), 4.95 (s, 2H), 1.24-1.06 (m, 5H). LCMS (ESI): calculated for $C_{29}H_{20}Cl_2N_2O_5$; $[M+H]^+$: 547.1, found: 547.1.

Example 14

Preparation of 2-((6-((5-cyclopropyl-3-(2,6-dichlorophenyl)isoxazol-4-yl)methoxy)naphthalen-2-yl)oxy)benzoic acid (Compound 14)

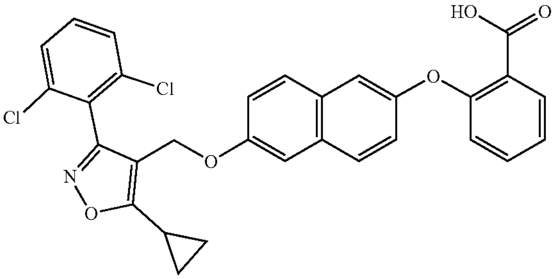

Following the procedure of Example 1, the title Compound 14 was obtained by substituting methyl 2-fluorobenzoate for 6-bromonicotinic acid methyl ester.

$^1$H NMR (400 MHz, DMSO-$d_6$) δ 7.82 (d, J=7.8 Hz, 1H), 7.73 (d, J=8.9 Hz, 1H), 7.66-7.57 (m, 3H), 7.55-7.45 (m, 2H), 7.26 (d, J=10.6 Hz, 2H), 7.21-7.11 (m, 2H), 6.99 (d, J=8.3 Hz, 1H), 4.94 (s, 2H), 1.27-1.06 (m, 5H). LCMS (ESI): calculated for $C_{30}H_{21}Cl_2NO_5$; $[M+H]^+$: 546.1, found: 546.1

Example 15

Preparation of 2-((6-((5-cyclopropyl-3-(2,6-dichlorophenyl)isoxazol-4-yl)methoxy)naphthalen-2-yl)oxy)nicotinic acid (Compound 15)

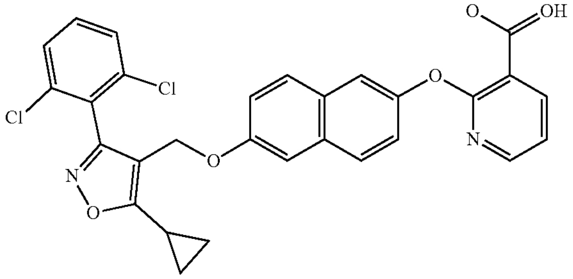 [SMILES: O=C(O)c1cccnc1Oc1ccc2cc(OCc3c(-c4c(Cl)cccc4Cl)noc3C3CC3)ccc2c1]

Following the procedure of Example 1, the title Compound 15 was obtained by substituting methyl 2-chloronicotinate for 6-bromonicotinic acid methyl ester. $^1$H NMR (400 MHz, DMSO-$d_6$) δ 8.30-8.19 (m, 2H), 7.73 (dd, J=19.2, 9.0 Hz, 2H), 7.60 (d, J=7.9 Hz, 2H), 7.55-7.47 (m, 2H), 7.32 (d, J=2.5 Hz, 1H), 7.26-7.18 (m, 2H), 6.92 (dd, J=8.9, 2.5 Hz, 1H), 4.98 (s, 2H), 1.23-1.10 (m, 5H). LCMS (ESI): calculated for $C_{29}H_{20}Cl_2N_2O_5$; $[M+H]^+$: 547.1, found: 547.1.

Example 16

Preparation of 3-((6-((5-cyclopropyl-3-(2,6-dichlorophenyl)isoxazol-4-yl)methoxy)naphthalen-2-yl)oxy)isonicotinic acid (Compound 16)

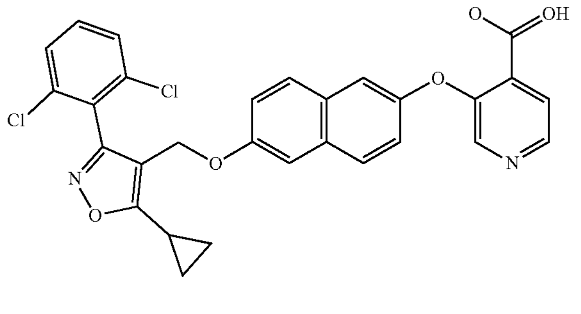 [SMILES: O=C(O)c1ccncc1Oc1ccc2cc(OCc3c(-c4c(Cl)cccc4Cl)noc3C3CC3)ccc2c1]

Following the procedure of Example 1, the title Compound 16 was obtained by substituting methyl 3-fluoroisonicotinate for 6-bromonicotinic acid methyl ester.

$^1$H NMR (400 MHz, DMSO-$d_6$) δ 8.52 (d, J=4.8 Hz, 1H), 8.39 (s, 1H), 7.76 (d, J=8.9 Hz, 1H), 7.73 (d, J=4.9 Hz, 1H), 7.64 (d, J=9.0 Hz, 1H), 7.59 (d, J=7.7 Hz, 2H), 7.50 (dd, J=9.0, 7.0 Hz, 1H), 7.32-7.15 (m, 4H), 6.89 (dd, J=8.9, 2.5 Hz, 1H), 4.95 (s, 2H), 1.27-1.09 (m, 5H). LCMS (ESI): calculated for $C_{29}H_{20}Cl_2N_2O_5$; $[M+H]^+$: 547.1, found: 547.1.

Example 17

Preparation of 6(6-((5-cyclopropyl-3-(2-(trifluoromethoxy)phenyl) isoxazol-4-yl)methoxy)naphthalen-2-yl)oxy)nicotinic acid (Compound 17)

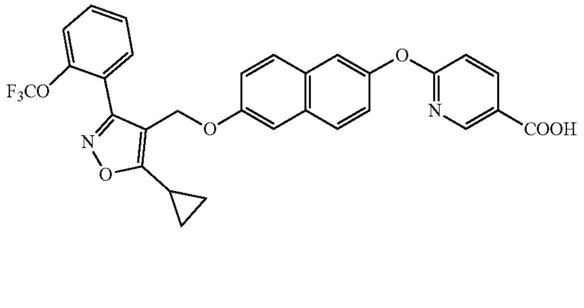 [SMILES: O=C(O)c1ccc(Oc2ccc3cc(OCc4c(-c5ccccc5OC(F)(F)F)noc4C4CC4)ccc3c2)nc1]

Following the procedure of Example 1, the title Compound 17 was obtained by substituting 4-(chloromethyl)-5-cyclopropyl-3-(2-(trifluoromethoxy)phenyl) isoxazole for 1A-1.

$^1$H NMR (400 MHz, DMSO-$d_6$) δ 8.62 (s, 1H), 8.27 (d, J=8.1 Hz, 1H), 7.75 (dt, J=31.9, 15.9 Hz, 2H), 7.61 (s, 2H), 7.56-7.43 (m, 2H), 7.36 (s, 1H), 7.29 (d, J=8.6 Hz, 1H), 7.11 (d, J=8.2 Hz, 1H), 7.00 (d, J=8.5 Hz, 1H), 5.03 (s, 2H), 2.44-2.37 (m, 1H), 1.20-1.05 (m, 4H). LCMS (ESI): calculated for $C_{30}H_2$, $F_3N_2O_6$; $[M+H]^+$: 563.1, found: 563.1.

Example 18

Preparation of 6-6((5-cyclopropyl-3-(2,6-dichloro-4-fluorophenyl) isoxazol-4-yl)methoxy)naphthalen-2-yl)oxy)nicotinic acid (Compound 18)

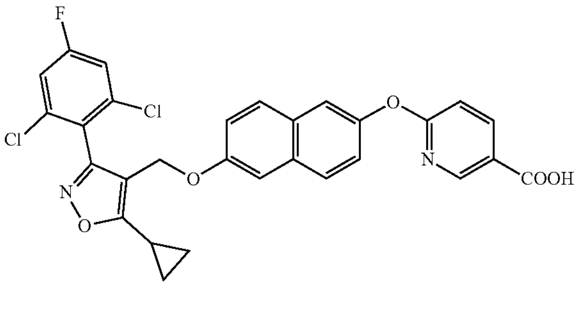 [SMILES: O=C(O)c1ccc(Oc2ccc3cc(OCc4c(-c5c(Cl)cc(F)cc5Cl)noc4C4CC4)ccc3c2)nc1]

Following the procedure of Example 1, the title Compound 18 was obtained by substituting 4-(chloromethyl)-5-cyclopropyl-3-(2,6-dichloro-4-fluorophenyl) isoxazole for 1A-1.

$^1$H NMR (400 MHz, DMSO-$d_6$) δ 8.63 (s, 1H), 8.27 (d, J=7.9 Hz, 1H), 7.87-7.63 (m, 4H), 7.60 (s, 1H), 7.40-7.24 (m, 2H), 7.11 (d, J=8.0 Hz, 1H), 6.96 (d, J=8.6 Hz, 1H), 4.98 (s, 2H), 2.47-2.40 (m, 1H), 1.23-1.08 (m, 4H). LCMS (ESI): calculated for $C_{29}H_{19}Cl_2FN_2O_5$; $[M+H]^+$: 565.1, found: 565.1.

Example 19

Preparation of 6-((6-((5-cyclopropyl-3-(2,6-dichloro-4-methoxyphenyl) isoxazol-4-yl)methoxy) naphthalen-2-yl)oxy)nicotinic acid (Compound 19)

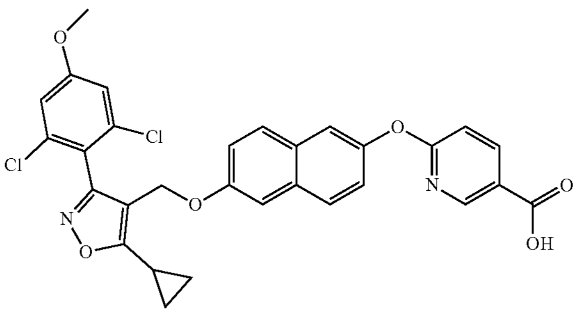 [SMILES: COc1cc(Cl)c(-c2noc(C3CC3)c2COc2ccc3cc(Oc4ccc(C(=O)O)cn4)ccc3c2)c(Cl)c1]

Following the procedure of Example 1, the title Compound 19 was obtained by substituting 4-(chloromethyl)-5-cyclopropyl-3-(2,6-dichloro-4-methoxyphenyl) isoxazole for 1A-1.

LCMS (ESI): calculated for $C_{30}H_{22}C_{12}N_2O_6$; [M+H]+: 577.1, found: 577.1.

Example 20

Preparation of 6-((6-((5-cyclopropyl-3-(2,6-dichlorophenyl)isoxazol-4-yl)methoxy)-1-fluoronaphthalen-2-yl)oxy)nicotinic acid (Compound 20)

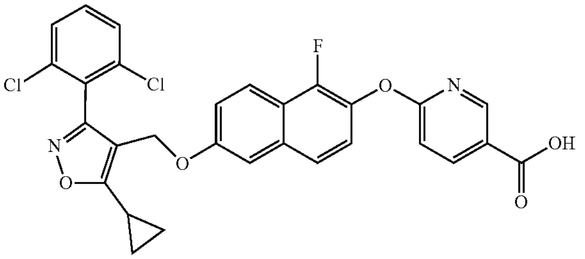 [SMILES: O=C(O)c1ccc(Oc2ccc3cc(OCc4c(-c5c(Cl)cccc5Cl)noc4C4CC4)ccc3c2F)nc1]

(a) Referring to the following reaction equation (Route C), Compound 20A-1 (1.0 g, 4.15 mmol, 1 eq.), Compound 20A-2 (0.90 g, 4.15 mmol, 1 eq.) and cesium carbonate (2.70 g, 8.30 mmol, 2 eq.) were dissolved in DMF (10 ml). The reaction was carried out at 65° C. for 2 h. After cooling, 10 ml water and 10 ml EA (ethyl acetate) were added for extraction, and the organic phase was washed with water and concentrated to dryness to give Compound 20A, methyl 6-((6-bromo-1-fluoronaphthalen-2-yl)oxy)nicotinate, 1.2 g, yield: 77.0%. LCMS (ESI): calculated for $C_{17}H_{11}BrFNO_3$; $[M+H]^+$: 376.0, found: 376.0.

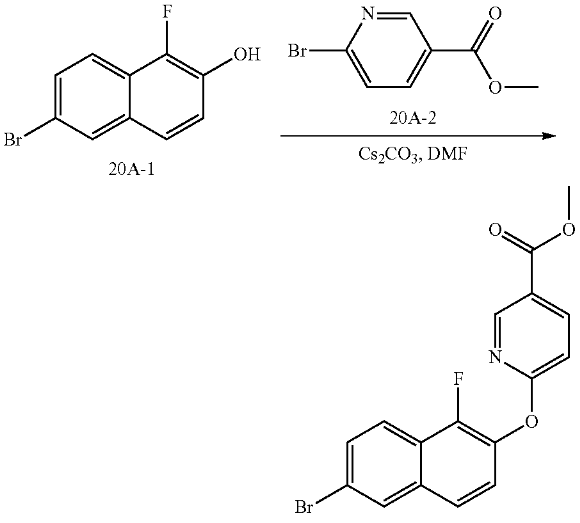

20A-1

20A (b) Referring to the following reaction equation, compound 20A (200 mg, 0.53 mmol, 1 eq) was dissolved in dry THF (2 ml), then KOAc (104 mg, 1.06 mmol, 2 eq), $Pd(dppf)_2Cl_2$ (39 mg, 0.053 mmol, 0.1 eq), and bis(pinacolato)diboron (135 mg, 0.53 mmol, 1 eq) were added under $N_2$, and the reaction mixture was heated to reflux for 2 h. After cooling, 10 ml water and 10 ml EtOAc were added for extraction, and the organic phase was washed with water and concentrated to dryness. The residue was purified by silica gel column chromatography (petroleum Ether:EtOAc=3:1) to give Compound 20B, methyl 6-((1-fluoro-6-(4,4,5,5-tetramethyl-1,3,2-dioxaborolan-2-yl)naphthalen-2-yl)oxy)nicotinate, 151 mg, yield: 67.1%. LCMS (ESI): calculated for $C_{23}H_{23}BFNO_5$; $[M+H]^+$: 424.2, found: 424.2.

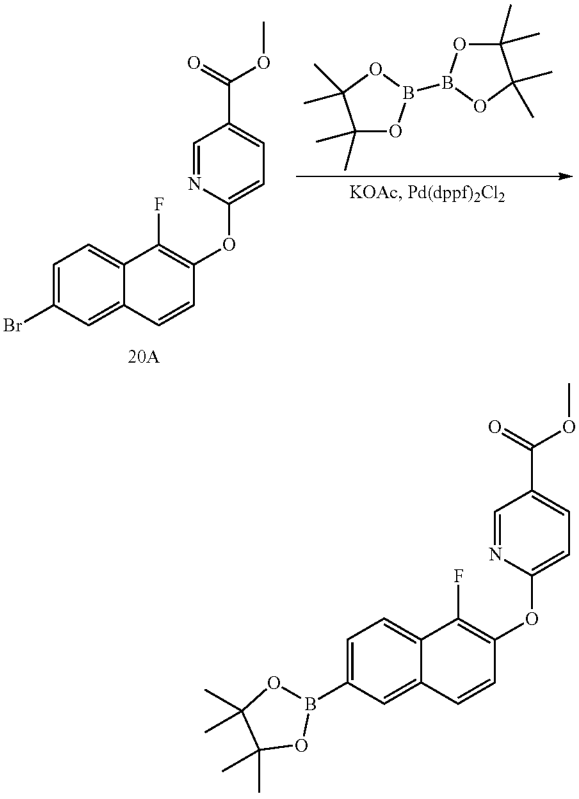

20A

20B (c) Referring to the following reaction equation, compound 20B (100 mg) was dissolved in EtOH (2 ml), then 30% $H_2O_2$ aqueous solution (1 ml) were added. The reaction mixture was stirred at room temperature for 1 h, quenched with saturated aqueous $Na_2SO_3$, and extracted with EA. The organic phase was concentrated and purified on a column (PE/EA=3/1) to give the compound 20C (36 mg, yield: 37.0%). LCMS (ESI): calculated for $C_{17}H_{12}FNO_4$; $[M+H]^+$: 314.1, found: 314.1.

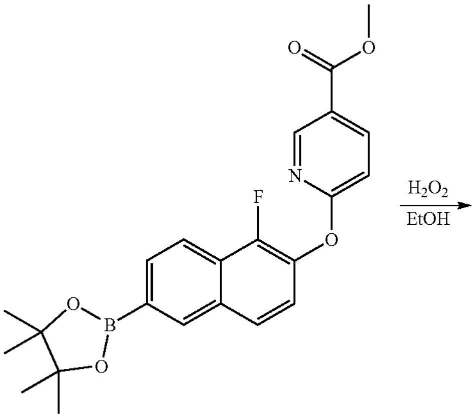

20B

-continued

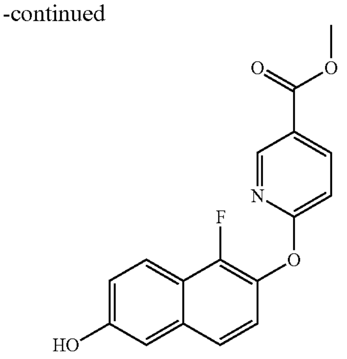

20C (d) Referring to the following reaction equation, Compound 20C (0.2 g, 0.47 mmol, 1 eq.), 1A-1 (0.1 g, 0.47 mmol, 1 eq.) and cesium carbonate (0.306 g, 0.94 mmol, 2 eq.) were dissolved in DMF (10 ml) for reacting. The reaction was carried out at 65° C. for 2 h. After cooling, 10 ml water and 10 ml EtOAc were added for extraction, and the organic phase was washed with water and concentrated to dryness to give Compound 20D, 0.21 g, yield: 80.0%.

LCMS (ESI): calculated for $C_{30}H_{21}Cl_2FN_2O_5$; $[M+H]^+$: 579.1, found: 579.1.

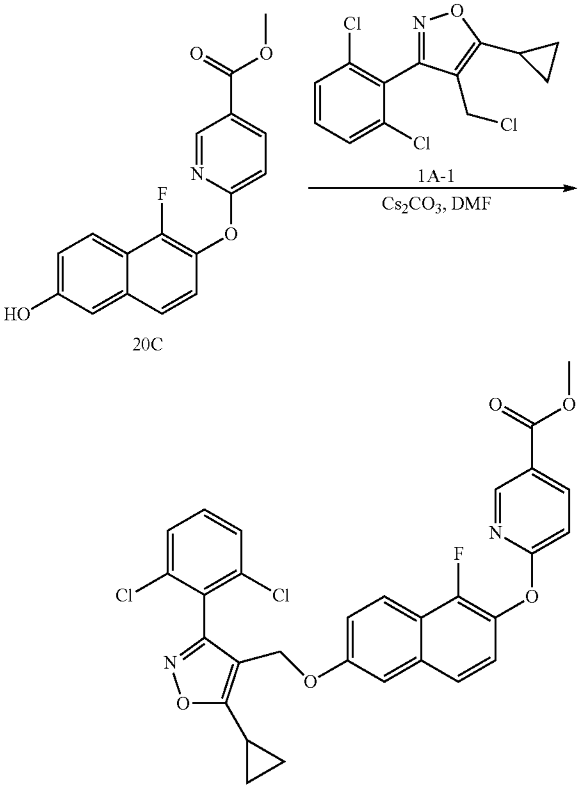

20C 1A-1

20

(e) Referring to the following reaction equation, compound 20D (100 mg) was dissolved in dry THF (2 ml), then 10% NaOH aqueous solution (1 ml) were added under $N_2$, and the reaction mixture was heated to reflux for 1 h. The pH of the reaction solution was adjusted to 3 to 4 by adding 1N HCl solution, and 10 ml EA was added for extraction. The organic phase was concentrated and purified on a column (PE/EA/AcOH=1/1/0.01 elution) to give the title compound 20 (36 mg, yield: 37.0%).

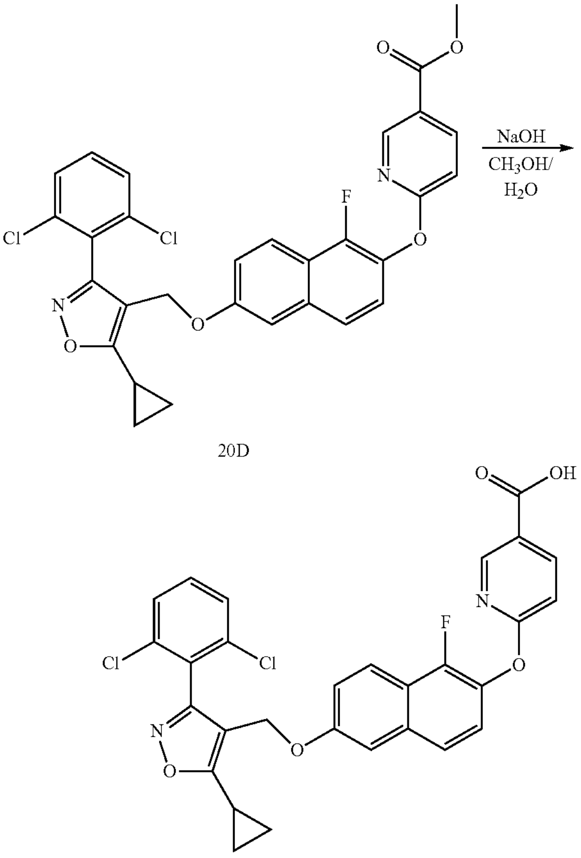

20D

20

$^1$H NMR (400 MHz, DMSO-$d_6$) δ 8.63 (d, J=2.4 Hz, 1H), 8.30 (dd, J=8.7, 2.4 Hz, 1H), 7.92 (d, J=9.0 Hz, 1H), 7.70 (s, 1H), 7.64 (d, J=5.3 Hz, 1H), 7.60 (d, J=6.4 Hz, 1H), 7.57 (d, J=4.3 Hz, 2H), 7.42-7.36 (m, 2H), 7.17 (d, J=8.6 Hz, 1H), 5.09 (s, 2H), 1.22-1.06 (m, 5H). LCMS (ESI): calculated for $C_{29}H_{19}Cl_2FN_2O_5$; $[M+H]^+$: 565.1, found: 565.1.

Example 21

Preparation of 6-((1-chloro-6-((5-cyclopropyl-3-(2,6-dichlorophenyl) isoxazol-4-yl)methoxy)naphthalen-2-yl)oxy)nicotinic acid (Compound 21)

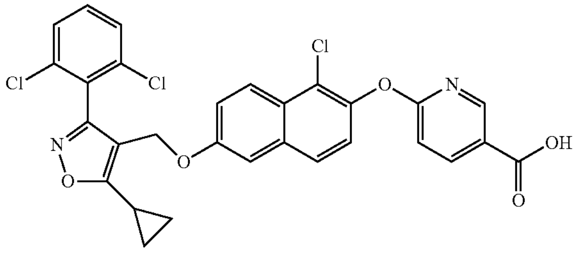 [SMILES: O=C(O)c1ccc(Oc2ccc3cc(OCc4c(-c5c(Cl)cccc5Cl)noc4C4CC4)ccc3c2Cl)nc1]

Following the procedure of Example 20, the title Compound 21 was obtained by substituting 6-bromo-1-chloronaphthalen-2-ol for 20A-1.

$^1$H NMR (400 MHz, DMSO-$d_6$) δ 8.63 (s, 1H), 8.27 (d, J=7.9 Hz, 1H), 7.87-7.63 (m, 4H), 7.60 (s, 1H), 7.40-7.24 (m, 2H), 7.11 (d, J=8.0 Hz, 1H), 6.96 (d, J=8.6 Hz, 1H), 4.98 (s, 2H), 2.47-2.40 (m, 1H), 1.23-1.08 (m, 4H). LCMS (ESI): calculated for $C_{29}H_{19}Cl_3N_2O_5$; $[M+H]^+$: 581.0, found: 581.0.

Example 22

Preparation of 6-((6-((5-cyclopropyl-3-(2,6-dichlorophenyl)isoxazol-4-yl)methoxy)naphthalen-1-yl)oxy)nicotinic acid (Compound 22)

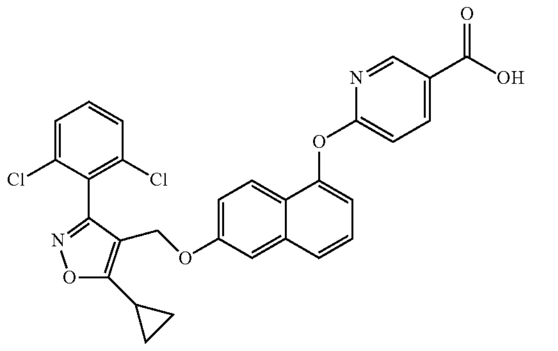 [SMILES: O=C(O)c1ccc(Oc2cccc3cc(OCc4c(-c5c(Cl)cccc5Cl)noc4C4CC4)ccc23)nc1]

(a) Referring to the following reaction equation (Route D), Compound 22A-1 (2.0 g, 12.49 mmol, 1 eq.), Compound 22A-2 (1.71 g, 9.99 mmol, 0.8 eq.) and cesium carbonate (6.09 g, 18.74 mmol, 1.5 eq.) were dissolved in DMF (20 ml) for reacting. The reaction was carried out at 65° C. for 3 h. After cooling, 30 ml water and 30 ml EA (ethyl acetate) were added for extraction, and the organic phase was washed with water and concentrated to dryness. The residue was purified by silica gel column chromatography (petroleum:AcOEt=5:1) to give Compound 22A, methyl 6-((6-hydroxynaphthalen-1-yl)oxy)nicotinate, 1.1 g, yield: 37.3%. LCMS (ESI): calculated for $C_{17}H_{13}NO_4$; $[M+H]^+$: 296.1, found: 296.1.

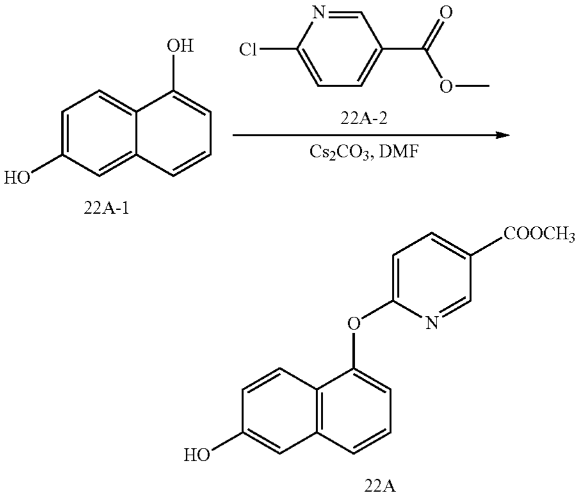

22A-1
22A-2
22A (b) Referring to the following reaction equation, Compound 22A (0.2 g, 0.68 mmol, 1 eq.), 22A-3 (0.2 g, 0.68 mmol, 1 eq.) and cesium carbonate (0.44 g, 1.36 mmol, 2 eq.) were dissolved in DMF (5 ml) for reacting. The reaction was carried out at 40° C. for 2 h. After cooling, 10 ml water and 10 ml EA were added for extraction, and the organic phase was washed with water and concentrated to dryness to give Compound 22B, methyl 6-((6((5-cyclopropyl-3-(2,6-dichlorophenyl)isoxazol-4-yl)methoxy)naphthalen-1-yl) oxy) nicotinate, 0.31 g, yield: 81.2%. LCMS (ESI): calculated for $C_{30}H_{22}Cl_2N_2O_5$; $[M+H]^+$: 561.1, found: 561.1.

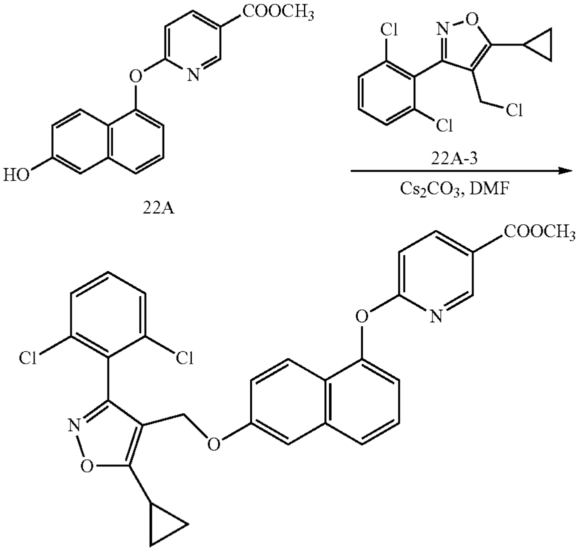

22A
22A-3
22B (c) Referring to the following reaction equation, compound 22B (100 mg) was dissolved in methanol (2 ml), then 10% NaOH aqueous solution (1 ml) was added, the temperature was raised to 60° C., and the reaction was carried out for 0.5 h. The pH of the reaction solution was adjusted to 2 to 4 by adding 1N HCl solution, and 10 ml EA was added for extraction. The organic phase was concentrated on a column (PE/EA/AcOH=1/1/0.01 elution) to give the title compound 22 (42 mg, yield: 43.2%).

$^1$H NMR (400 MHz, DMSO-$d_6$) δ 13.11 (br s, 1H), 8.56 (s, 1H), 8.28 (d, J=8.5 Hz, 1H), 7.66 (d. J=8.3 Hz, 1H), 7.56-7.61 (m, 3H), 7.45-7.53 (m, 2H), 7.39 (s, 1H), 7.15 (t, J=9.6 Hz, 2H), 6.9 (d, J=9.2 Hz, 2H), 4.98 (s, 2H), 1.09-1.28 (m, 5H). LCMS (ESI): calculated for $C_{29}H_{20}Cl_2N_2O_5$; $[M+H]^+$: 547.1, found: 547.1.

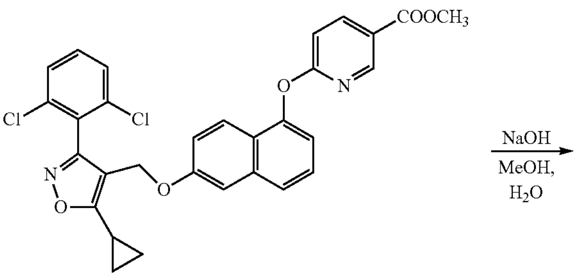

22B

-continued

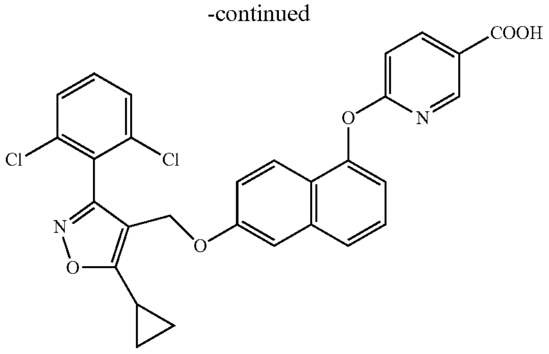

22

Example 23

Preparation of 6-((6-((5-cyclopropyl-3-(2,6-dichlorophenyl)isoxazol-4-yl)methoxy)naphthalen-1-yl)oxy)picolinic acid (Compound 23)

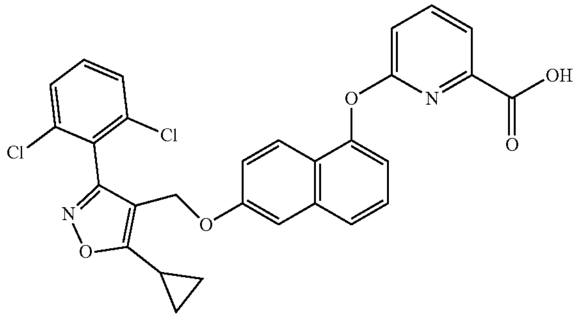 [SMILES: O=C(O)c1cccc(Oc2cccc3cc(OCc4c(-c5c(Cl)cccc5Cl)noc4C4CC4)ccc23)n1]

Following the procedure of Example 22, the title Compound 23 was obtained by substituting methyl 6-fluoropicolinate for 22A-2.

$^1$H NMR (400 MHz, DMSO-$d_6$) δ7.99 (t, J=7.8 Hz, 1H), 7.78 (d, J=7.4 Hz, 1H), 7.73 (d, J=9.2 Hz, 1H), 7.63 (d, J=8.3 Hz, 1H), 7.60-7.55 (m, 2H), 7.52-7.44 (m, 2H), 7.40-7.37 (m, 1H), 7.20 (d, J=8.3 Hz, 1H), 7.09 (d, J=7.5 Hz, 1H), 6.94-6.90 (m, 1H), 4.99 (s, 2H), 1.23-1.09 (m, 5H). LCMS (ESI): calculated for $C_{29}H_{20}Cl_2N_2O_5$; $[M+H]^+$: 547.1, found: 547.1.

Example 24

Preparation of 2-((6-((5-cyclopropyl-3-(2,6-dichlorophenyl)isoxazol-4-yl)methoxy)naphthalen-1-yl)oxy)isonicotinic acid (Compound 24)

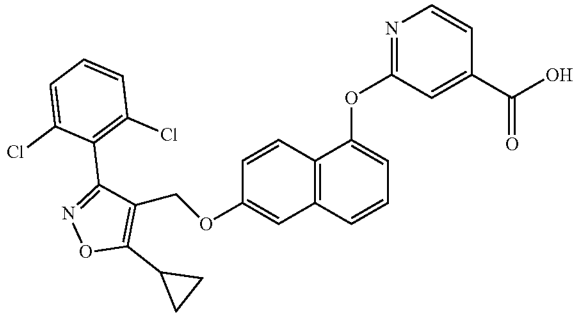 [SMILES: O=C(O)c1ccnc(Oc2cccc3cc(OCc4c(-c5c(Cl)cccc5Cl)noc4C4CC4)ccc23)c1]

Following the procedure of Example 22, the title Compound 24 was obtained by substituting methyl 2-fluoroisonicotinate for 22A-2.

$^1$H NMR (400 MHz, DMSO-$d_6$) δ 8.22 (d, J=5.1 Hz, 1H), 7.67-7.62 (m, 2H), 7.58 (d, J=8.0 Hz, 2H), 7.53-7.42 (m, 3H), 7.38 (s, 2H), 7.11 (d, J=7.5 Hz, 1H), 6.89 (dd, J=9.2, 2.4 Hz, 1H), 4.98 (s, 2H), 1.22-1.07 (m, 5H). LCMS (ESI): calculated for $C_{29}H_{20}Cl_2N_2O_5$; $[M+H]^+$: 547.1, found: 547.1.

Example 25

Preparation of 3-((6-((5-cyclopropyl-3-(2,6-dichlorophenyl)isoxazol-4-yl)methoxy)naphthalen-1-yl)oxy)picolinic acid (Compound 25)

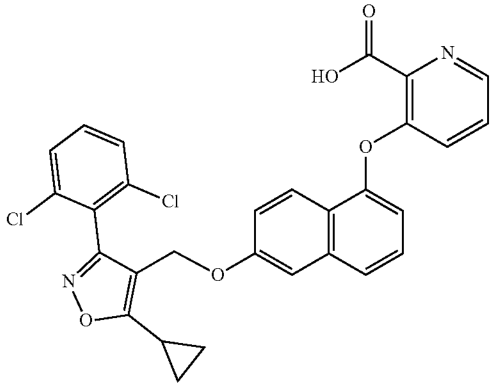 [SMILES: O=C(O)c1ncccc1Oc1cccc2cc(OCc3c(-c4c(Cl)cccc4Cl)noc3C3CC3)ccc12]

Following the procedure of Example 22, the title Compound 25 was obtained by substituting methyl 3-fluoropicolinate for 22A-2.

$^1$H NMR (400 MHz, DMSO-$d_6$) δ 8.41-8.37 (m, 1H), 7.90 (d, J=9.2 Hz, 1H), 7.62-7.54 (m, 3H), 7.53-7.47 (m, 2H), 7.43-7.35 (m, 2H), 7.35-7.30 (m, 1H), 6.99-6.94 (m, 1H), 6.77 (d, J=7.6 Hz, 1H), 5.00 (s, 2H), 1.21-1.10 (m, 5H). LCMS (ESI): calculated for $C_{29}H_{20}O_2N_2O_5$; $[M+H]^+$: 547.1, found: 547.1.

Example 26

Preparation of 2-((6-((5-cyclopropyl-3-(2,6-dichlorophenyl)isoxazol-4-yl)methoxy)naphthalen-1-yl)oxy)-4-fluorobenzoic acid (Compound 26)

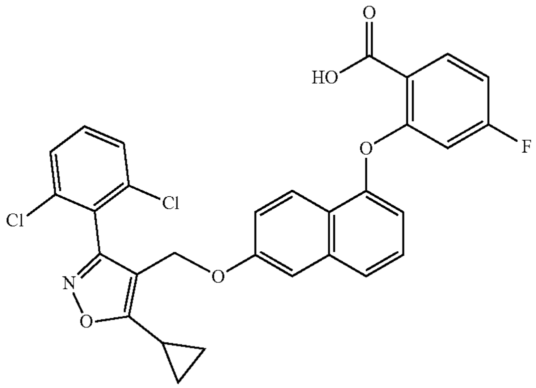 [SMILES: O=C(O)c1ccc(F)cc1Oc1cccc2cc(OCc3c(-c4c(Cl)cccc4Cl)noc3C3CC3)ccc12]

Following the procedure of Example 22, the title Compound 26 was obtained by substituting methyl 2,4-difluorobenzoate for 22A-2.

$^1$H NMR (400 MHz, DMSO-$d_6$) δ 8.22 (d, J=5.1 Hz, 1H), 7.67-7.61 (m, 2H), 7.57 (s, 2H), 7.52-7.43 (m, 3H), 7.38 (s, 2H), 7.11 (d, J=7.5 Hz, 1H), 6.90 (s, OH), 4.98 (s, 2H), 1.20-1.06 (m, 5H). LCMS (ESI): calculated for $C_{30}H_{20}Cl_2FNO_5$; $[M+H]^+$: 564.1, found: 564.1.

Example 27

Preparation of 6-((6-((5-cyclopropyl-3-(2,6-dichlorophenyl)isoxazol-4-yl)methoxy)naphthalen-1-yl)oxy)-2-methylnicotinic acid (Compound 27)

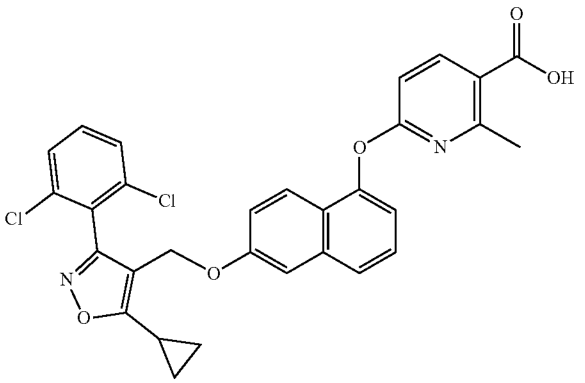 [SMILES: Cc1nc(Oc2cccc3cc(OCc4c(-c5c(Cl)cccc5Cl)noc4C4CC4)ccc23)ccc1C(=O)O]

Following the procedure of Example 22, the title Compound 27 was obtained by substituting methyl 6-chloro-2-methylnicotinate for 22A-2.

$^1$H NMR (400 MHz, DMSO-$d_6$) δ 8.20 (d, J=8.5 Hz, 1H), 7.63 (dd, J=8.8, 4.5 Hz, 2H), 7.57 (s, 1H), 7.52-7.43 (m, 1H), 7.38 (d, J=2.7 Hz, 1H), 7.11 (d, J=7.5 Hz, 1H), 6.90 (dd, J=9.2, 2.5 Hz, 1H), 6.81 (d, J=8.6 Hz, 1H), 4.98 (s, 2H), 2.48 (s, 3H), 1.23-1.00 (m, 5H). LCMS (ESI): calculated for $C_{30}H_{22}Cl_2N_2O_5$; $[M+H]^+$: 561.1, found: 561.1.

Example 28

Preparation of 6-((6-((5-cyclopropyl-3-(2,6-dichlorophenyl)isoxazol-4-yl)methoxy)naphthalen-1-yl)oxy)-5-methylnicotinic acid (Compound 28)

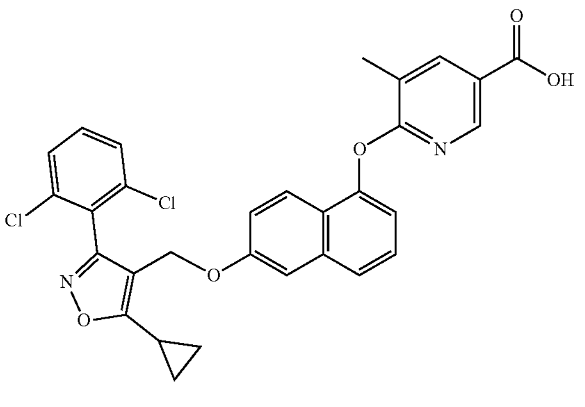 [SMILES: Cc1cc(C(=O)O)cnc1Oc1cccc2cc(OCc3c(-c4c(Cl)cccc4Cl)noc3C3CC3)ccc12]

Following the procedure of Example 22, the title Compound 28 was obtained by substituting methyl 6-chloro-5-methylnicotinate for 22A-2.

$^1$H NMR (400 MHz, DMSO-$d_6$) δ 8.31 (d, J=2.3 Hz, 1H), 8.19 (d, J=2.3 Hz, 1H), 7.64 (d, J=8.3 Hz, 1H), 7.61-7.55 (m, 3H), 7.53-7.44 (m, 2H), 7.38 (d, J=2.7 Hz, 1H), 7.11 (d, J=7.5 Hz, 1H), 6.88 (dd, J=9.1, 2.5 Hz, 1H), 4.98 (s, 2H), 2.47 (s, 3H), 1.20-1.08 (m, 5H). LCMS (ESI): calculated for $C_{30}H_{22}Cl_2N_2O_5$; $[M+H]^+$: 561.1, found: 561.1.

Example 29

Preparation of 6-((5-chloro-6-((5-cyclopropyl-3-(2,6-dichlorophenyl)-isoxazol-4-yl)methoxy)naphthalen-2-yl)oxy)nicotinic acid (Compound 29)

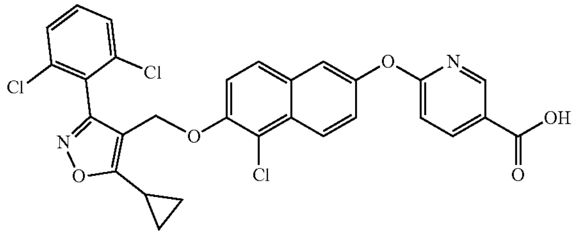 [SMILES: O=C(O)c1ccc(Oc2ccc3c(Cl)c(OCc4c(-c5c(Cl)cccc5Cl)noc4C4CC4)ccc3c2)nc1]

Following the procedure of Example 32, the title Compound 29 was obtained by substituting 6-bromo-1-chloronaphthalen-2-ol for 32A-1.

$^1$H NMR (400 MHz, DMSO-$d_6$) δ 8.63 (s, 1H), 8.29 (d, J=8.6 Hz, 1H), 7.92 (d, J=8.9 Hz, 1H), 7.70 (s, 1H), 7.65-7.46 (m, 4H), 7.38 (s, 2H), 7.17 (d, J=8.5 Hz, 1H), 5.09 (s, 2H), 1.21-1.02 (m, 5H). LCMS (ESI): calculated for $C_{29}H_{19}Cl_3N_2O_5$; $[M+H]^+$: 581.0, found: 581.0.

Example 30

Preparation of 6-((6-((5-cyclopropyl-3-(2,6-dichlorophenyl)isoxazol-4-yl)methoxy)-2-fluoronaphthalen-1-yl)oxy)nicotinic acid (Compound 30)

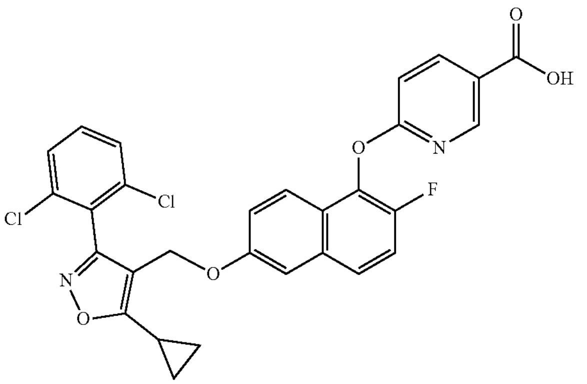 [SMILES: O=C(O)c1ccc(Oc2c(F)ccc3cc(OCc4c(-c5c(Cl)cccc5Cl)noc4C4CC4)ccc23)nc1]

Following the procedure of Example 20, the title Compound 30 was obtained by substituting 6-bromo-2-fluoronaphthalen-1-ol for 20A-1.

$^1$H NMR (400 MHz, DMSO-$d_6$) δ 8.59 (d, J=2.4 Hz, 1H), 8.31 (dd, J=8.6, 2.4 Hz, 1H), 7.86 (d, J=9.1 Hz, 1H), 7.66 (d, J=6.9 Hz, 1H), 7.59 (s, 1H), 7.56 (dd, J=5.7, 3.3 Hz, 1H), 7.51 (dd, J=9.0, 7.1 Hz, 1H), 7.46-7.39 (m, 2H), 7.25 (d, J=8.6 Hz, 1H), 7.05 (dd, J=9.2, 2.4 Hz, 1H), 5.02 (s, 2H), 1.28-1.08 (m, 5H). LCMS (ESI): calculated for $C_{29}H_{19}Cl_2FN_2O_5$; $[M+H]^+$: 565.1, found: 565.1.

Example 31

Preparation of 6-((7-((5-cyclopropyl-3-(2,6-dichlorophenyl)isoxazol-4-yl)methoxy)naphthalen-2-yl)oxy)nicotinic acid (Compound 31)

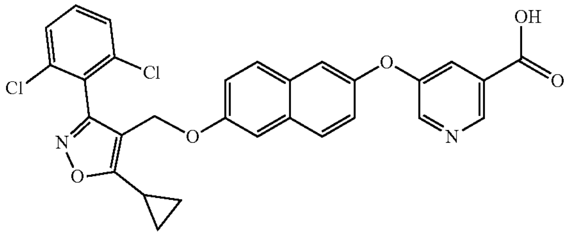 [SMILES: O=C(O)c1cncc(Oc2ccc3cc(OCc4c(-c5c(Cl)cccc5Cl)noc4C4CC4)ccc3c2)c1]

Following the procedure of Example 1, the title Compound 31 was obtained by substituting naphthalene-2,7-diol for 1A-2.

$^1$H NMR (400 MHz, DMSO-$d_6$) δ 8.64 (s, 1H), 8.28 (d, J=8.6 Hz, 1H), 7.85 (d, J=8.8 Hz, 1H), 7.77 (d, J=9.0 Hz, 1H), 7.58 (d, J=8.1 Hz, 2H), 7.55-7.43 (m, 2H), 7.27 (s, 1H), 7.13 (t, J=9.9 Hz, 2H), 6.89 (d, J=8.9 Hz, 1H), 4.95 (s, 2H), 1.29-1.06 (m, 5H). LCMS (ESI): calculated for $C_{29}H_{20}Cl_2N_2O_5$; $[M+H]^+$: 547.1, found: 547.1.

Example 32

Preparation of 6-((6-((5-cyclopropyl-3-(2,6-dichlorophenyl)isoxazol-4-yl)methoxy)-5-fluoronaphthalen-2-yl)oxy)nicotinic acid (Compound 32)

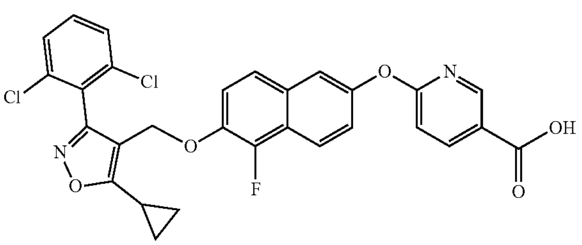 [SMILES: O=C(O)c1ccc(Oc2ccc3c(F)c(OCc4c(-c5c(Cl)cccc5Cl)noc4C4CC4)ccc3c2)nc1]

(a) Referring to the following reaction equation (Route B), Compound 32A-1 (1.0 g, 4.15 mmol, 1 eq.), Compound 1A-1 (1.44 g, 4.15 mmol, 1 eq.) and cesium carbonate (2.70 g, 8.30 mmol, 2 eq.) were dissolved in DMF (10 ml) for reacting. The reaction was carried out at 65° C. for 2 h. After cooling, 10 ml water and 10 ml EA (ethyl acetate) were added for extraction, and the organic phase was washed with water and concentrated to dryness to give Compound 32A, 4-(((6-bromo-1-fluoronaphthalen-2-yl)oxy)methyl)-5-cyclopropyl-3-(2,6-dichlorophenyl)isoxazole, 1.51 g, yield: 71.9%. LCMS (ESI): calculated for $C_{23}H_{15}BrCl_2FNO_2$; $[M+H]^+$: 506.0, found: 506.0.

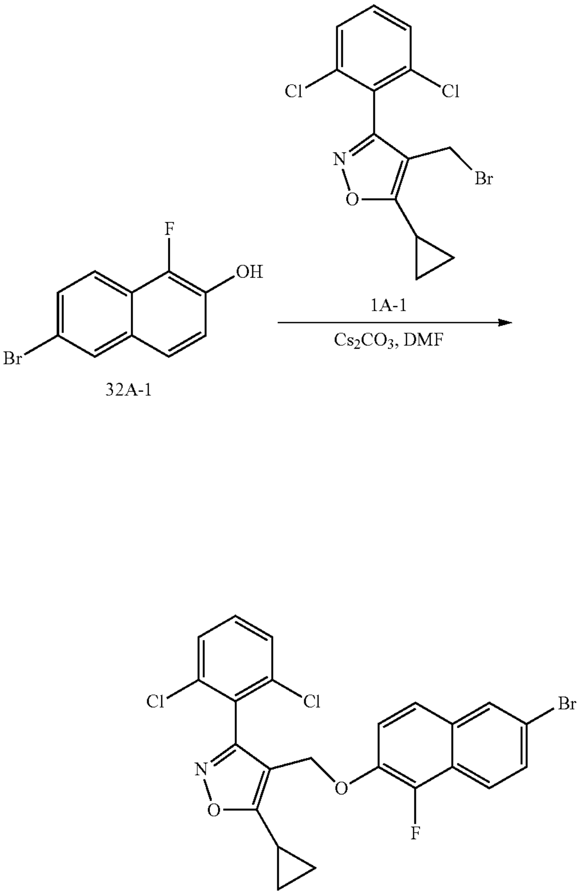

(b) Referring to the following reaction equation, compound 32A (200 mg, 0.39 mmol, 1 eq) was dissolved in dry THF (2 ml), then KOAc (76 mg, 0.78 mmol, 2 eq), Pd(dppf)$_2Cl_2$ (28 mg, 0.039 mmol, 0.1 eq), and bis(pinacolato)diboron (100 mg, 0.39 mmol, 1 eq) were added under $N_2$, and the reaction mixture was heated to reflux for 2 h. After cooling, 10 ml water and 10 ml EA were added for extraction, and the organic phase was washed with water and concentrated to dryness. The residue was purified by silica gel column chromatography (petroleum:AcOEt=3:1) to give Compound 32B, 5-cyclopropyl-3-(2,6-dichlorophenyl)-4-(((1-fluoro-6-(4,4,5,5-tetramethyl-1,3,2-dioxaborolan-2-yl)naphthalen-2-yl)oxy)methyl)isoxazole, 137 mg, yield: 62.8%. LCMS (ESI): calculated for $C_{29}H_{27}BCl_2FNO_4$; $[M+H]^+$: 554.1, found: 554.1.

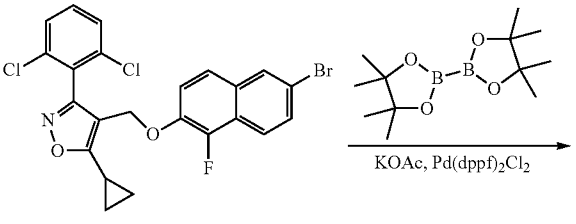

32A

-continued

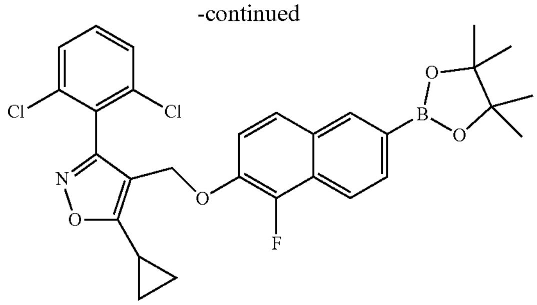

32B (c) Referring to the following reaction equation, compound 32B (100 mg) was dissolved in EtOH (2 ml), then 30% $H_2O_2$ aqueous solution (1 ml) were added. The reaction mixture was stirred at room temperature for 1 h, quenched with saturated aqueous $Na_2SO_3$, and extracted with EA. The organic phase was concentrated and purified on a column (PE/EA=3/1) to give the compound 32C (61 mg, yield: 76.2%). LCMS (ESI): calculated for $C_{23}H_{16}Cl_2FNO_3$; $[M+H]^+$: 444.1, found: 444.1.

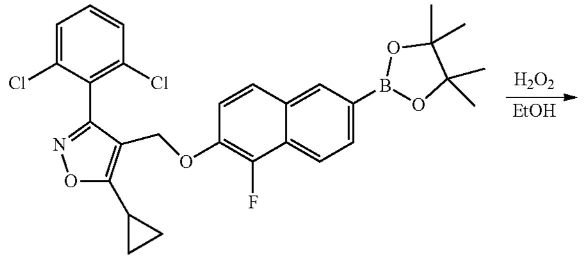

32B

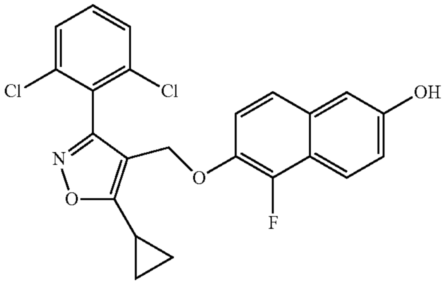

32C (d) Referring to the following reaction equation, Compound 32C (50 mg, 0.11 mmol, 1 eq.), 1A-3 (24.3 mg, 0.11 mmol, 1 eq.) and cesium carbonate (71.5 mg, 0.22 mmol, 2 eq.) were dissolved in DMF (1 ml) for reacting. The reaction was carried out at 65° C. for 2 h. After cooling, 5 ml water and 5 ml EA were added for extraction, and the organic phase was washed with water and concentrated to dryness to give Compound 32D, 40 mg, yield: 61.5%. LCMS (ESI): calculated for $C_{30}H_{21}Cl_2FN_2O_5$; $[M+H]^+$: 579.1, found: 579.1.

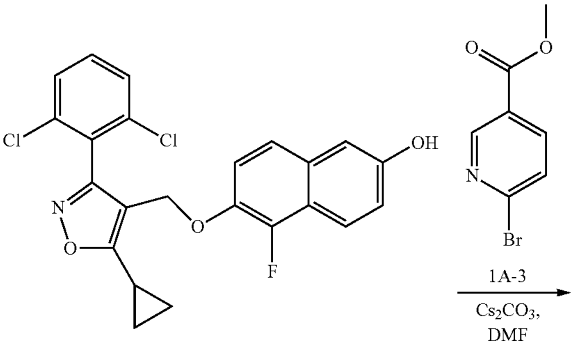

32C

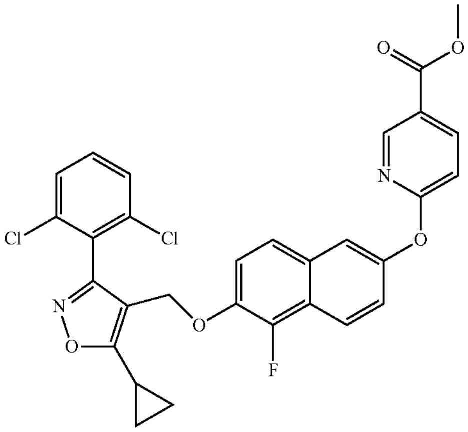

32D (e) Referring to the following reaction equation, compound 32D (30 mg) was dissolved in MeOH (1 ml), then 10% NaOH aqueous solution (0.5 ml) were added under $N_2$, and the reaction mixture was heated to reflux for 1 h. The pH of the reaction solution was adjusted to 3 to 4 by adding 1N HCl solution, and 5 ml EA was added for extraction. The organic phase was concentrated and purified on a column (PE/EA/AcOH=1/1/0.01 elution) to give the title compound 32 (21 mg, yield: 71.7%).

$^1H$ NMR (400 MHz, DMSO-$d_6$) δ 8.59 (d, J=2.3 Hz, 1H), 8.31 (dd, J=8.6, 2.4 Hz, 1H), 7.86 (d, J=9.1 Hz, 1H), 7.62 (d, J=5.3 Hz, 1H), 7.59 (s, 1H), 7.56 (dd, J=5.7, 3.3 Hz, 1H), 7.51 (dd, J=9.0, 7.1 Hz, 1H), 7.46-7.40 (m, 2H), 7.25 (d, J=8.6 Hz, 1H), 7.06 (dd, J=5.7, 4.3 Hz, 1H), 5.02 (s, 2H), 1.26-1.09 (m, 5H). LCMS (ESI): calculated for $C_{29}H_{19}Cl_2FN_2O_5$; $[M+H]^+$: 565.1, found: 565.1.

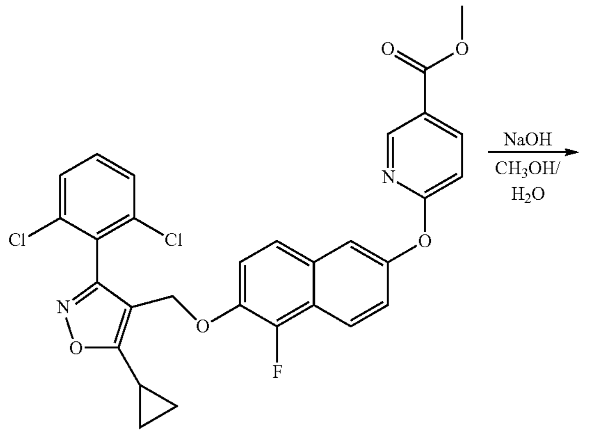

32D

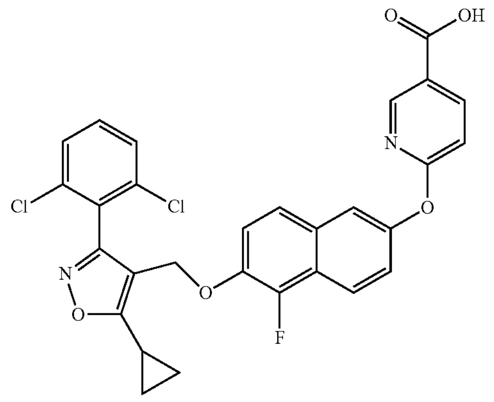

32

Example 33

Preparation of Sodium 6 #6-((5-cyclopropyl-3-(2,6-dichlorophenyl)isoxazol-4-yl) methoxy) naphthalen-2-yl)oxy)nicotinate

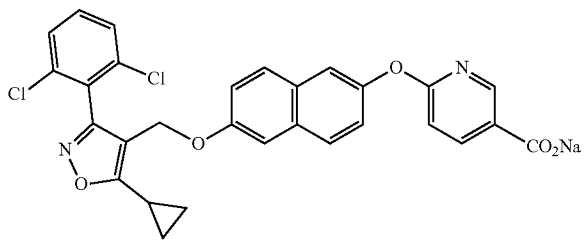

An aq. solution of NaOH (30%, 1.44 g, 1.2 eq) was added to a solution of Compound 1 (4.99 g, 9.12 mmol) in EtOH at r.t. After the reaction mixture was heated at reflux for 6 h, it was cooled to r.t. The solid was collected by filtration, washed with EtOH (10 ml), and dried to give a gray solid (4.07 g, yield: 78.3%).

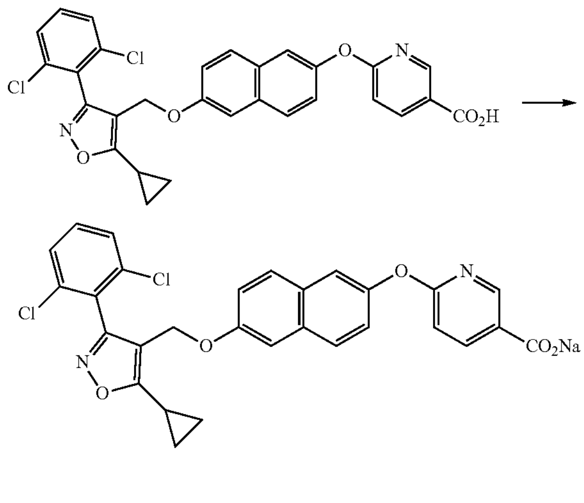

Example 34

Preparation of Calcium 6-((6-((5-cyclopropyl-3-(2,6-dichlorophenyl)isoxazol-4-yl)methoxy) naphthalen-2-yl)oxy)nicotinate

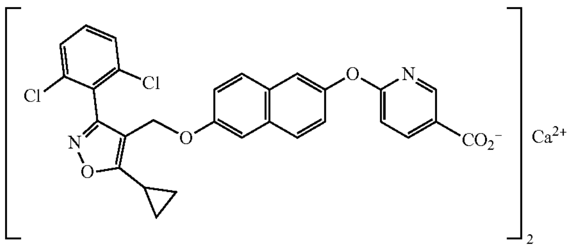

To a solution of Compound 35 (1.00 g, 1.76 mmol) in water (10 ml) was added a solution of $CaCl_2$ (1.0 g, 20%) in water. White precipitates formed. After the reaction mixture was stirred at r.t. for 4 h, the solid was collected by filtration, washed with water (2.0 ml) to give the product as a white solid (0.80 g, 76.7%).

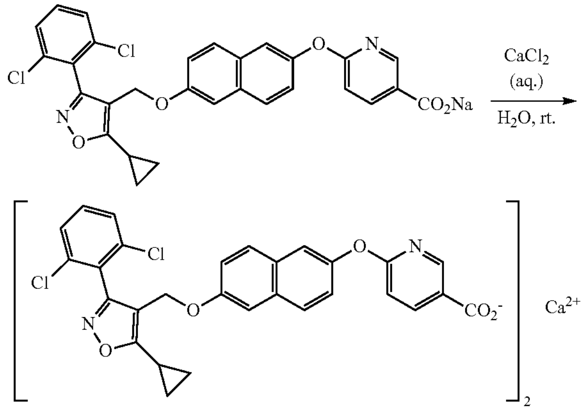

Example 35

Preparation of 2-((6((5-cyclopropyl-3-(2,6-dichlorophenyl)isoxazol-4-yl)methoxy) naphthalen-1-yl)oxy) nicotinic acid

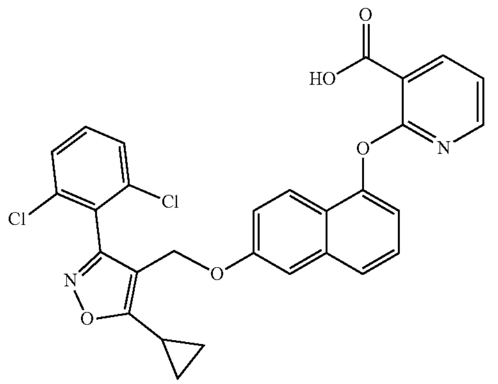 [SMILES: O=C(O)c1cccnc1Oc1cccc2cc(OCc3c(-c4c(Cl)cccc4Cl)noc3C3CC3)ccc12]

The title compound 35 was prepared according to Route D, following the procedure of Example 22. $^1$H NMR (400 MHz, DMSO-$d_6$) δ 13.31 (s, 1H), 8.29-8.24 (m, 1H), 8.15-8.10 (m, 1H), 7.67 (d, J=9.1 Hz, 1H), 7.64-7.56 (m, 3H), 7.53-7.47 (m, 1H), 7.47-7.42 (m, 1H), 7.36 (d, J=2.6 Hz, 1H), 7.22-7.17 (m, 1H), 7.06 (d, J=7.4 Hz, 1H), 6.92-6.87 (m, 1H), 4.98 (s, 2H), 1.24-1.08 (m, 5H). LCMS (ESI): calculated for $C_{29}H_{20}Cl_2N_2O_5$; [M+H]$^+$: 547.1, found: 547.1.

Example 36

Preparation of 6-((5-((5-cyclopropyl-3-(2,6-dichlorophenyl)isoxazol-4-yl)methoxy) naphthalen-2-yl) oxy)nicotinic acid

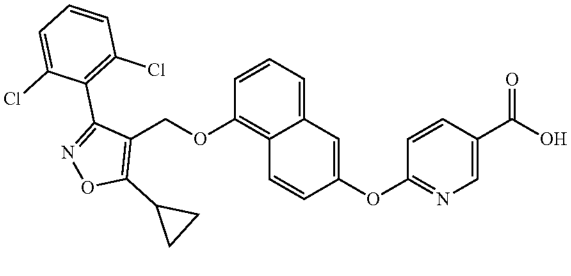 [SMILES: O=C(O)c1ccc(Oc2ccc3c(OCc4c(-c5c(Cl)cccc5Cl)noc4C4CC4)cccc3c2)nc1]

The title compound 36 was prepared according to Route B, following the procedure of Example 32. $^1$H NMR (400 MHz, DMSO-$d_6$) δ 13.19 (s, 1H), 8.65 (d, J=2.4 Hz, 1H), 8.29 (dd, J=8.6, 2.4 Hz, 1H), 7.77 (d, J=9.1 Hz, 1H), 7.65-7.54 (m, 3H), 7.51-7.44 (m, 1H), 7.44-7.34 (m, 2H), 7.19 (dd, J=9.2, 2.4 Hz, 1H), 7.14 (d, J=8.7 Hz, 1H), 7.01 (d, J=7.4 Hz, 1H), 5.09 (s, 2H), 1.31-1.07 (m, 6H). LCMS (ESI): calculated for $C_{29}H_{20}Cl_2N_2O_5$; [M+H]$^+$: 547.1, found: 547.1.

Example 37

Preparation of 6-((6-((5-cyclopropyl-3-(2,6-dichlorophenyl)isoxazol-4-yl)methoxy)-5-fluoronaphthalen-2-yl)oxy)-2-methylnicotinic acid

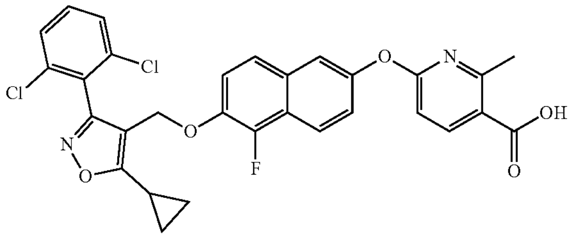 [SMILES: Cc1nc(Oc2ccc3c(F)c(OCc4c(-c5c(Cl)cccc5Cl)noc4C4CC4)ccc3c2)ccc1C(=O)O]

The title compound 37 was prepared according to Route B, following the procedure of Example 32. $^1$H NMR (400 MHz, DMSO-$d_6$) δ 13.01 (s, 1H), 8.24 (d, J=8.6 Hz, 1H), 7.91 (d, J=9.1 Hz, 1H), 7.68 (s, 1H), 7.62 (d, J=9.1 Hz, 1H), 7.58 (d, J=7.9 Hz, 2H), 7.55-7.51 (m, 1H), 7.43-7.34 (m, 2H), 6.92 (d, J=8.6 Hz, 1H), 5.09 (s, 2H), 2.52 (s, 3H), 1.19-1.08 (m, 4H). LCMS (ESI): calculated for $C_{30}H_{21}Cl_2FN_2O_5$; [M+H]$^+$: 579.1, found: 579.1.

Example 38

Preparation of 6-((7-((5-cyclopropyl-3-(2,6-dichlorophenyl)isoxazol-4-yl)methoxy)-8-fluoronaphthalen-2-yl)oxy)nicotinic acid

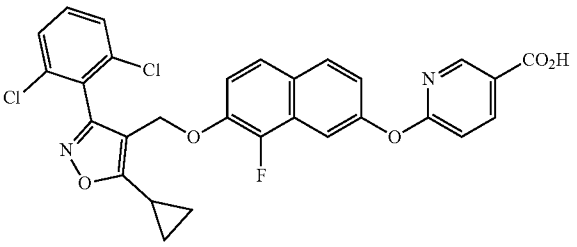 [SMILES: O=C(O)c1ccc(Oc2ccc3ccc(OCc4c(-c5c(Cl)cccc5Cl)noc4C4CC4)c(F)c3c2)nc1]

The title compound 38 was prepared according to Route B, following the procedure of Example 32. $^1$H NMR (400 MHz, DMSO-$d_6$) δ 8.64 (s, 1H), 8.30 (dd, J=8.7, 2.4 Hz, 1H), 7.96 (d, J=8.9 Hz, 1H), 7.70 (d, J=9.0 Hz, 1H), 7.64-7.48 (m, 3H), 7.37 (t, J=8.8 Hz, 1H), 7.27 (d, J=9.2 Hz, 1H), 7.19 (d, J=8.6 Hz, 1H), 6.85 (s, 1H), 5.10 (s, 2H), 2.07-1.89 (m, 1H), 0.94-0.76 (m, 4H). LCMS (ESI): calculated for $C_{29}H_{19}Cl_2FN_2O_5$; [M+H]$^+$: 565.1, found: 565.1.

Example 39

Preparation of 6-((6-((5-cyclopropyl-3-(2,6-dichlorophenyl)isoxazol-4-yl)methoxy)-5-fluoronaphthalen-1-yl)oxy)-2-methylnicotinic acid

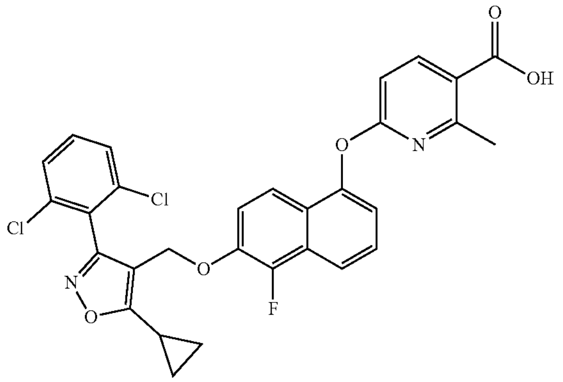 [SMILES: Cc1nc(Oc2cccc3c(F)c(OCc4c(-c5c(Cl)cccc5Cl)noc4C4CC4)ccc23)ccc1C(=O)O]

The title compound 39 was prepared according to Route B, following the procedure of Example 32. $^1H$ NMR (400 MHz, $CDCl_3$) δ 7.94 (dd, J=7.9, 5.0 Hz, 1H), 7.83 (d, J=8.1 Hz, 1H), 7.72-7.59 (m, 2H), 7.58-7.49 (m, 2H), 7.49-7.38 (m, 2H), 7.25-6.97 (m, 1H), 6.67 (d, J=7.9 Hz, 1H), 5.52 (d, J=16.9 Hz, 1H), 5.24 (d, J=16.9 Hz, 1H), 2.70-2.96 (M, 1H), 2.61 (s, 3H), 1.05-0.89 (m, 4H). LCMS (ESI): calculated for $C_{30}H_{21}Cl_2FN_2O_5$; $[M+H]^+$: 579.1, found: 579.1.

Example 40

Preparation of 6((6-((5-cyclopropyl-3-(2,6-dichlorophenyl)isoxazol-4-yl)methoxy)naphthalen-1-yl)oxy)-5-methylpicolinic acid

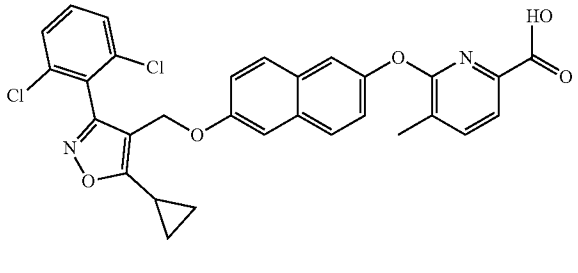 [SMILES: Cc1ccc(C(=O)O)nc1Oc1ccc2cc(OCc3c(-c4c(Cl)cccc4Cl)noc3C3CC3)ccc2c1]

The title compound 40 was prepared according to Route D, following the procedure of Example 22. $^1H$ NMR (400 MHz, $CDCl_3$) δ 8.34 (d, J=8.5 Hz, 1H), 7.79 (d, J=8.2 Hz, 1H), 7.65-7.55 (m, 2H), 7.54-7.49 (m, 2H), 7.50-7.40 (m, 2H), 7.22 (t, J=2.3 Hz, 1H), 7.03-6.93 (m, 2H), 5.44 (s, 2H), 2.95-2.58 (m, 1H), 2.22 (s, 3H), 1.01 (m, 4H). LCMS (ESI): calculated for $C_{30}H_{22}Cl_2N_2O_5$; $[M+H]^+$: 561.1, found: 561.1.

Example 41

Preparation of 6-((2,4-dichloro-6-((5-cyclopropyl-3-(2,6-dichlorophenyl) isoxazol-4-yl)methoxy)naphthalen-1-yl)oxy)nicotinic acid

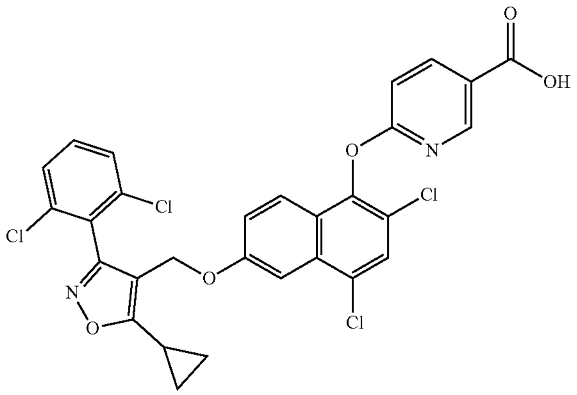 [SMILES: O=C(O)c1ccc(Oc2c(Cl)cc(Cl)c3cc(OCc4c(-c5c(Cl)cccc5Cl)noc4C4CC4)ccc23)nc1]

The title compound 41 was prepared according to Route C, following the procedure of Example 20. $^1H$ NMR (400 MHz, DMSO-$d_6$) δ 13.17 (s, 1H), 8.66 (d, J=2.4 Hz, 1H), 8.34 (dd, J=8.6, 2.4 Hz, 1H), 7.84-7.78 (m, 2H), 7.70-7.65 (m, 2H), 7.64-7.56 (m, 2H), 7.38 (dd, J=9.1, 2.3 Hz, 1H), 7.24 (d, J=8.6 Hz, 1H), 4.92 (s, 2H), 2.45-2.41 (m, 1H), 1.22-1.10 (m, 4H). LCMS (ESI): calculated for $C_{29}H_{18}Cl_4N_2O_5$; $[M+H]^+$: 615.0, found: 615.0.

Example 42

Preparation of 6-((2-chloro-6-((5-cyclopropyl-3-(2,6-dichlorophenyl) isoxazol-4-yl)methoxy)naphthalen-1-yl)oxy)nicotinic acid

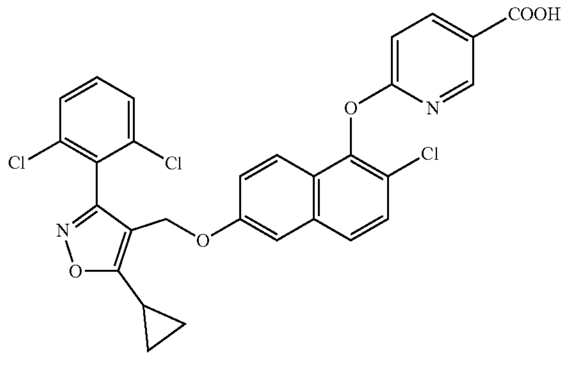 [SMILES: O=C(O)c1ccc(Oc2c(Cl)ccc3cc(OCc4c(-c5c(Cl)cccc5Cl)noc4C4CC4)ccc23)nc1]

The title compound 42 was prepared according to Route C, following the procedure of Example 20. $^1H$ NMR (400 MHz, DMSO-$d_6$) δ 13.15 (s, 1H), 8.65 (d, J=2.4 Hz, 1H), 8.31 (dd, J=8.6, 2.4 Hz, 1H), 7.76 (d, J=2.4 Hz, 1H), 7.70 (d, J=8.8 Hz, 3H), 7.66-7.59 (m, 1H), 7.51 (d, J=8.8 Hz, 1H), 7.44 (d, J=9.1 Hz, 1H), 7.22 (dd, J=9.1, 2.4 Hz, 1H), 7.19 (d, J=8.6 Hz, 1H), 4.87 (s, 2H), 2.46-2.40 (m, 1H), 1.30-1.09 (m, 4H). LCMS (ESI): calculated for $C_{29}H_{19}Cl_3N_2O_5$; $[M+H]^+$: 581.0, found: 581.0.

Example 43

Preparation of 6-((1-chloro-6-((5-cyclopropyl-3-(2,6-dichlorophenyl)isoxazol-4-yl)methoxy)naphthalen-2-yl)oxy)-2-methylnicotinic acid

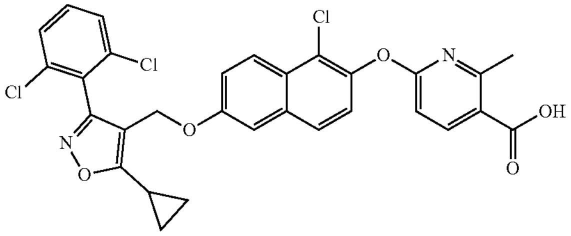 [SMILES: Cc1nc(Oc2ccc3cc(OCc4c(-c5c(Cl)cccc5Cl)noc4C4CC4)ccc3c2Cl)ccc1C(=O)O]

The title compound 43 was prepared according to Route C, following the procedure of Example 20. $^{1}$H NMR (400 MHz, DMSO-$d_6$) δ 12.97 (s, 1H), 8.24 (d, J=8.6 Hz, 1H), 8.00 (d, J=9.2 Hz, 1H), 7.80 (d, J=8.9 Hz, 1H), 7.60 (d, J=8.0 Hz, 2H), 7.55-7.49 (m, 1H), 7.47 (s, 1H), 7.43 (d, J=8.8 Hz, 1H), 7.12 (dd, J=9.2, 2.5 Hz, 1H), 6.95 (d, J=8.6 Hz, 1H), 5.02 (s, 2H), 2.47 (s, 3H), 1.23-1.11 (m, 5H). LCMS (ESI): calculated for $C_{30}H_{21}Cl_3N_2O_5$; $[M+H]^+$: 595.1, found: 595.1.

Example 44

Preparation of 2-((6-((5-cyclopropyl-3-(2,6-dichlorophenyl)isoxazol-4-yl)methoxy)-2-fluoronaphthalen-1-yl)oxy)-4-fluorobenzoic acid

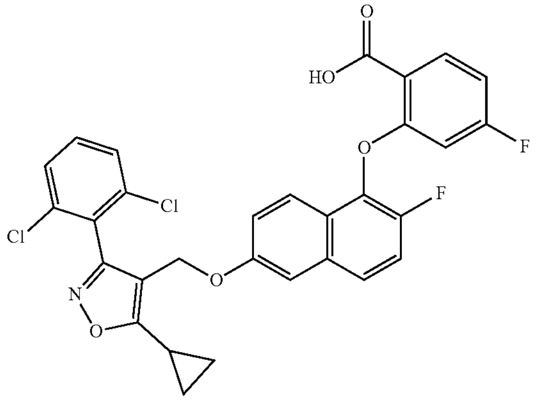 [SMILES: O=C(O)c1ccc(F)cc1Oc1c(F)ccc2cc(OCc3c(-c4c(Cl)cccc4Cl)noc3C3CC3)ccc12]

The title compound 44 was prepared according to Route C, following the procedure of Example 20. $^{1}$H NMR (400 MHz, DMSO-$d_6$) δ 13.04 (s, 1H), 7.82 (t, J=8.6 Hz, 1H), 7.71 (d, J=9.2 Hz, 1H), 7.57 (d, J=7.8 Hz, 2H), 7.52-7.46 (m, 1H), 7.39 (d, J=2.4 Hz, 1H), 7.37-7.31 (m, 1H), 7.15-7.10 (m, 1H), 7.01 (dd, J=9.3, 2.4 Hz, 1H), 6.88 (dd, J=12.3, 2.4 Hz, 1H), 6.73 (dd, J=8.7, 2.3 Hz, 1H), 5.08 (s, 2H), 1.28-1.05 (m, 4H). LCMS (ESI): calculated for $C_{30}H_{19}Cl_2F_2NO_5$; $[M+H]^+$: 582.1, found: 582.1.

Example 45

Preparation of 6-((6-((5-cyclopropyl-3-(2,6-dichlorophenyl)isoxazol-4-yl)methoxy)-2-fluoronaphthalen-1-yl)oxy)-2-methylnicotinic acid

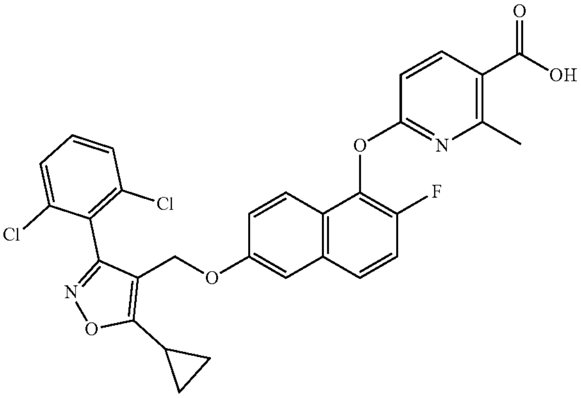 [SMILES: Cc1nc(Oc2c(F)ccc3cc(OCc4c(-c5c(Cl)cccc5Cl)noc4C4CC4)ccc23)ccc1C(=O)O]

The title compound 45 was prepared according to Route C, following the procedure of Example 20. $^{1}$H NMR (400 MHz, DMSO-$d_6$) δ 12.98 (s, 1H), 8.21 (d, J=8.6 Hz, 1H), 7.65 (dd, J=9.3, 1.7 Hz, 1H), 7.57 (d, J=7.7 Hz, 2H), 7.51-7.44 (m, 1H), 7.37 (d, J=2.5 Hz, 1H), 7.35-7.29 (m, 1H), 7.16-7.11 (m, 1H), 6.98 (dd, J=9.2, 2.5 Hz, 1H), 6.87 (d, J=8.5 Hz, 1H), 5.08 (s, 2H), 1.22-1.09 (m, 4H). LCMS (ESI): calculated for $C_{30}H_{21}Cl_2FN_2O_5$; $[M+H]^+$: 579.1, found: 579.1.

Example 46

Preparation of 6((2-chloro-6 ((5-cyclopropyl-3-(2,6-dichlorophenyl) isoxazol-4-yl)methoxy)naphthalen-1-yl)oxy)-2-methylnicotinic acid

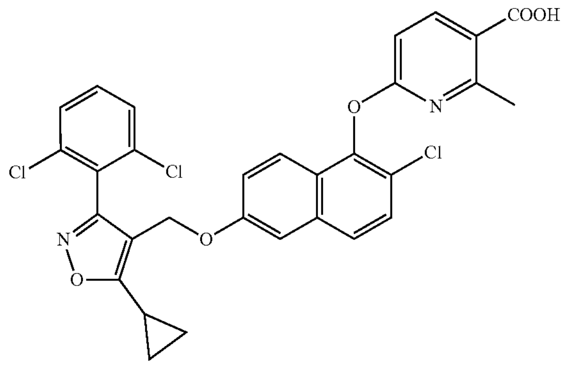 [SMILES: Cc1nc(Oc2c(Cl)ccc3cc(OCc4c(-c5c(Cl)cccc5Cl)noc4C4CC4)ccc23)ccc1C(=O)O]

The title compound 46 was prepared according to Route C, following the procedure of Example 20. $^{1}$H NMR (400 MHz, DMSO-$d_6$) δ 13.03 (s, 1H), 8.25 (d, J=8.6 Hz, 1H), 7.76 (d, J=9.2 Hz, 1H), 7.69 (d, J=8.2 Hz, 1H), 7.58 (d, J=8.0 Hz, 2H), 7.50 (d, J=8.1 Hz, 1H), 7.49-7.44 (m, 1H), 7.18 (d, J=8.2 Hz, 1H), 7.04 (dd, J=9.2, 2.4 Hz, 1H), 6.95 (d, J=8.6 Hz, 1H), 5.13 (s, 2H), 2.59-2.54 (m, 1H), 2.48 (s, 3H), 1.27-1.15 (m, 4H). LCMS (ESI): calculated for $C_{30}H_{21}Cl_3N_2O_5$; $[M+H]^+$: 595.1, found: 595.1.

Example 47

Preparation of 6-((6-((5-cyclopropyl-3-(2,6-dichlorophenyl)isoxazol-4-yl)methoxy)-2-fluoronaphthalen-1-yl)oxy)-5-methylnicotinic acid

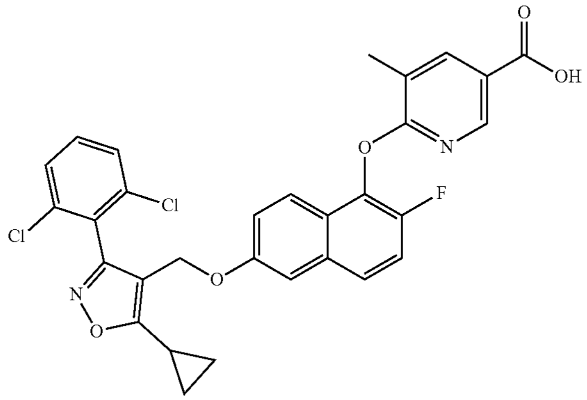 [SMILES: Cc1cc(C(=O)O)cnc1Oc1c(F)ccc2cc(OCc3c(-c4c(Cl)cccc4Cl)noc3C3CC3)ccc12]

The title compound 47 was prepared according to Route C, following the procedure of Example 20. $^1$H NMR (400 MHz, DMSO-$d_6$) δ 13.09 (s, 1H), 8.32 (s, 1H), 8.21 (s, 1H), 7.67-7.55 (m, 3H), 7.55-7.45 (m, 1H), 7.39 (s, 1H), 7.37-7.30 (m, 1H), 7.20-7.09 (m, 1H), 7.03-6.93 (m, 1H), 5.09 (s, 2H), 2.48 (s, 3H), 1.41-1.00 (m, 5H). LCMS (ESI): calculated for $C_{30}H_{21}Cl_2FN_2O_5$; $[M+H]^+$: 579.1, found: 579.1.

Example 48

Preparation of 2-((6-((5-cyclopropyl-3-(2,6-dichlorophenyl)isoxazol-4-yl)methoxy)-2-fluoronaphthalen-1-yl)oxy)nicotinic acid

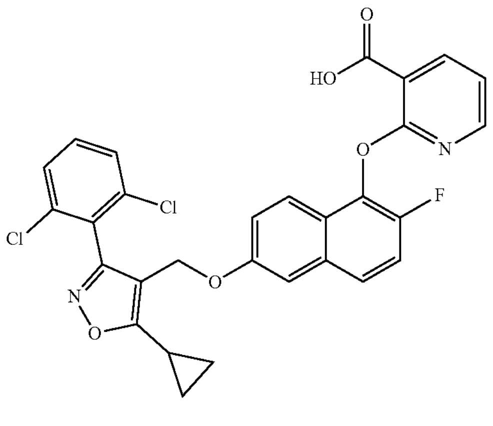 [SMILES: O=C(O)c1cccnc1Oc1c(F)ccc2cc(OCc3c(-c4c(Cl)cccc4Cl)noc3C3CC3)ccc12]

The title compound 48 was prepared according to Route C, following the procedure of Example 20. $^1$H NMR (400 MHz, DMSO-$d_6$) δ 8.29-8.27 (m, 1H), 8.22 (d, J=8.5 Hz, 1H), 8.09-8.06 (m, 1H), 7.53-7.47 (m, 3H), 7.46-7.42 (m, 1H), 7.30-7.25 (m, 2H), 7.08-7.05 (m, 1H), 6.96 (dd, J=8.4, 2.4 Hz, 1H), 5.44 (s, 2H), 2.79 (p, J=6.4 Hz, 1H), 1.20-1.09 (m, 5H). LCMS (ESI): calculated for $C_{29}H_{19}C_{12}FN_2O_5$; $[M+H]^+$: 565.1, found: 565.1.

Example 49

Preparation of 2-((6-((5-cyclopropyl-3-(2,6-dichlorophenyl)isoxazol-4-yl)methoxy)-2-fluoronaphthalen-1-yl)oxy)-4-fluorobenzoic acid

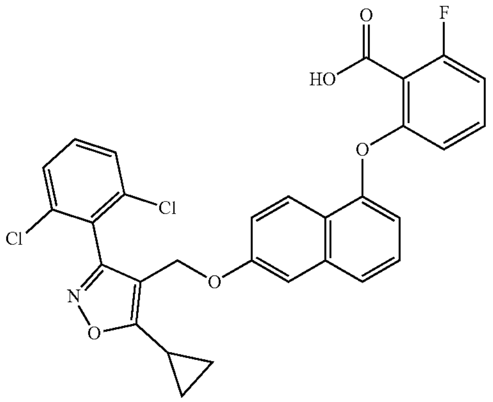 [SMILES: O=C(O)c1c(F)cccc1Oc1cccc2cc(OCc3c(-c4c(Cl)cccc4Cl)noc3C3CC3)ccc12]

The title compound 49 was prepared according to Route D, following the procedure of Example 22. $^1$H NMR (400 MHz, DMSO-$d_6$) δ 13.62 (s, 1H), 7.84 (d, J=9.2 Hz, 1H), 7.63-7.55 (m, 3H), 7.54-7.49 (m, 1H), 7.42 (t, J=7.9 Hz, 1H), 7.40-7.32 (m, 2H), 7.06 (t, J=8.8 Hz, 1H), 6.96 (dd, J=9.1, 2.5 Hz, 1H), 6.90 (d, J=7.5 Hz, 1H), 6.56 (d, J=8.4 Hz, 1H), 4.99 (s, 2H), 1.23-1.09 (m, 4H). LCMS (ESI): calculated for $C_{30}H_{20}Cl_2FN_2O_5$; $[M+H]^+$: 564.1, found: 564.1.

BIOLOGY EXAMPLES

Example A

FXR Agonist Binding Ability

Evaluation of the activation effect of the compound of the present invention with regard to the binding of FXR to its co-stimulatory factor SRC-1 was conducted by using time-resolved analytical techniques. The results are listed in Table 1.

Experimental Materials

1. Protein: glutathione-S-transferase (GST)-labeled human FXR protein (Invitrogen)
2. Coactivator: Fluorescein-labeled steroid receptor coactivator (SRC2-2) (Invitrogen)
3. Detection reagent: LanthaScreen Time-Resolved Fluorescence Analysis Kit (Invitrogen)

Experimental Method

1. The compound was prepared into a 10 mM DMSO stock solution and stored in a −20° C. refrigerator for a long time.
2. The compound was diluted to 1 mM before the experiment, and then the compound was diluted 3-fold to 10 concentration points using DMSO. Then use buffer G (Invitrogen, PV4553) to dilute these 10 concentration points by 50 times to become a working fluid. Add 10 μl of each working solution to each well of a 384-well plate.

3. Prepare a human FXR protein solution (final concentration 20 nM) in chilled buffer G and add 5 μl of human FXR protein solution to each well of a 384-well plate.
4. Prepare a mix of buffer G containing 2 μM fluorescein-labeled steroid receptor coactivator and 20 nM GST antibody.
5. Add 5 μl of the mixture prepared in Step 4 to a 384-well plate.
6. Centrifuge the 384-well plate at 1000 g for 1 minute.
7. Incubate for 1 hour at room temperature in the dark.
8. Read the 384-well plate at 520 nm and 495 nm on an Envision 2104 plate reader.
9. Calculate the $EC_{50}$ value of the activation effect of the compound.

Example B

FXR Agonist Transactivation Ability

Evaluation of the ability of the compound of the present invention to promote FXR transactivation was conducted by using luciferase reporter gene expression technology. The results are listed in Table 1.

Experimental Materials

1. Cell line: HEK293T (Invitrogen)
2. Expression plasmid: pBIND-hFXR-LBD-GAL4 (Promega), pGL4.35-luciferase (Promega)
3. Cell culture medium: 10% serum and penicillin/streptomycin double antibody in DMEM medium
4. Detection reagent: Steady-Glo fluorescence detection system (Promega).
5. Transfection reagent: TransIT-293 Transfection Reagent (MIRUS BIO)

Experimental Method

1. The compound was prepared into a 10 mM DMSO stock solution and stored in a −20° C. refrigerator for a long time.
2. Resuscitation HEK293T cells were seeded in 10 cm culture dishes at a concentration of $5.5\times10^6$ and incubated for 16 hours at 37° C. in a 5% $CO_2$ incubator.
3. Return the transfection reagent to room temperature before transfection. The Trans-IT solution was added dropwise to Opti-MEM, and mixed by inversion for 5 minutes; the expression plasmid was added, mixed by inversion, and incubated at room temperature for 20 minutes.
4. Add the transfection mixture from Step 3 to the prepared 10 cm dish in Step 2 and incubate for 5-6 hours in a 5% $CO_2$ incubator.
5. Dilute the compound 3 folds to 10 concentration points using DMSO; add 25 nl of compound per well in a 384-well plate using an Echo 550 sonic pipette; add HEK293T cells to the 384-well plate at a concentration of 15,000 cells/well; 37° C. incubate for 16-20 hours in a 5% $CO_2$ incubator.
6. Add 25 μl of Steady-Glo Fluorescent Reagent to each well and read the fluorescence on an Envision 2104 plate reader.
7. Calculate the $EC_{50}$ value of the activation of the compound.

TABLE 1

FXR agonist binding activity values grouped in the following range: A indicates EC50 < 50 nM; B indicates 50 < EC50 < 500 nM; C indicates EC50 > 500 nM.

| Compound | FXR binding activity |
|---|---|
| Compound 1 | B |
| Compound 2 | B |
| Compound 3 | C |
| Compound 4 | B |
| Compound 5 | C |
| Compound 6 | B |
| Compound 7 | C |
| Compound 8 | B |
| Compound 9 | B |
| Compound 10 | B |
| Compound 11 | A |
| Compound 12 | A |
| Compound 13 | B |
| Compound 14 | B |
| Compound 15 | B |
| Compound 16 | A |
| Compound 17 | C |
| Compound 18 | B |
| Compound 19 | C |
| Compound 20 | B |
| Compound 21 | B |
| Compound 22 | A |
| Compound 23 | C |
| Compound 24 | A |
| Compound 25 | B |
| Compound 26 | A |
| Compound 27 | A |
| Compound 28 | A |
| Compound 29 | B |
| Compound 30 | A |
| Compound 31 | A |
| Compound 32 | A |
| Compound 33 | B |
| Compound 34 | B |
| Compound 35 | A |
| Compound 36 | B |
| Compound 37 | B |
| Compound 38 | A |
| Compound 39 | A |
| Compound 40 | C |
| Compound 41 | C |
| Compound 42 | C |
| Compound 43 | B |
| Compound 44 | A |
| Compound 45 | A |
| Compound 46 | B |
| Compound 47 | A |
| Compound 48 | A |
| Compound 49 | B |

TABLE 2 cell activity values grouped in the following range: A indicates EC50 < 200 nM; B indicates 500 < EC50 < 1000 nM; C indicates EC50 > 1000 nM.

| Compound | Cell activity |
|---|---|
| Compound 1 | A |
| Compound 2 | C |
| Compound 3 | C |
| Compound 4 | C |
| Compound 5 | C |
| Compound 6 | C |
| Compound 7 | C |
| Compound 8 | B |
| Compound 9 | C |
| Compound 10 | A |
| Compound 11 | B |
| Compound 12 | C |
| Compound 13 | C |

TABLE 2-continued

| cell activity values grouped in the following range: A indicates EC50 < 200 nM; B indicates 500 < EC50 < 1000 nM; C indicates EC50 > 1000 nM. | |
|---|---|
| Compound | Cell activity |
| Compound 14 | C |
| Compound 15 | C |
| Compound 16 | C |
| Compound 17 | C |
| Compound 18 | C |
| Compound 19 | C |
| Compound 20 | B |
| Compound 21 | A |
| Compound 22 | A |
| Compound 23 | C |
| Compound 24 | A |
| Compound 25 | C |
| Compound 26 | A |
| Compound 27 | A |
| Compound 28 | A |
| Compound 29 | B |
| Compound 30 | A |
| Compound 31 | A |
| Compound 32 | A |
| Compound 33 | A |
| Compound 34 | A |
| Compound 35 | A |
| Compound 36 | C |
| Compound 37 | C |
| Compound 38 | B |
| Compound 39 | A |
| Compound 40 | C |
| Compound 41 | C |

Example C

Mouse Pharmacokinetic Studies

Typical PK study procedure. For i.v. PK studies, a group of three fasted Male CD-1 mice were dosed with the compound (2.0 mg/kg, 0.50 mg/mL in 5% solutol in saline, clear solution), and 0.02 mL blood was collected at 0.0830, 0.250, 0.500, 1.00, 2.00, 4.00, 8.00, 24.0 h. For PO PK studies, a group of three fasted Male CD-1 mice were dosed with the compound (10 mg/kg, 1 mg/mL in 5% solutol in saline, clear solution), and 0.02 mL blood was collected at 0.250, 0.500, 1.00, 2.00, 4.00, 6.00, 8.00, 24.0 h. The blood was collected into EP tubes (containing EDTA K20.85-1.15 mg) and centrifuged at 3,000 g or 3,200 g at 4° C. for 10 min) and plasma was isolated and divided into two vials. One was used for bioanalysis and one was kept as backup. The samples were kept at −60° C. or below, until being analyzed by LC MS/MS. The samples were analyzed with AB SCIEX INSTRUMENTS LC-MS/MS AU-Triple Quad 6500 Plus and data were processed with Phoenix WinNonlin 6.3 (IV-noncompartmental model and PO-noncompartmental model).

PK Results

Pharmacokinetic results in mouse is shown in Table 3.

TABLE 3

| Mouse Pharmacokinetic results | | | | | | | | |
|---|---|---|---|---|---|---|---|---|
| | IV | | | | PO | | | |
| Compound | T½ (h) | Cl (mL/min/kg) | Vd (L/kg) | AUC $_{0-t}$ (ng•h/mL) | Cmax (ng/ml) | Tmax (h) | AUC $_{0-t}$ (ng•h/mL) | F (%) |
| 1 | 0.85 | 47.4 | 1.75 | 705 | 641 | 0.83 | 1159 | 33% |
| 10 | 1.6 | 9.26 | 0.66 | 3553 | 5503 | 0.417 | 9361 | 52.6% |
| 11 | 1.44 | 6.66 | 0.294 | 4977 | 5726 | 0.5 | 8329 | 33.3% |
| 21 | 1.28 | 35.8 | 1.75 | 969 | 1480 | 0.5 | 2220 | 46.2% |
| 22 | 0.837 | 73.8 | 1.84 | 448 | 894 | 0.5 | 718 | 32% |
| 24 | 0.94 | 105 | 2.94 | 330 | 209 | 0.3 | 198 | 12% |
| 26 | 0.62 | 35 | 0.745 | 969 | 900 | 0.5 | 830 | 17% |
| 27 | 1.61 | 19.7 | 0.897 | 1690 | 2078 | 0.5 | 2785 | 33.2% |
| 28 | 0.977 | 28.4 | 0.663 | 1177 | 2130 | 0.5 | 1743 | 29.9% |
| 31 | 0.614 | 110 | 2.77 | 304 | 133 | 0.333 | 140 | 9.74% |
| 32 | 1.03 | 24 | 1.36 | 1395 | 1395 | 0.5 | 3810 | 54.7% |
| 44 | 1.23 | 60.4 | 2.06 | 559 | 384 | 0.933 | 646 | 23.7% |
| 45 | 1.4 | 22.1 | 1.04 | 1501 | 627 | 1.00 | 1140 | 15.7% |
| 47 | 0.638 | 22.2 | 0.495 | 1500 | 2146 | 0.5 | 2140 | 28.6% |

TABLE 2-continued

| cell activity values grouped in the following range: A indicates EC50 < 200 nM; B indicates 500 < EC50 < 1000 nM; C indicates EC50 > 1000 nM. | |
|---|---|
| Compound | Cell activity |
| Compound 42 | C |
| Compound 43 | B |
| Compound 44 | A |
| Compound 45 | A |
| Compound 46 | A |
| Compound 47 | A |
| Compound 48 | A |
| Compound 49 | C |

Example D

Therapeutic efficacy of FXR compounds was evaluated in STZ+DEN+HFD induced NASH model in male C57BL/6 mice. Briefly, newborn male C57BL/6 mice were injected with streptozocin (STZ) at Week 2 to introduce diabetes and diethylnitrosamine (DEN) at Week 4 to promote liver fibrosis. Mice receiving neither STZ nor DEN were used as negative control (Group 1, n=12) and were fed with normal diet. At Week 6, 60 diabetic mice were selected (blood glucose>12 mmol/L after 6 h of fasting) and were fed with high fat diet (HFD, diet that contains 60 kcal % fat). After one week on HFD, animals were randomly assigned into 5 groups based on body weight: Group 2 (n=12), disease model group, no compound treatment; Group 3 (n=10), positive control group, treated with OCA (30 mg/kg); Group 4 (n=12), treated with Compound 1 (3 mg/kg); Group 5 (n=12), treated with Compound 1 (10 mg/kg); Group 6 (n=12), treated with Compound 1 (30 mg/kg). OCA and Compounds 1 were PO QD, for 7 weeks. On the day after last dose, all animals were euthanized and liver tissues were fixed with formalin for pathological evaluation.

Figure 2:
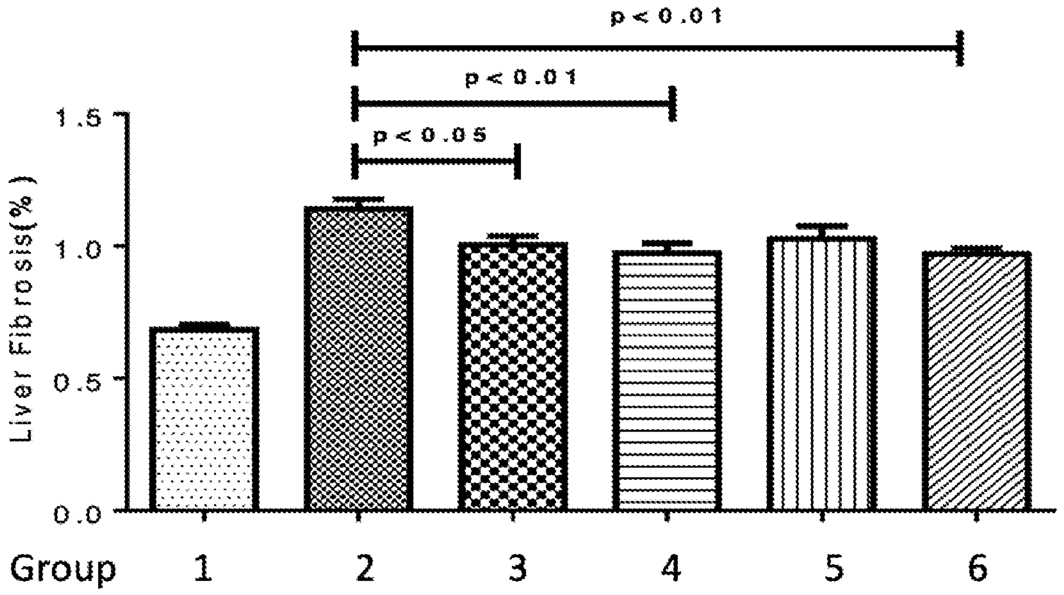
FIG. 2 shows reduction of liver fibrosis after Compound 1 treatment in STZ+DEN+HFD mice disease model.

FIG. 1 shows reduction of NAS score after Compound 1 treatment in STZ+DEN+HFD mice disease model. FIG. 2 shows reduction of liver fibrosis after Compound 1 treatment in STZ+DEN+HFD mice disease model. As shown in FIG. 1, treatment of Compound 1 at low dose (3 mg/kg), medium dose (10 mg/kg), and high dose (30 mg/kg), respectively, showed a dose dependent decrease in hepatocyte steatosis ($p<0.001$). The 30 mg/kg group showed a decreased NAS score by 46.2% as compared with the model group. The positive control group (OCA 30 mg/kg) also showed decrease in NAS score. As shown in FIG. 2, treatment of Compound 1 at low (3 mg/kg) and high doses (30 mg/kg) significantly inhibited the progress of liver fibrosis and the 30 mg/kg doses group lowered cirrhosis percentage by 15.2%. In conclusion, after 7-week treatment at 30 mg/kg per day, Compound 1 significantly decreases in NAS score and liver fibrosis.

Example E

Therapeutic efficacy of FXR compounds was evaluated in DEN+HFD+CHOL induced NASH model in male SD rats.

Newborn male rats received DEN injection at Week 2 after birth to generate NASH model. Negative control animals (Group 1, n=10) received no DEN injection. At Week 4, 50 rats that received DEN injections started HFD+CHOL diet (60 kcal % Fat+1.25% Cholesterol+0.5% cholate) for 8 weeks, while negative control animals were still on normal diet. At Week 5, DEN treated rats were randomly assigned into 5 groups (Group 2-6) based on body weight. Disease Group (Group 2, n=10), received no treatment; OCA group (Group 3, n=10) received OCA at 30 mg/kg. Group 4-6 (n=10 each) received Compound 1 at low (3 mg/kg), medium (3 mg/kg), and high doses (3 mg/kg). OCA and Compound 1 were given PO QD, for 7 weeks. On the day after last dose, all animals were euthanized and liver tissues were fixed with formalin for pathological evaluation.

Figure 3:
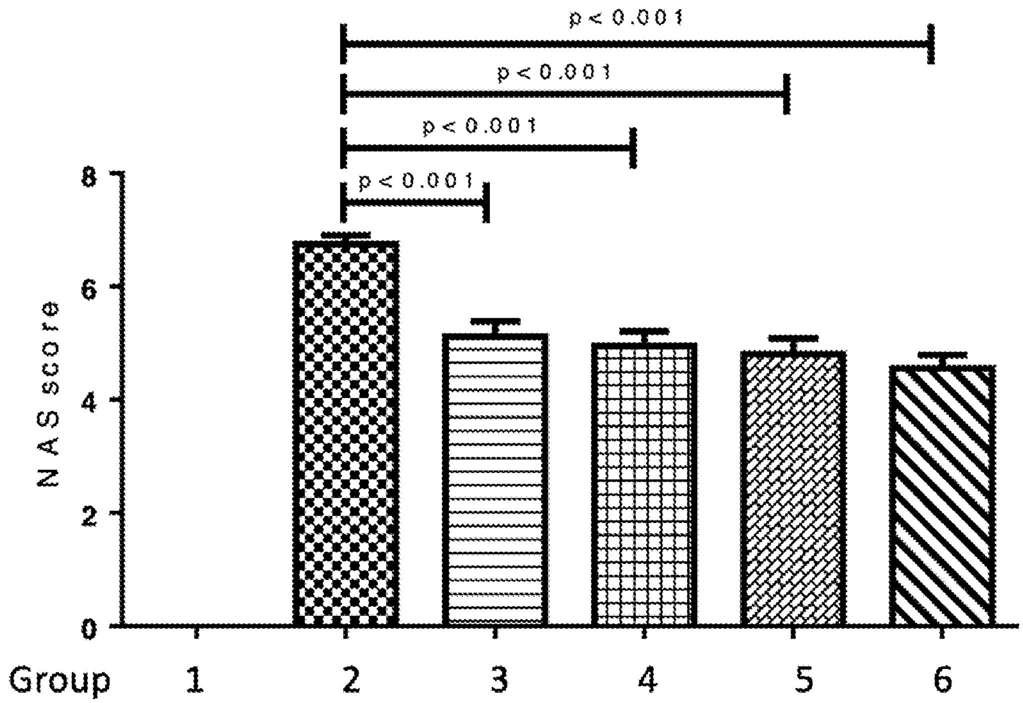
FIG. 3 shows reduction of NAS score after Compound 1 treatment in diethylnitrosamine (DEN)+high fat diet (HFD)+cholesterol/cholate (CHOL) treated rats.
Figure 4:
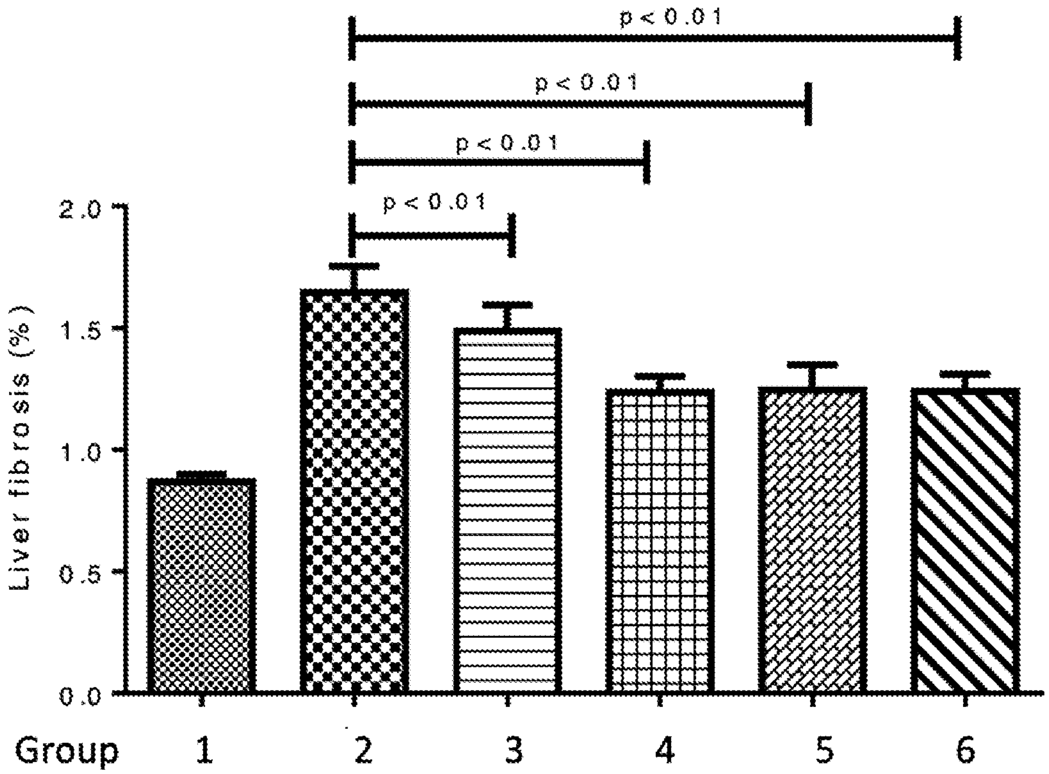
FIG. 4 shows reduction of liver fibrosis after Compound 1 treatment in DEN+HFD+CHOL treated rats.

FIG. 3 shows reduction of NAS score after Compound 1 treatment in DEN+HFD+CHOL treated rats. FIG. 4 shows reduction of liver fibrosis after Compound 1 treatment in DEN+HFD+CHOL treated rats.

As shown in FIG. 3, treatment of Compound 1 at low (3 mg/kg), medium (10 mg/kg), and high doses (30 mg/kg), respectively, showed a dose dependent decrease in NAS score (all $p<0.001$). The NAS score of 30 mg/kg group was lowered by 42.9% as compared to the model group (Group 2). The positive control (OCA 30 mg/kg) also showed a decrease in NAS score ($p<0.001$). As shown in FIG. 4, treatment of Compound 1 at low (3 mg/kg), medium (10 mg/kg), and high doses (30 mg/kg), significantly inhibited the progress of liver fibrosis (both $p<0.01$). Treatment at 30 mg/kg group lowered cirrhosis percentage by 28.0%.

The invention claimed is:

1. A compound for modulating the activity of FXR having a structure of formula (I), or a pharmaceutically acceptable salt, an ester or a stereoisomer thereof:

(I)

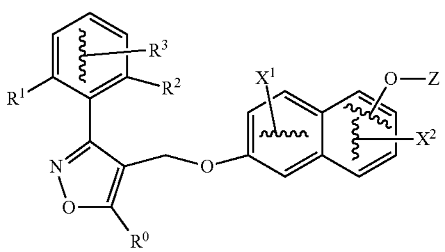

wherein:

$R^1$, $R^2$ and $R^3$ are independently selected from H, halogen, unsubstituted or halogen substituted $C_{1-6}$ alkyl and unsubstituted or halogen substituted $C_{1-6}$ alkoxy, provided that at least one of $R^1$, $R^2$ and $R^3$ is not hydrogen, $R^0$ is selected from unsubstituted or halogen substituted $C_{1-6}$ alkyl, $C_{3-6}$ cycloalkyl and $C_{4-7}$ alkylcycloalkyl;

$X^1$ and $X^2$ are independently selected from H and halogen;

moiety —O—Z attaches to the naphthalene ring, wherein Z is a residue selected from 5-10 membered aryl and 5-10 membered heteroaryl optionally having one or more hetero atoms selected from N, O and S, wherein the 5-10 membered aryl or 5-10 membered heteroaryl is substituted by $R^4$ and is optionally further substituted by $R^5$;

wherein $R^4$ is selected from —COOH, —$CH_2COOH$, —$NHSO_2CF_3$, —$SO_2NH$—$C_{1-6}$ alkyl, —$SO_3H$, —$CONHSO_2$—$C_{1-6}$ alkyl, —$CONHSO_2$—$C_{3-6}$ cycloalkyl, —$CONHSO_2$-5-10 membered aryl and —$CONHSO_2$-5-10 membered aryl substituted by $C_{1-6}$ alkyl at the aryl, and wherein $R^5$ is selected from H, $C_{1-6}$ alkyl, halogen, $C_{1-6}$ haloalkyl, —O—($C_{1-6}$ alkyl) and —NH—($C_{1-6}$ alkyl).

2. The compound according to claim 1, or a pharmaceutically acceptable salt, an ester or a stereoisomer thereof, wherein $R^1$, $R^2$ and $R^3$ are independently selected from H, halogen and $C_{1-3}$ perfluoroalkoxy, and $R^0$ is selected from isopropyl and cyclopropyl.

3. The compound according to claim 2, or a pharmaceutically acceptable salt, an ester or a stereoisomer thereof, wherein $R^1$, $R^2$ and $R^3$ are independently selected from H, Cl, F and —O—$CF_3$.

4. The compound according to claim 1, or a pharmaceutically acceptable salt, an ester or a stereoisomer thereof, wherein both of $R^1$ and $R^2$ are Cl, and $R^3$ is selected from H, F and —O—$CH_3$; or $R^1$ is —O—$CF_3$, and both of $R^2$ and $R^3$ are H.

5. The compound according to claim 1, or a pharmaceutically acceptable salt, an ester or a stereoisomer thereof, wherein Z is a phenyl which is substituted by $R^4$ and is optionally substituted by $R^5$; or Z is a 5-10 membered heteroaryl having one or more hetero atoms selected from N, O and S, which is substituted by $R^4$ and is optionally substituted by $R^5$.

6. The compound according to claim 5, or a pharmaceutically acceptable salt, an ester or a stereoisomer thereof, wherein Z is a 5-6 membered heteroaryl having one or more hetero atoms selected from N, O and S, which is substituted by $R^4$ and is optionally substituted by $R^5$.

7. The compound according to claim 1, or a pharmaceutically acceptable salt, an ester or a stereoisomer thereof, wherein Z is a pyridyl, which is substituted by $R^4$ and is optionally substituted by $R^5$.

8. The compound according to claim 1, or a pharmaceutically acceptable salt, an ester or a stereoisomer thereof, wherein $R^4$ is selected from —COOH, —$CH_2COOH$, —$CONHSO_2$—$C_{1-6}$ alkyl and —$CONHSO_2$-$C_{3-6}$ cycloalkyl.

9. The compound according to claim 8, or a pharmaceutically acceptable salt, an ester or a stereoisomer thereof, wherein $R^4$ is —COOH or —$CH_2COOH$.

10. The compound according to claim 1, or a pharmaceutically acceptable salt, an ester or a stereoisomer thereof, wherein $R^5$ is selected from H, $C_{1-3}$ alkyl and halogen.

11. The compound according to claim 1, or a pharmaceutically acceptable salt, an ester or a stereoisomer thereof, wherein Z is pyridyl; $R^4$ is —COOH; and $R^5$ is H or halogen.

12. The compound according to claim 1, or a pharmaceutically acceptable salt, an ester or a stereoisomer thereof, wherein each halogen present in the compound is fluoro or chloro.

13. The compound according to claim 1, or a pharmaceutically acceptable salt, an ester or a stereoisomer thereof, wherein the compound is selected from the group consisting of:

1

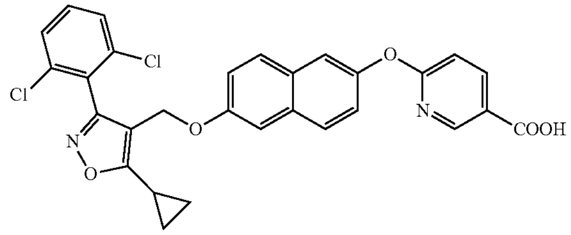

2

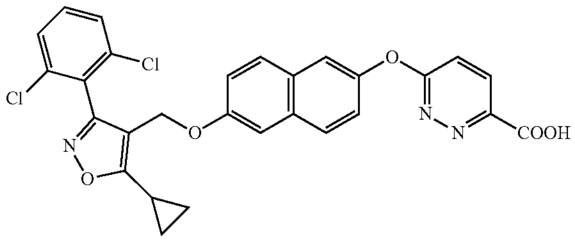

3

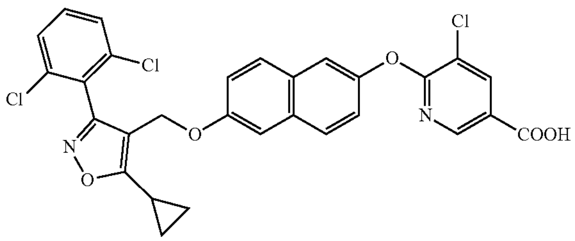

4

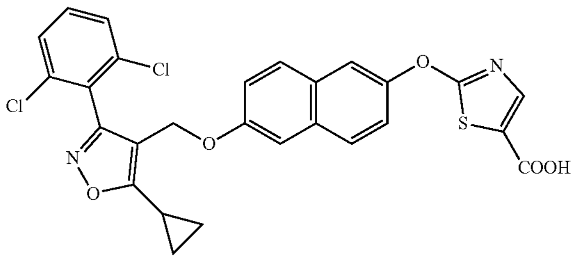

-continued

5

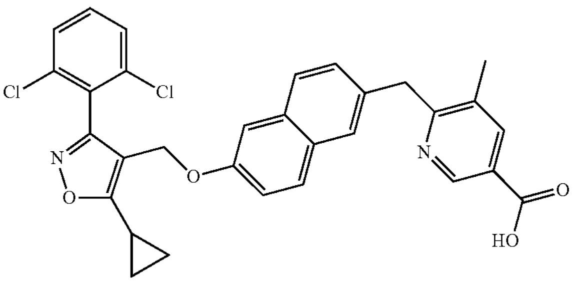

6

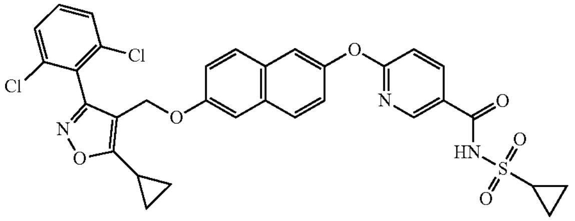

7

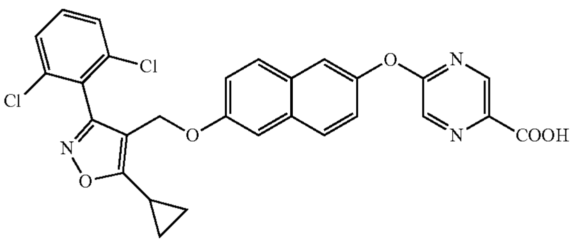

8

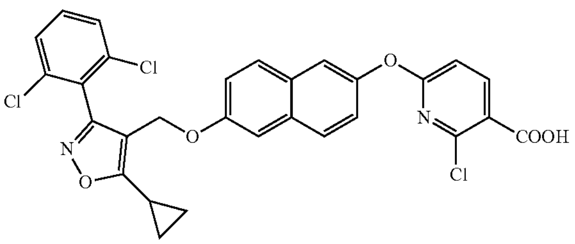

9

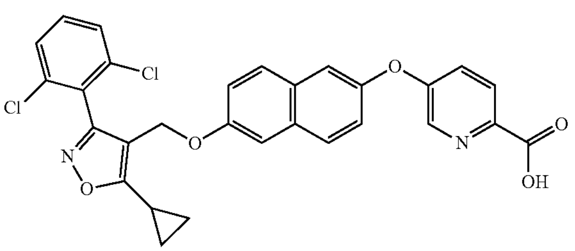

10

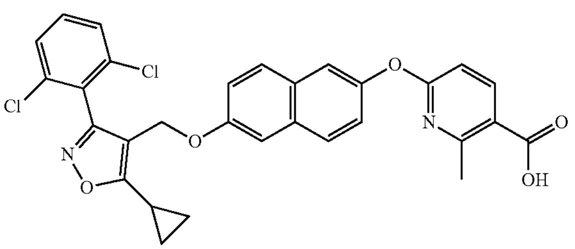

11
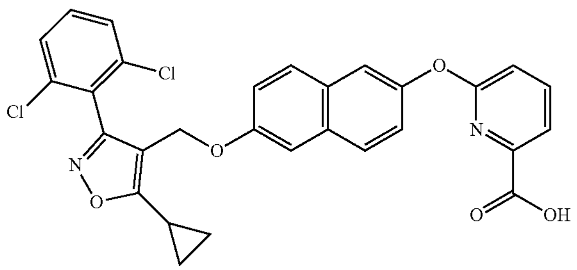
12
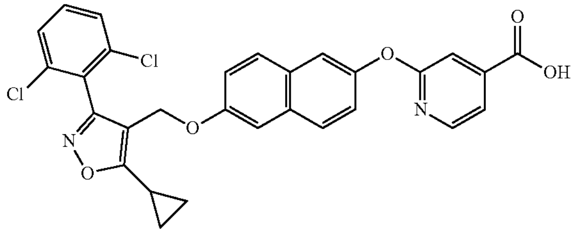
13
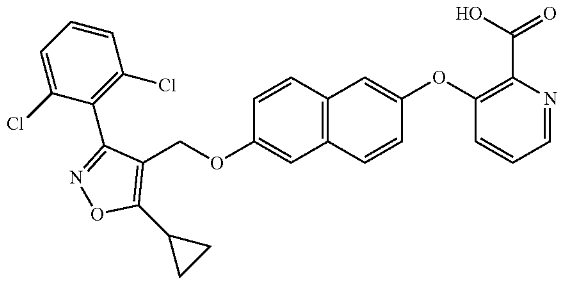
14
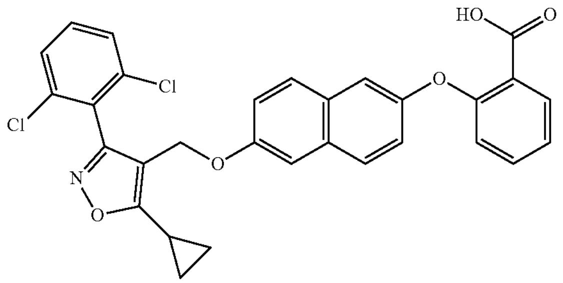
15
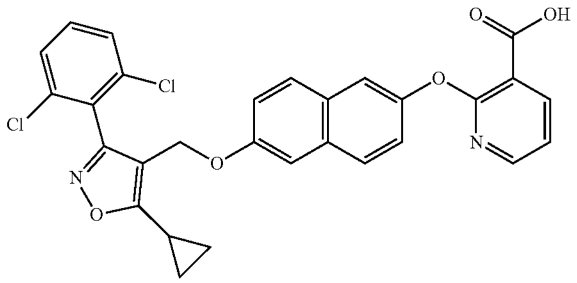
16
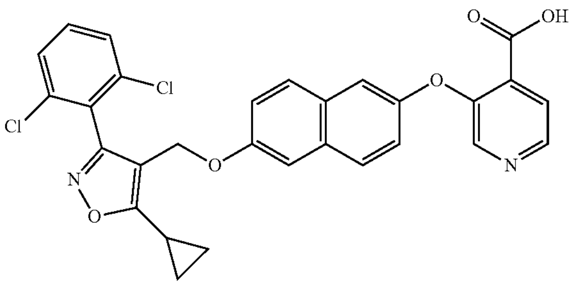
17
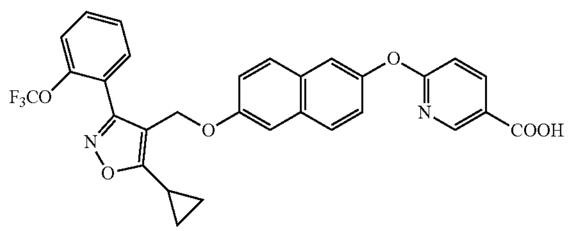
18
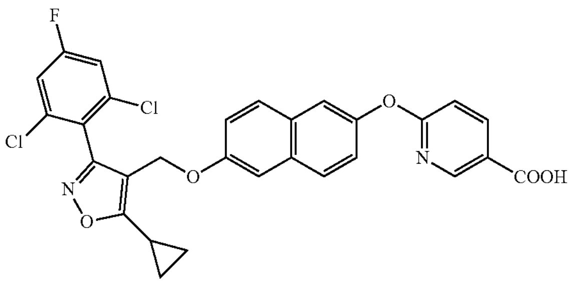
19
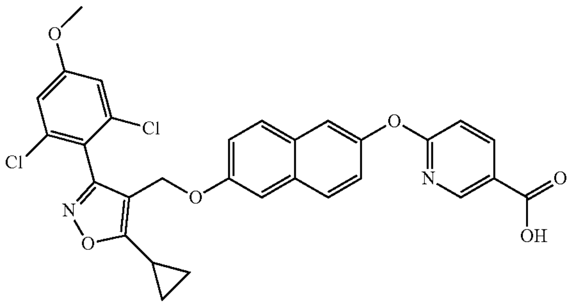
20
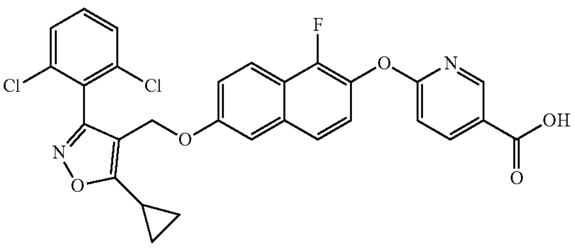

-continued
21
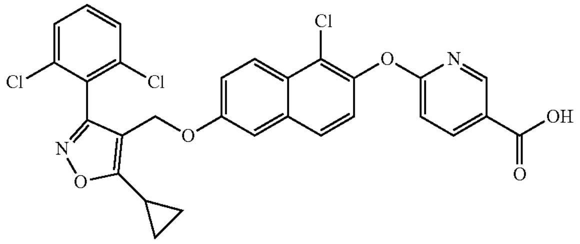
22
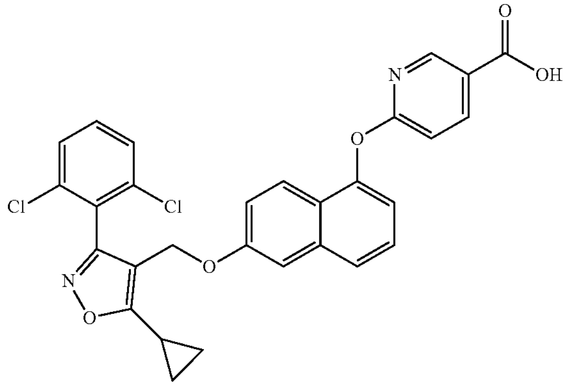
23
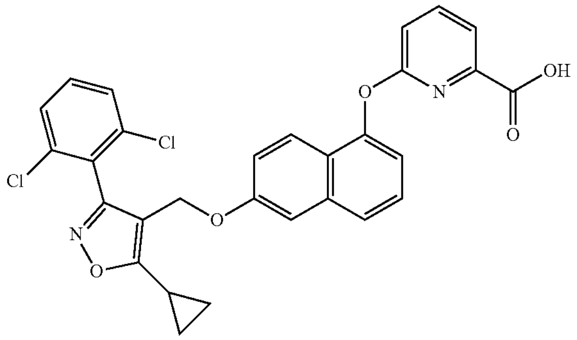
24
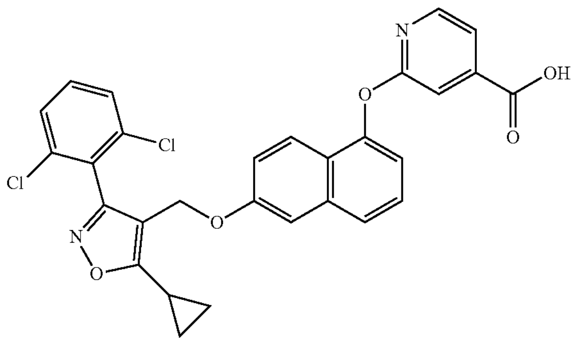
-continued
25
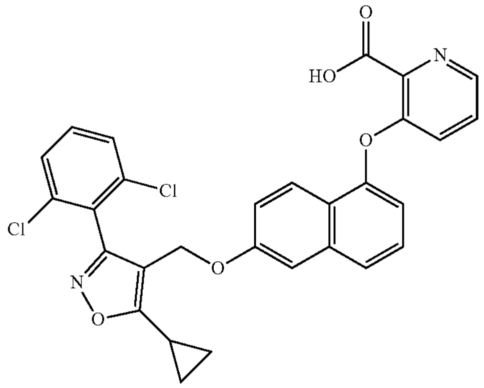
26
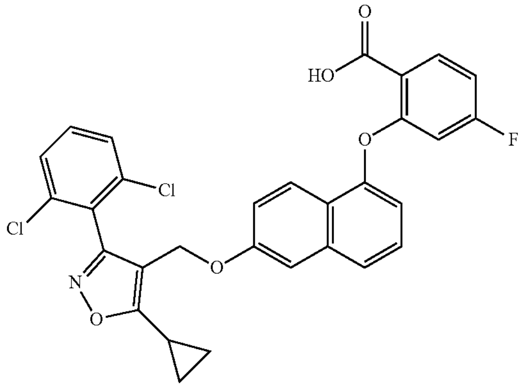
27
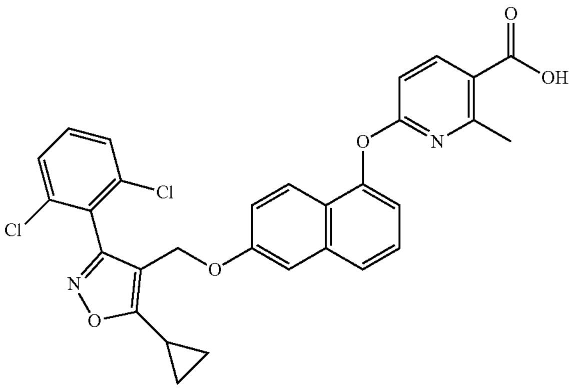
28
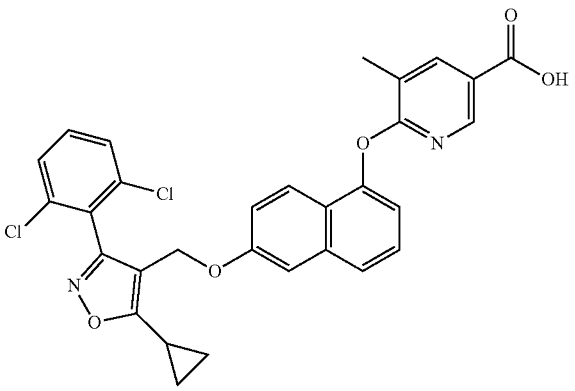

-continued
29
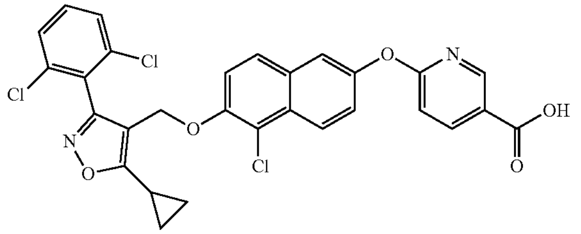
30
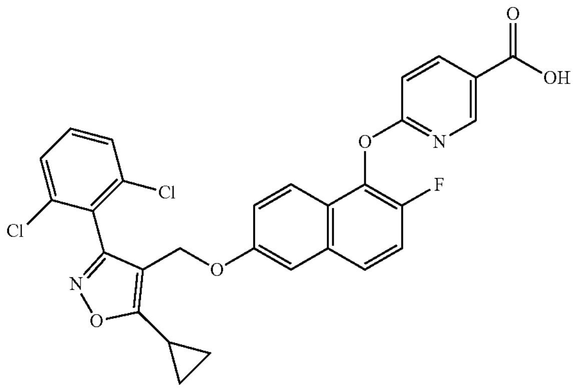
31
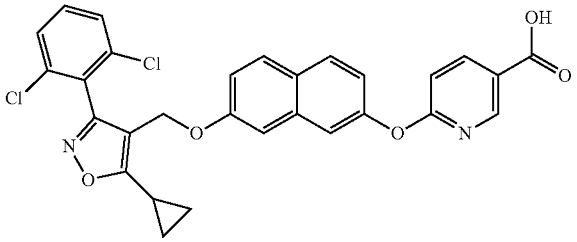
32
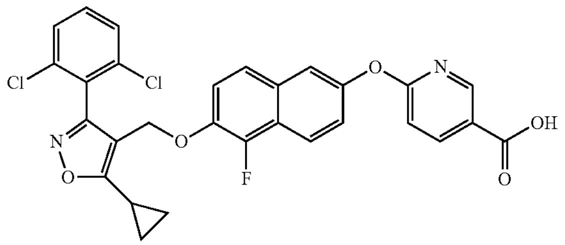
33
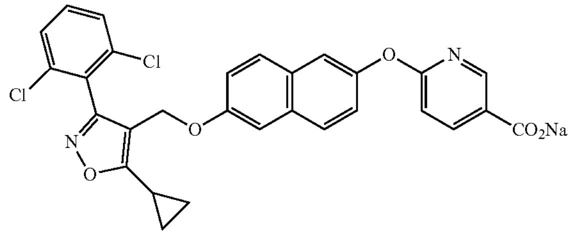
-continued
34
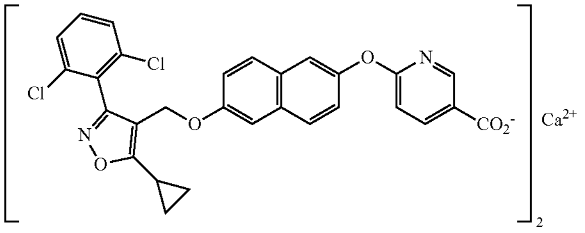
35
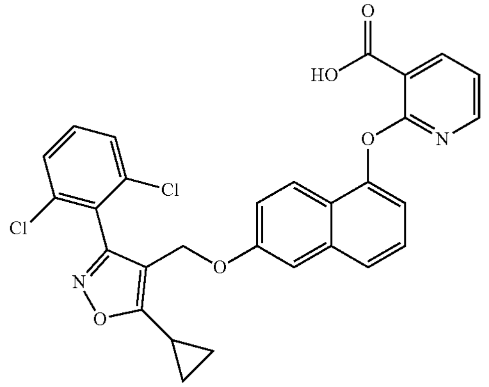
36
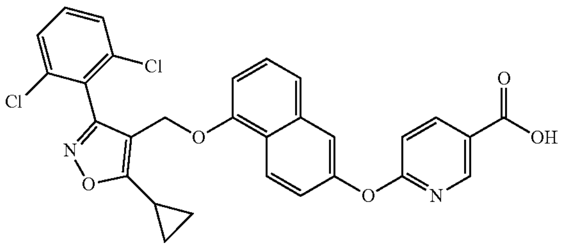
37
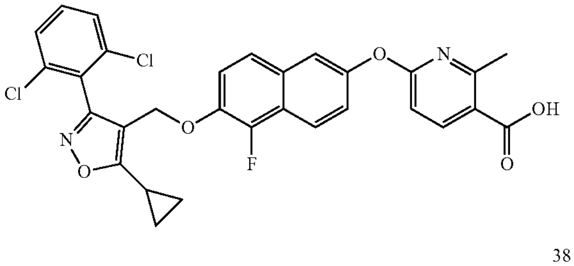
38
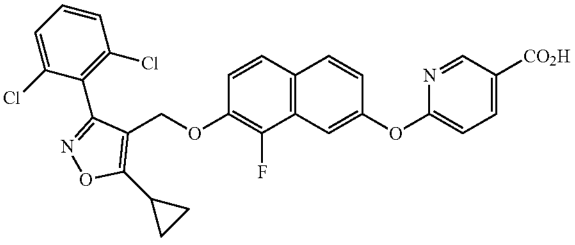

-continued
39
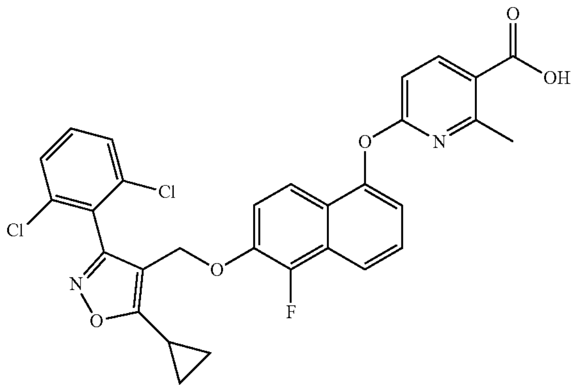
40
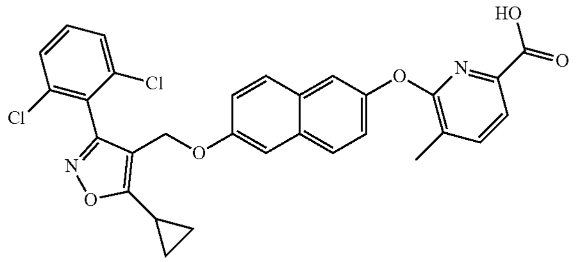
41
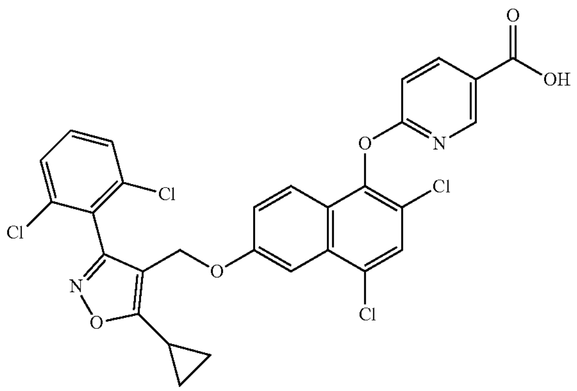
42
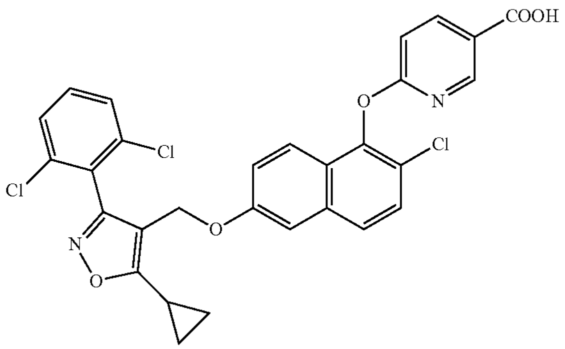
-continued
43
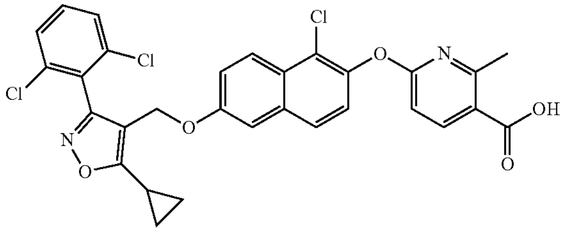
44
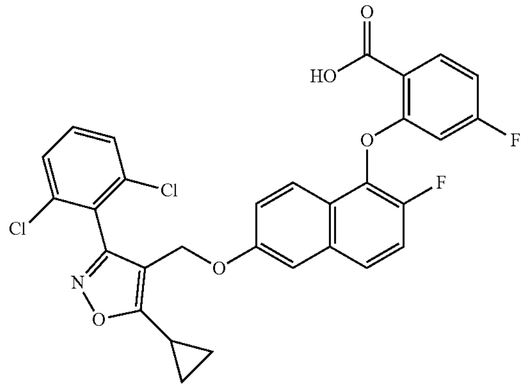
45
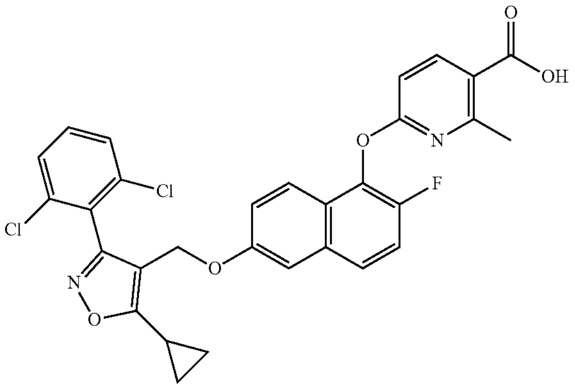
46
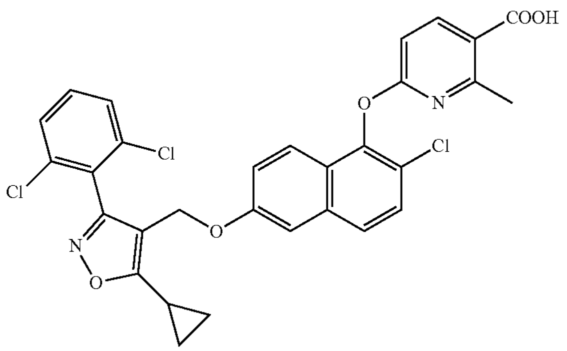

-continued

47

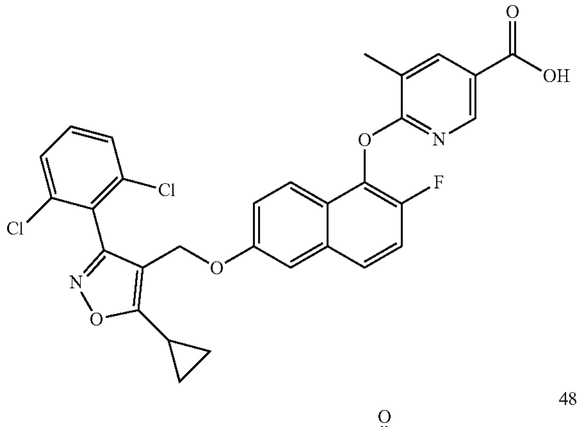

48

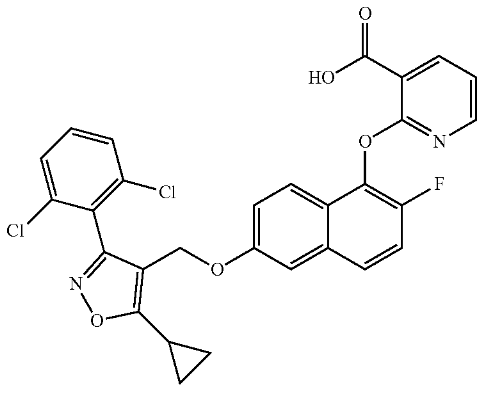

and

49

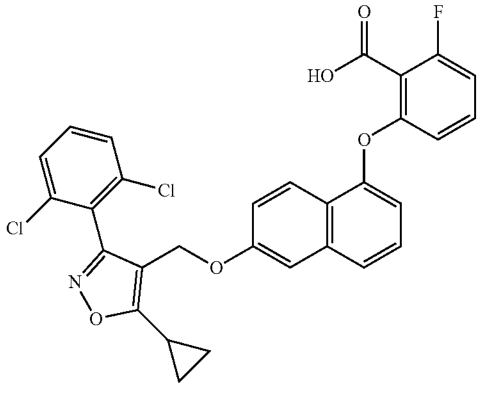

.

14. A pharmaceutical composition comprising a therapeutically effective amount of a compound of claim 1 or a pharmaceutically acceptable salt, an ester or a stereoisomer thereof, and a pharmaceutically acceptable auxiliary material.

15. The pharmaceutical composition according to claim 14, wherein the pharmaceutical composition further comprises a second therapeutic agent for the treatment of non-alcoholic fatty liver disease (NAFLD), nonalcoholic steatohepatitis (NASH), primary biliary cirrhosis (PBC), cholestasis liver tree, chronic liver disease, hepatitis C infection, alcoholic liver disease, hepatic fibrosis, primary sclerosing cholangitis (PSC), gallstones, bile duct atresia, lower urinary tract symptoms and benign prostatic hyperplasia (BPH), ureteral calculi, obesity, type 2 diabetes, atherosclerosis, atherosclerosis, or liver damage caused by hypercholesterolemia or hyperlipidemia.

16. A method for treating a condition or disease mediated by FXR in a subject suffering therefrom, comprising administering to the subject a therapeutically effective amount of the compound of claim 1 or a pharmaceutically acceptable salt, an ester or a stereoisomer thereof.

17. The method according to claim 16, further comprising administering a second therapeutic agent.

18. The method according to claim 16, wherein the condition or the disease is selected from the group consisting of nonalcoholic fatty liver disease (NAFLD), nonalcoholic steatohepatitis (NASH), primary biliary cirrhosis (PBC), cholestasis liver tree, chronic liver disease, hepatitis C infection, alcoholic liver disease, hepatic fibrosis, primary sclerosing cholangitis (PSC), gallstones, bile duct atresia, lower urinary tract symptoms and benign prostatic hyperplasia (BPH), ureteral calculi, obesity, type 2 diabetes, atherosclerosis, atherosclerosis, and liver damage caused by hypercholesterolemia or hyperlipidemia.

19. The compound according to claim 9, or a pharmaceutically acceptable salt, an ester or a stereoisomer thereof, wherein $R^4$ is —COOH.

* * * * *